United States Patent [19]

Fletcher, Jr. et al.

[11] Patent Number: 4,577,024

[45] Date of Patent: Mar. 18, 1986

[54] OXOINDOLIZINE AND OXOINDOLIZINIUM COMPOUNDS USEFUL AS DYES

[75] Inventors: George L. Fletcher, Jr., Pittsford, N.Y.; Steven L. Bender, Pasadena, Calif.; Donald H. Wadsworth, Rochester, N.Y.

[73] Assignee: Eastman Kodak Company, Rochester, N.Y.

[21] Appl. No.: 412,444

[22] Filed: Aug. 27, 1982

Related U.S. Application Data

[63] Continuation-in-part of Ser. No. 278,022, Jun. 29, 1981, abandoned.

[51] Int. Cl.$^4$ .................................. C07D 471/04
[52] U.S. Cl. .................................. 546/183; 544/58.2; 544/105; 544/127; 544/316; 544/319; 546/94; 546/165; 546/166
[58] Field of Search ............... 546/183, 94, 165, 166; 542/429, 433, 434, 442; 544/58.2, 127, 105, 316, 319

[56] References Cited

U.S. PATENT DOCUMENTS

| | | | |
|---|---|---|---|
| 4,106,938 | 8/1978 | Fletcher et al. | 96/48 HD |
| 4,128,422 | 12/1978 | Fletcher et al. | 96/48 HD |
| 4,368,247 | 1/1983 | Fletcher, Jr. et al. | 430/17 |

OTHER PUBLICATIONS

Noller, Chemistry of Org. Cpds., Saunders and Co., (1951), pp. 618–619.
Hackh's Chem. Dictionary, edited by J. Grant, McGraw-Hill (1969), p. 157.
The Theory of the Photographic Process, 4th ed., Mac-Millan Publ. Co., (1977), pp. 194–199.
J. W. Lown et al., "Reaction of Cyclopropenones . . . ", Canadian Journal of Chemistry, vol. 49 (1971), pp. 1165–1175.
T. Eicher et al., "Zur Reaktion Von Cyclopropenone Mit . . . ", Tetrahedron Letters, No. 14, (1979), pp. 1213–1216.
*Research Disclosure*, Apr. 1979, Item No. 18016.
C. Holstead et al., "Some Photothermographic Systems", The Journal of Photo. Sci., vol. 25, No. 6, (1977), pp. 241–245.
A. Kasheres et al., "Cycloaddition Reactions . . . ", Journal of Org. Chem., vol. 41, No. 22, (1976), pp. 3546–3549.
A. Kasheres et al., "Reaction of Diphenylcyclopropenone . . . ", Journal of Org. Chem., vol. 40, No. 10 (1975), pp. 1440–1444.
K. T. Potts et al., "The Chemistry of Cyclopropenones", Chemical Reviews, vol. 74, No. 2 (1974), pp. 189–213.
Kroek et al., Chem. Ber., vol. 104, pp. 1629–1644 (1971).

*Primary Examiner*—Henry R. Jiles
*Assistant Examiner*—Bernard I. Dentz
*Attorney, Agent, or Firm*—Richard E. Knapp

[57] ABSTRACT

Oxoindolizine and oxoindolizinium dyes are novel compounds useful in imaging, such as laser recording and reading. These dyes are formed by (1) the reaction of a cyclopropenone and a pyridine compound, (2) by reaction of (a) color-forming couplers with (b) reaction products from the reaction of cyclopropenones with pyridine compounds, or (3) by condensation reactions of indolizinols, indolizinones, and indolizinium ions.

15 Claims, No Drawings

OXOINDOLIZINE AND OXOINDOLIZINIUM COMPOUNDS USEFUL AS DYES

BACKGROUND OF THE INVENTION

1. Field of the Invention

This invention relates to new oxoindolizine and oxoindolizinium dyes. It also relates to the preparation of such dyes.

2. Description of the State of the Art

Dyes useful in imaging materials are well known in the photographic art. However, a continuing need has existed for new classes of dyes having a wide absorption range and which are prepared without the need for complex multistep reactions.

Attempts have been made to react cyclopropenones with heteroaromatic nitrogen compounds as described in, for example, "Reaction of Cyclopropenones With Heterocyclic Nitrogen Compounds" by J. W. Lown and K. Matsumoto, *Canadian Journal of Chemistry*, Vol. 49, 1971, pages 1165–1175. However, such attempts did not produce an oxoindolizine or oxoindolizinium dye. None of the classes of dyes have involved preparation by means of a simple reaction of a cyclopropenone with a pyridine compound. Also, none of the classes of dyes have involved reaction of (1) color-forming couplers with (2) reaction products from reaction of photosensitive cyclopropenones with pyridine compounds. In addition, none of the classes of dyes have involved color-forming condensation reactions of the reaction products of cyclopropenones and pyridine compounds.

SUMMARY OF THE INVENTION

According to the invention, new oxoindolizine and oxoindolizinium dyes are provided. These dyes are useful, for example, in laser recording and reading. Some of the oxoindolizine and oxoindolizinium dyes are useful as image dyes in photothermographic and thermographic materials and processes.

Oxoindolizine and oxoindolizinium dyes according to the invention are selected from the group consisting of methyleneoxoindolizine, (4-oxoarylene)oxoindolizine, bis-oxoindolizine, bis(oxoindolizinyl)ethylene, (2- and 4-aminoarylene)oxoindolizine and pyridiniumoxoindolizine dyes. An alternative nomenclature for specifying these oxoindolizine and oxoindolizinium dyes is useful. According to this alternative nomenclature, these dyes are specified as 7-methylidene-1 or 3-oxoindolizine dyes; 7-(4-oxo-2,5-cyclohexadien-1-ylidene)-1 or 3-oxoindolizine dyes; 7-(1 or 3-oxoindolizin-7-ylidene)-1 or 3-oxoindolizine dyes; 7-(1 or 3-oxoindolizin-7-ylidene)ethylidene-1 or 3-oxoindolizine dyes; 7-(1 or 3-oxoindolizin-7-ylidene)methylidene-1 or 3-oxoindolizinium salt dyes; 7-(2 or 4-aminoaryl)-1 or 3-oxoindolizine dyes; and 7-1 or 3-oxoindolizine dyes. While the dyes herein are named by means of the former nomenclature it is understood that the latter nomenclature is also useful and generally preferred. In each case 1 or 3-oxoindolizine dyes and 1 or 3-oxoindolizinium dyes contain in the 7-position a chromophore group which enables the dyes to have a maximum absorption at a wavelength within the range of 300 to 1000 nanometers. The oxoindolizine and oxoindolizinium dyes according to the invention are in their keto or enol form. The invention also includes these dyes in their various isomeric and tautomeric forms.

Oxoindolizine dyes according to the invention in their keto form have the following structure:

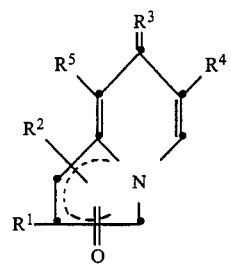

(I)

wherein
$R^1$ and $R^2$ are individually selected from
straight and branched alkyl containing 1 to 18, preferably 1 to 10 carbon atoms, such as methyl, ethyl, propyl and decyl;
aryl containing 6 to 20 carbon atoms, such as phenyl, tolyl, xylyl, methoxyphenyl, 4-t-butylphenyl, naphthyl and methoxynaphthyl; and
polystyryl having appended groups selected from the group consisting of indolizine and indolizinium groups and combinations thereof;
$R^3$ is a divalent group which with the indolizinone nucleus completes an organic chromophore;
$R^4$ is hydrogen or a substituent that does not adversely affect desired dye properties, such as alkyl containing 1 to 18 carbon atoms, such as methyl, ethyl and dodecyl; cyano; acyl containing 2 to 20 carbon atoms, such as acetyl, propionyl, 2-ethylhexanoyl and stearoyl; carboalkoxy containing 1 to 18 carbon atoms, such as carbomethoxy, carboethoxy and carbobutoxy; aminocarbonyl, such as unsubstituted aminocarbonyl, methylaminocarbonyl, dimethylaminocarbonyl and ethylaminocarbonyl; acyloxy containing 2 to 18 carbon atoms, such as acetoxy, propionoxy, butyroxy and lauroyloxy; bromine and chlorine; and
$R^5$ is hydrogen or a substituent that does not adversely affect desired dye properties, such as hydrogen, chlorine, bromine or alkyl containing 1 to 18 carbon atoms, such as methyl, ethyl, propyl, and dodecyl.

Indolizinium dyes according to the invention in their keto form are within the following structure:

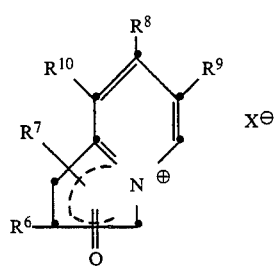

(II)

wherein
$X^\ominus$ is an anion, preferably an acid anion;
$R^6$ and $R^7$ are individually selected from straight and branched alkyl containing 1 to 18, preferably 1 to 10 carbon atoms, such as methyl, ethyl, propyl and decyl;

aryl containing 6 to 20 carbon atoms, such as phenyl, tolyl, xylyl, methoxyphenyl, 4-t-butylphenyl, anisyl, naphthyl and methoxynaphthyl; and polystyryl having appended groups selected from the group consisting of indolizine and indolizinium groups and combinations thereof;

$R^8$ is a monovalent group which with the oxoindolizinium nucleus completes an organic chromophore;

$R^9$ is hydrogen or a substituent that does not adversely affect desired dye properties, such as alkyl containing 1 to 18 carbon atoms, such as methyl, ethyl, and dodecyl; cyano; acyl containing 2 to 20 carbon atoms, such as acetyl, propionyl, 2-ethylhexanoyl and stearoyl; carboalkoxy containing 1 to 18 carbon atoms, such as carbomethoxy, carboethoxy and carbobutoxy; aminocarbonyl, such as unsubstituted aminocarbonyl, methylcarbonyl, dimethylaminocarbonyl, and ethylaminocarbonyl; acyloxy containing 2 to 18 carbon atoms, such as acetoxy, propionoxy, butyroxy and lauroyloxy; bromine and chlorine; and $R^{10}$ is hydrogen or a substituent that does not adversely affect desired dye properties, such as hydrogen, chlorine, bromine or alkyl containing 1 to 18 carbon atoms, such as methyl, ethyl, propyl and dodecyl.

Useful $R^3$ and $R^8$ groups are, for example (a) substituted or unsubstituted heterocyclyl or heterocyclylidene groups optionally appended through methine and polymethine groups, such as (i) indolizine and indolizinium groups illustrated by structures (I) and (II) appended directly as the respective $R^3$ and $R^8$ groups or appended through a substituted or unsubstituted methine or polymethine chain, such as containing 1 to 6 methine groups, (ii) pyridylidene, (iii) pyranyl, (iv) pyranylidene, (v) thiopyranyl, (vi) thiopyranylidene, and (vii) julolidyl; including the onium salts of such heterocyclyl and heterocyclylidene groups, such as the immonium, oxonium and sulfonium salts; and the acid addition salt derivatives of such heterocyclyl and heterocyclylidene groups;

(b) substituted and unsubstituted aminoarylmethine and hydroxyarylmethine, including their tautomers, such as represented by the formula: (Z)(A)(D) wherein Z is a methine or polymethine group, such as containing 1 to 6 methine groups;

A is a substituted or unsubstituted aromatic group, such as arylene containing 6 to 20 carbon atoms, for example, phenylene, phenylidene, naphthylene, and naphthylidene; and D is $-OR^{129}$, $-NR^{130}R^{131}$, $=O$, or $=NR^{132}$ wherein $R^{129}$ is a monovalent cation, preferably hydrogen, $R^{130}$ and $R^{131}$ are independently selected from hydrogen, substituted or unsubstituted alkyl, such as alkyl containing 1 to 20 carbon atoms, alkenyl, such as alkenyl containing 2 to 20 carbon atoms, and aryl, such as aryl containing 6 to 20 carbon atoms, including phenyl and tolyl; or, $R^{130}$ and $R^{131}$ taken together with (A) form a polycyclic heterocyclic group, such as a 9-julolidyl group;

$R^{132}$ is alkyl, such as alkyl containing 1 to 20 carbon atoms or aryl, such as aryl containing 6 to 20 carbon atoms;

(c) a methylene group substituted with at least one, preferably two electronegative groups, such as acyl, cyano, aryl, alkoxycarbonyl, and aminocarbonyl groups; and (d) a formyl group.

$X^{\ominus}$ is an anion, for example, methanesulfonate, trifluoromethanesulfonate, para-toluenesulfonate, bromide, chloride, iodide, and sulfinate.

The term "enol" herein means an enol from the keto form of the dye as well as an enol produced by a protonation reaction or other reaction. For example, typical enols are represented by the formula:

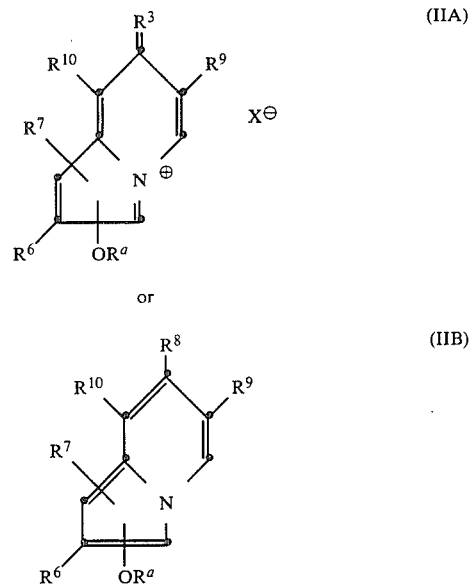

wherein $X^{\ominus}$, $R^3$, $R^6$, $R^7$, $R^8$, $R^9$ and $R^{10}$ are as defined above and $R^a$ is hydrogen or acyl.

The term "acyl" herein means alkylcarbonyl containing 2 to 20 carbon atoms and arylcarbonyl, such as arylcarbonyl containing 7 to 20 carbon atoms.

The term "aryl" herein means unsubstituted aryl and substituted aryl. Aryl herein includes, for example, aryl containing 6 to 20 carbon atoms, such as phenyl, tolyl, xylyl, naphthyl, and methoxyphenyl.

The preparations of oxoindolizine and oxoindolizinium dyes according to the invention do not involve complicated reaction steps as do the preparations of other dyes.

The oxoindolizine and oxoindolizinium dyes according to the invention are prepared by (1) reaction of a cyclopropenone compound with a pyridine compound, or (2) reaction of a cyclopropenone compound with a pyridine compound and then with a color-forming coupler, or (3) a condensation reaction. The term "condensation reaction" herein means a dehydration involving, for example, an active methylene and a carbonyl group.

The pyridine compound herein does not include a pyridine which contains a substituent in the 2-position or 6-position on the pyridine ring. It was found that in reactions (1), (2) and (3) that the pyridine compound does not form an oxoindolizine or oxoindolizinium dye when the pyridine compound contains a substituent in the 2-position or 6-position on the pyridine ring, that is in the position on the ring next to the ring nitrogen atom.

The oxoindolizine and oxoindolizinium dyes according to the invention are useful in imaging materials and processes. The dyes are also useful in, for instance, indicator compositions and laser recording and reading.

The oxoindolizine and oxoindolizinium dyes herein are alternatively named as indolizinone compounds.

DETAILED DESCRIPTION OF THE INVENTION

Many pyridine compounds are useful in forming a dye according to the invention. Examples of useful pyridine compounds are represented by the formula:

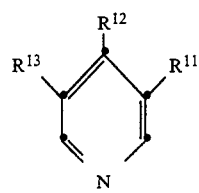 (III)

wherein:

$R^{11}$ is hydrogen, alkyl containing 1 to 20 carbon atoms, such as methyl, ethyl and dodecyl; cyano; acyl containing 2 to 18 carbon atoms, such as acetyl, propionyl, 2-ethylhexanoyl and stearoyl; carboalkoxy, containing 1 to 18 carbon atoms, such as carbomethoxy, carboethoxy and carbobutoxy; aminocarbonyl, such as unsubstituted aminocarbonyl, methylaminocarbonyl, dimethylaminocarbonyl and ethylaminocarbonyl; acyloxy containing 2 to 18 carbon atoms, such as acetoxy, propionoxy, butyroxy and lauroyloxy; bromine and chlorine;

$R^{12}$ is hydrogen, alkyl containing 1 to 18 carbon atoms, such as methyl, ethyl, propyl and dodecyl; cyano; acyl containing 2 to 18 carbon atoms, such as acetyl, propionyl, butyryl and lauryl; benzyl or pyridyl; and $R^{13}$ is hydrogen, chlorine, bromine or alkyl containing 1 to 18 carbon atoms, such as methyl, ethyl, propyl and dodecyl.

Examples of useful pyridine compounds for preparation of dyes according to the invention are:

4,4'-Dipyridylethylene: P-1

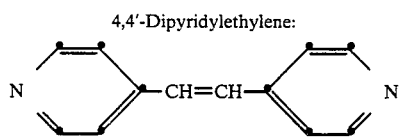

1-Methyl-4-(4-pyridyl)pyridinium-p-toluene-sulfonate: P-2

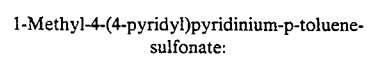

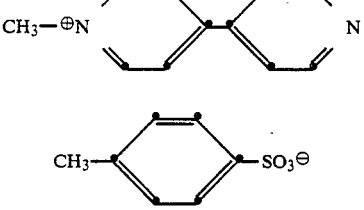

Pyridine: P-3

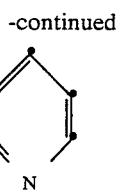

4-Picoline: P-4

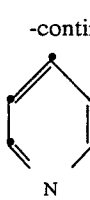

4-Formylpyridine (also known as 4-pyridine-carboxaldehyde): P-5

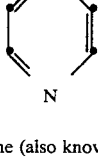

4-(4-Azastyryl)-1-methylpyridinium p-toluene sulfonate: P-6

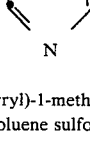

4-Acetylpyridine: P-7

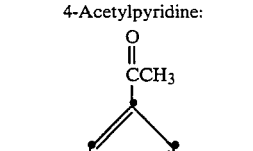

3-Acetylpyridine: P-8

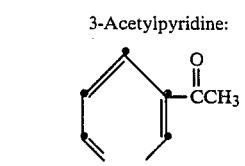

3-Benzylpyridine: P-9

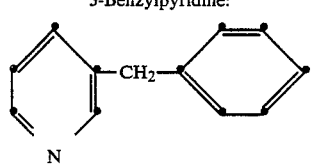

4-Benzylpyridine: P-10

-continued

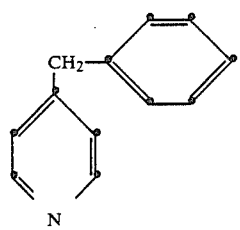

3-Bromopyridine: P-11

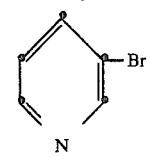

4-(p-chlorobenzyl)pyridine: P-12

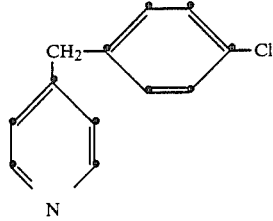

3-Chloropyridine: P-13

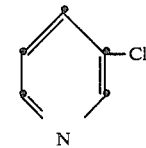

3-Cyanopyridine: P-14

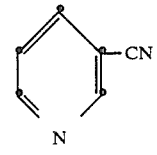

3,5-Dichloropyridine: P-15

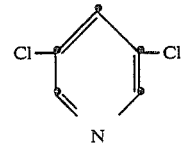

N,N—diethylnicotinamide: P-16

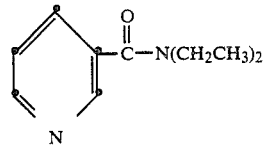

3-Ethylpyridine: P-17

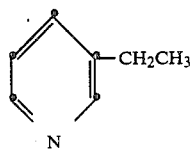

4-Ethylpyridine: P-18

-continued

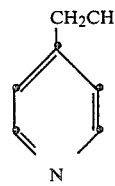

Ethyl 3-pyridylacetate: P-19

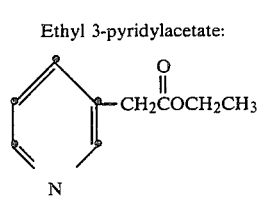

3,4-Lutidine: P-20

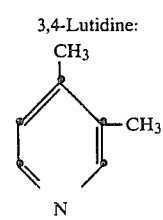

3,5-Lutidine: P-21

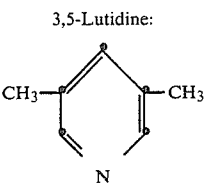

2-Methyl-1,2-di-3-pyridyl-1-oxo-propane: P-22

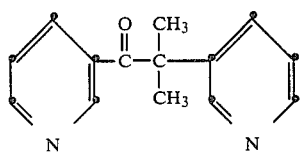

N—methylnicotinamide: P-23

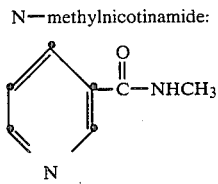

Methyl nicotinate: P-24

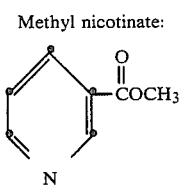

3-Picoline: P-25

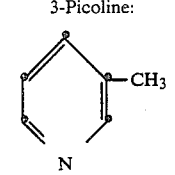

3-Formylpyridine (also known as 3-Pyridinecarboxaldehyde): P-26

3-Cyanomethylpyridine (also known as 3-Pyridylacetonitrile): P-27

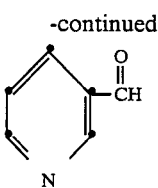

3-(3-pyridyl)-1-propanol: P-28

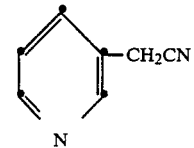

Trans-1-(3-pyridyl)-2-(4-pyridyl)ethylene: P-29

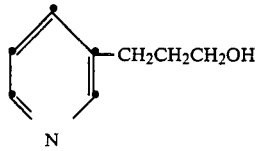

4-Cyanopyridine: P-30

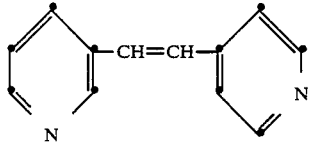

1-Benzyl-4-(4-pyridyl)pyridinium bromide: P-31

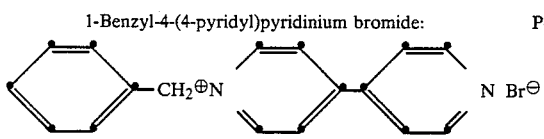

Many cyclopropenones are useful for preparing dyes according to the invention. Examples of useful cyclopropenones are cyclopropenones represented by the formula:

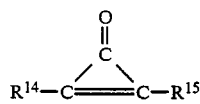

(IV)

wherein: $R^{14}$ and $R^{15}$ are individually aryl containing 6 to 20 carbon atoms, such as phenyl, naphthyl, anthryl, methoxyphenyl and methoxynaphthyl; aralkenyl containing 6 to 20 carbon atoms, such as 2,2-diphenylvinyl, 2-phenylvinyl, 2-naphthylvinyl and 2-methyl-(2-phenylvinyl); alkyl containing 1 to 20, preferably 1 to 10 carbon atoms, such as methyl, ethyl, propyl, decyl and eicosyl; or $R^{14}$ and $R^{15}$ together represent the carbon atoms necessary to complete a cyclic structure, for example, a 7- or 8-member cyclic structure, such as 2,3-pentamethylene.

The aryl group of $R^{14}$ and $R^{15}$ is unsubstituted or substituted by one or more groups selected from the group consisting of:

(1) alkyl or alkoxy containing 1 to 5 carbon atoms, for example, methyl, ethyl, propyl, isopropyl, butyl, methoxy, ethoxy, propoxy and butoxy;
(2) nitro;
(3) aryloxy containing 6 to 10 carbon atoms, such as phenoxy and naphthoxy;
(4) halogen, for example, chlorine, fluorine, iodine and bromine;
(5) a homopolymer or copolymer to which the aryl group is attached as a pendant moiety with the polymer having at least one repeating unit represented by the formula:

wherein:
$R^{16}$ is a lower alkylene group containing from 1 to 5 carbon atoms, such as ethylene and propylene; and
z is at least a portion of the number of repeating units in a polymer chain, such as 10 to 1000.

Examples of useful cyclopropenone compounds are described in U.S. Pat. No. 4,128,422. Some of the cyclopropenones that are useful in preparing indolizinone and indolizinium compounds according to the invention are not particularly sensitive to wavelengths of radiation in the visible region of the spectrum.

Examples of useful cyclopropenones are:
2,3-diphenylcyclopropenone
2-(2-methoxynaphthyl)-3-phenylcyclopropenone
2-(2-methoxynaphthyl)-3-(4-methoxyphenyl)cyclopropenone
2,3-bis(2-methoxynaphthyl)cyclopropenone
2,3-bis(2,4-dimethylphenyl)cyclopropenone
2,3-bis(4-n-butoxyphenyl)cyclopropenone
2,3-bis(4-methoxyphenyl)cyclopropenone
poly[styrene-co-4-(2-phenylcyclopropenonyl)styrene]
2,3-bis(4-phenoxyphenyl)cyclopropenone
2-(4-n-butoxyphenyl)-3-phenylcyclopropenone
2-(2,5-dimethylphenyl)-3-phenylcyclopropenone
2-(4-methoxyphenyl)-3-phenylcyclopropenone
2-(2,4-dimethoxyphenyl)-3-phenylcyclopropenone
2,3-bis(2,4-dimethoxyphenyl)cyclopropenone
2,3-bis(2-methyl-5-isopropylphenyl)cyclopropenone
2,3-bis(3-nitrophenyl)cyclopropenone
2,3-bis(2,5-dimethylphenyl)cyclopropenone
2,3-bis(4-methylphenyl)cyclopropenone
2,3-di-n-propylcyclopropenone
2,3-pentamethylenecyclopropenone
2-(2,4-dimethoxyphenyl)-3-(2,4-dimethylphenyl)cyclopropenone
2,3-bis(2,5-dimethoxyphenyl)cyclopropenone
2-(2,4,6-trimethylphenyl)-3-phenylcyclopropenone
2-phenyl-3-(2,5-dimethoxyphenyl)cyclopropenone
2-phenyl-3-(2,4-dimethylphenyl)cyclopropenone
2,3-bis(2,2-diphenylvinyl)cyclopropenone
2,3-bis(2-methyl-2-phenylvinyl)cyclopropenone The described cyclopropenones are prepared by processes known in the organic synthesis art.

The cyclopropenones are spectrally sensitized, if desired. Spectral sensitization procedures and compounds for spectrally sensitizing cyclopropenones are known in the photographic art, such as described in U.S. Pat. No. 4,128,422. Useful spectral sensitizers are, for example: 2-benzoylmethylene-3-methylnaphthyl-(2,1-d)thiazoline; 3-carboxymethyl-5-(3-ethylbenzothiazolinylidene)-rhodanine; anhydro-3,3'-disulfopropyl-5-methoxythiacyaninehydroxide; 2-[bis(2-furoyl)-methylene]-1-methylnaphthyl-[1,2-d]-thiazoline; and 3-benzoyl-7-methoxycoumarin. Combinations of spectral sensitizers are also useful.

Especially useful phenolic couplers, aniline couplers and active methylene couplers for forming dyes according to the invention are couplers which are useful in the photographic art for producing dye images.

The term "phenolic coupler" herein means a phenolic compound or naphtholic compound which forms a dye by reaction with an oxoindolizine or oxoindolizinium compound according to the invention.

Examples of useful phenolic couplers are represented by the formula:

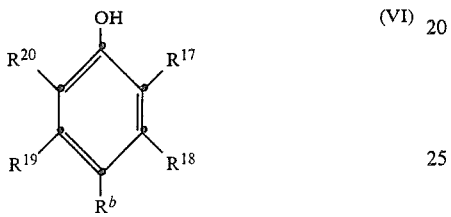

(VI)

wherein:

$R^b$, $R^{17}$, $R^{18}$, $R^{19}$ and $R^{20}$ individually represent substituents which do not adversely affect the desired indolizinone and indolizinium dyes, such as by altering the solubility or desired dye hue, and individually represent substituents that are useful in phenolic couplers in the photographic art, such as described in, for example, U.S. Pat. No. 3,620,747, the description of which is incorporated herein by reference. In Structure VI at least one of $R^{17}$, $R^{20}$ and $R^b$ is hydrogen. For example, $R^b$, $R^{17}$ and $R^{18}$ are individually hydrogen; hydroxyl; alkyl containing 1 to 22 carbon atoms, such as methyl, ethyl, propyl and decyl; aryl containing 6 to 20 carbon atoms, such as phenyl and tolyl; amino; carboxamido; sulfonamido; sulfamyl; carbamyl; halogen, such as chlorine, fluorine, bromine and iodine; and alkoxy containing 1 to 18 carbon atoms, such as methoxy, ethoxy and propoxy;

$R^{19}$ and $R^{20}$ are individually hydrogen, alkyl containing 1 to 22 carbon atoms, such as methyl, ethyl, propyl and decyl; aryl containing 6 to 20 carbon atoms, such as phenyl and tolyl; amino; carboxamido; sulfonamido, sulfamyl; carbamyl; halogen, such as chlorine, fluorine, bromine and iodine; and alkoxy containing 1 to 18 carbon atoms, such as methoxy, ethoxy and propoxy; or $R^{19}$ and $R^{20}$ taken together represent the atoms necessary to complete a benzo group which is unsubstituted or substituted by at least one of the groups given for $R^{17}$;

Examples of useful phenolic couplers are:

2-Acetylamino-5-methylphenol  C-1

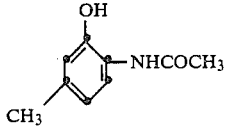

2-[α-(4'-tert.-amylphenoxy)-butyrylamino]-5-methyl-1-phenol  C-2

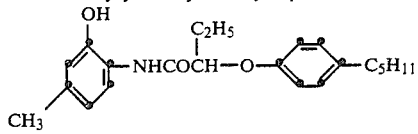

2-cyanoacetamidophenol  C-3

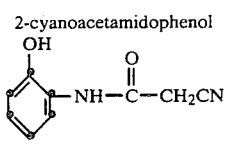

2-(2-stearoyloxyethyl)iminomethylphenol  C-4

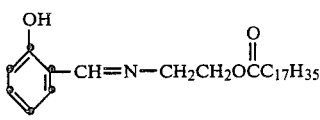

2-octadecyloxyphenol  C-5

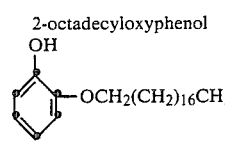

2-perfluorobutyramido-5-propionamidophenyl  C-6

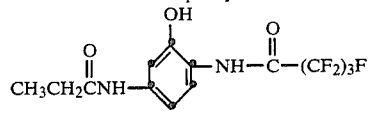

2-octadecyl aminocarbonyl-1-naphthol  C-7

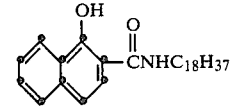

2-(2-sulfonoxy-4-stearoylamino anilinocarbonyl)-1-naphthol  C-8

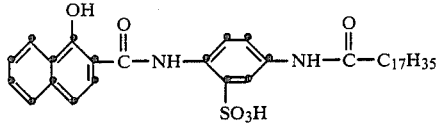

2-(propylaminocarbonyl)-1-naphthol  C-9

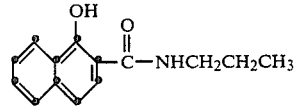

2-[α-(4-tert-amylphenoxy)butyryl amino]phenol  C-10

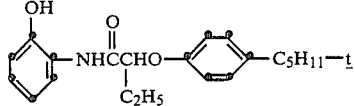

2-(N—methylanilinocarbonyl)-1-naphthol  C-11

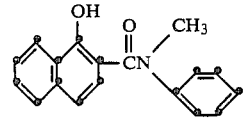

-continued

2-[2-(2-acetamidophenyl)ether aminocarbonyl)-1-naphthol   C-12

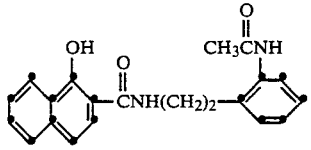

2-(4-tert-butylbenzamido resorcinol   C-13

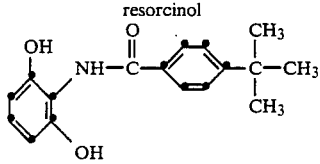

resorcinol   C-14

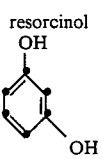

2-(2-amyloxybenzamido)resorcinol   C-15

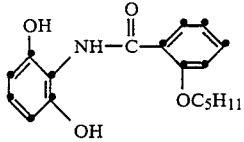

bis-4,4'-resorcinyl sulfide   C-16

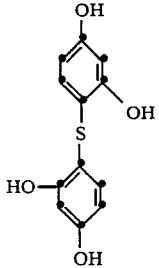

2-propinoamidoresorcinol   C-17

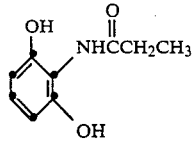

2-benzamidoresorcinol   C-18

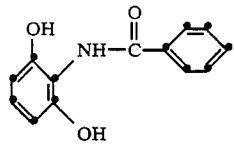

2,6-di-tert-butylphenol

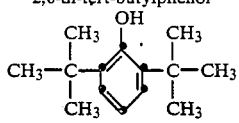

The term "aniline coupler" herein means an aniline compound or related derivative which forms a dye by reaction with an oxoindolizine or oxoindolizinium compound according to the invention.

Examples of useful aniline couplers and derivatives thereof useful in forming oxoindolizine and oxoindolizinium dyes according to the invention are represented by the formulas:

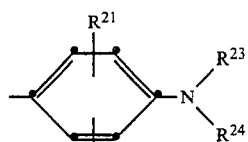 (VI)

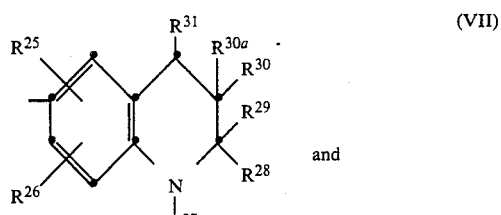 (VII)

and

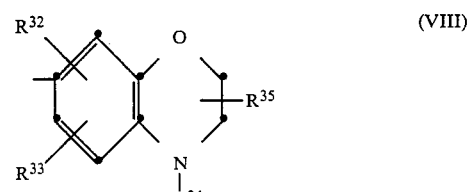 (VIII)

wherein $R^{21}$, $R^{22}$, $R^{25}$, $R^{26}$, $R^{32}$ and $R^{33}$ are individually hydrogen; fluorine; chlorine; bromine; alkyl containing 1 to 6 carbon atoms; cycloalkyl containing 3 to 10 carbon atoms; alkoxy containing 1 to 4 carbon atoms; phenoxy; alkylthio, such as alkylthio containing 1 to 4 carbon atoms; arylthio, such as arylthio containing 6 to 20 carbon atoms; and groups represented by the formula —NH—X—$R^{36}$ in which X is —CO—, —COO or —SO$_2$—;

$R^{23}$, $R^{24}$, $R^{27}$ and $R^{34}$ are individually selected from hydrogen; cycloalkyl, such as cycloalkyl containing 6 to 20 carbon atoms; straight or branched alkenyl containing 2 to 10 carbon atoms; alkyl containing 1 to 18 carbon atoms, or $R^{23}$ or $R^{24}$ are —S—$R^{37}$, or $R^{23}$ and $R^{24}$ together represent the atoms necessary to complete a 5- or 6-member heterocyclic ring with the nitrogen atom to which they are bonded, such as atoms completing a pentamethylene, ethyleneoxyethylene or ethylenesulfonylethylene group which forms a ring or a julolidyl group;

$R^{28}$, $R^{29}$, $R^{30}$, $R^{30a}$, $R^{31}$ and $R^{35}$ are individually selected from hydrogen and alkyl containing 1 to 6 carbon atoms;

$R^{36}$ is alkyl containing 1 to 6 carbon atoms or alkyl substituted by a group that does not adversely affect the desired indolizinone or indolizinium dye, such as halogen, hydroxy, phenoxy, aryl, such as aryl containing 6 to 20 carbon atoms, cyano, cycloalkyl, such as cycloalkyl containing 6 to 12 carbon atoms, alkylsulfonyl containing 1 to 6 carbon atoms, alkylthio containing 1 to 6 carbon atoms, alkanoyloxy containing 1 to 6 carbon atoms and alkoxy containing 1 to 6 carbon atoms; when X is —CO—, then $R^{36}$ is also selected from hydrogen, amino, alkenyl containing 2 to 6 carbon atoms, alkylamino containing 1 to 6 carbon atoms, alkyl-carbamoyl containing 1 to 6 carbon atoms, dialkylamino containing 2 to 12 carbon atoms, arylamino containing 6 to 12 carbon atoms, aryl containing 6 to 20 carbon atoms and furyl.

When $R^{23}$, $R^{24}$, $R^{27}$ or $R^{34}$ are alkyl, the alkyl is unsubstituted or substituted by, for example, hydroxy, halogen, cyano, alkoxy containing 1 to 6 carbon atoms, alkoxyalkoxy containing 2 to 8 carbon atoms, hydroxyalkoxy containing 1 to 4 carbon atoms, succinimido, glutarimido, phenylcarbamoyloxy, phthalimido, phthalimidino, 2-pyrrolidono, cyclohexyl, phenoxy, phenyl or phenyl substituted by alkyl containing 1 to 6 carbon atoms, alkoxy containing 1 to 6 carbon atoms, halogen, alkanoylamino containing 1 to 6 carbon atoms; cyano or alkoxycarbonyl containing 2 to 6 carbon atoms; sulfamoyl; alkylsulfamoyl containing 1 to 6 carbon atoms; vinylsulfonyl; acrylamido; phthalimido; alkylsulfonamido, such as alkylsulfonamido containing 1 to 6 carbon atoms; phenylsulfonamido; alkoxycarbonylamino containing 1 to 6 carbon atoms; alkylcarbamoyloxy containing 1 to 6 carbon atoms; alkoxycarbonyloxy containing 1 to 6 carbon atoms; alkenylcarbonylamino containing 3 to 6 carbon atoms; groups represented by the formula:

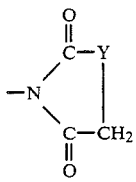

wherein
Y is —NH—,

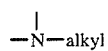

containing 1 to 6 carbon atoms, —O—, —S—, or —CH$_2$O—; wherein $R^{37}$ is alkyl containing 1 to 6 carbon atoms, phenyl, phenyl substituted with halogen, alkoxy containing 1 to 6 carbon atoms, alkanoylamino containing 1 to 6 carbon atoms, cyano or lower alkoxycarbonyl, pyridyl, pyrimidinyl, benzoxazolyl, benzimidazolyl, benzothiazolyl, triazolyl; SO$_2$R$^{39}$; —COOR$^{40}$; —OXR$^{41}$; —NH—X—R$^{42}$; —X—R$^{43}$; —O—CO—R$^{44}$; —CONR$^{45}$R$^{46}$; —SO$_2$NHR$^{47}$; —SO$_2$NR$^{48}$R$^{49}$; wherein $R^{39}$, $R^{40}$, $R^{41}$, $R^{42}$, $R^{43}$ and $R^{44}$ are individually selected from unsubstituted alkyl containing 1 to 6 carbon atoms and alkyl containing 1 to 6 carbon atoms substituted by at least one group that does not adversely affect the desired oxoindolizine or oxoindolizinium dye, such as halogen, hydroxy, phenoxy, aryl containing 6 to 20 carbon atoms, cyano, cycloalkyl containing 6 to 12 carbon atoms, alkylsulfonyl containing 1 to 6 carbon atoms, alkylthio containing 1 to 6 carbon atoms, alkanoyloxy containing 1 to 6 carbon atoms; and alkoxy containing 1 to 6 carbon atoms, and when X is —CO—, then $R^{41}$, $R^{42}$ and $R^{43}$ are also individually selected from hydrogen, amino, alkenyl containing 2 to 6 carbon atoms, alkylamino containing 1 to 6 carbon atoms, alkyl carbamoyl containing 2 to 6 carbon atoms, dialkylamino containing 2 to 6 carbon atoms, arylamino containing 6 to 20 carbon atoms, aryl containing 6 to 20 carbon atoms or furyl;

$R^{45}$, $R^{46}$, $R^{47}$, $R^{48}$ and $R^{49}$ are individually selected from hydrogen, unsubstituted alkyl containing 1 to 6 carbon atoms and alkyl containing 1 to 6 carbon atoms substituted by at least one group that does not adversely affect the desired oxoindolizine or oxoindolizinium dye, such as halogen, hydroxy, phenoxy, aryl containing 6 to 20 carbon atoms, cyano, cycloalkyl containing 6 to 12 carbon atoms, alkylsulfonyl containing 1 to 6 carbon atoms, alkylthio containing 1 to 6 carbon atoms, alkanoyloxy containing 1 to 6 carbon atoms and alkoxy containing 1 to 6 carbon atoms, cyano, alkanoyloxy containing 1 to 6 carbon atoms, phenoxy, phenoxy substituted by at least one of alkyl containing 1 to 6 carbon atoms, alkoxy containing 1 to 6 carbon atoms, and halogen.

The term "cycloalkyl" herein means an unsubstituted cycloalkyl group or a cycloalkyl group containing substituents that do not adversely affect an oxoindolizine or oxoindolizinium dye according to the invention. The cycloalkyl group, for example, contains 3 to 7 carbon atoms and is unsubstituted or substituted by one or two groups selected from alkyl containing 1 to 4 carbon atoms, hydroxyl, alkoxy containing 1 to 4 carbon atoms, phenyl or phenyl containing an alkyl group containing 1 to 4 carbon atoms, alkoxy containing 1 to 4 carbon atoms, halogen, alkanoylamino, cyano and alkoxycarbonyl, such as alkoxycarbonyl containing 1 to 4 carbon atoms.

Examples of useful aniline couplers are as follows:

N,N—dimethylaniline  AN-1

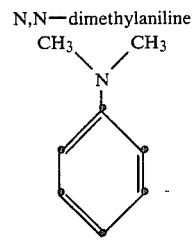

julolidine  AN-2

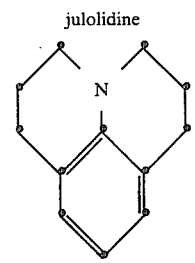

N,N—diethylaniline  AN-3

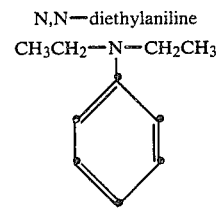

N—phenylpiperidine  AN-4

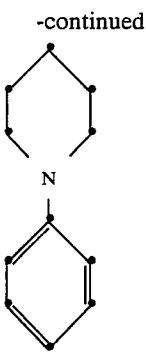

Examples of useful active methylene couplers for forming dyes according to the invention are represented by the formula:

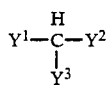  (IX)

wherein:
Y¹ and Y² are the same or different electronegative groups, such as aryl containing 6 to 20 carbon atoms, such as phenyl and naphthyl; cyano; acyl containing 2 to 18 carbon atoms, such as acetyl, propionyl and butyryl; carboalkoxy containing 1 to 18 carbon atoms, such as carbomethoxy, carboethoxy, carbobutoxy and carboamyloxy; aminocarbonyl containing 1 to 18 carbon atoms, such as unsubstituted aminocarbonyl, methylaminocarbonyl, dimethylaminocarbonyl and ethylaminocarbonyl; or oxo-, thio- or selenopyrylium; or oxoindolizinium; or Y² is hydrogen; and Y³ is hydrogen or halogen, such as chlorine, bromine and iodine.

Preferred active methylene couplers are ketomethylene couplers. Other useful active methylene couplers include those known to be useful in the photographic art, such as pyrazalinone and coumarin couplers.

Examples of preferred ketomethylene couplers are represented by the formula:

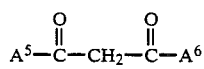  (X)

wherein: A⁵ and A⁶ are individually selected from alkyl containing 1 to 18 carbon atoms, such as methyl, ethyl, propyl and amyl; aryl containing 6 to 14 carbon atoms, such as phenyl, naphthyl and anthryl; hydroxy; alkoxy, such as alkoxy containing 1 to 6 carbon atoms; amino; substituted amino; or thiol.

Ketocarboxamides are examples of especially useful ketomethylene couplers for forming dyes according to the invention. Examples of useful ketocarboxamides are represented by the formula:

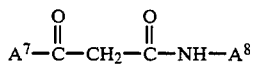  (XI)

wherein: A⁷ and A⁸ are individually selected from alkyl containing 1 to 18 carbon atoms, such as methyl, ethyl, propyl, butyl, amyl, decyl and stearyl; and aryl containing 6 to 14 carbon atoms, such as phenyl, naphthyl, and anthryl; carbonyl; amino and vinyl.

Other particularly useful active methylene couplers are alkyl flavylium salts and alkyl pyrylium salts, such as described in U.S. Pat. Nos. 3,141,770 and 3,250,615.

Examples of useful methylene couplers include the following:

2,6-Diphenyl-4-methylpyrylium perchlorate  M-1

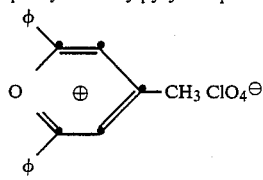

2,4-Diphenyl-6-methylpyrylium perchlorate  M-2

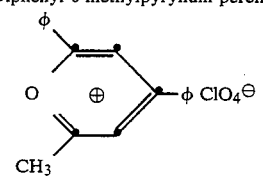

2,6-Diphenyl-4-methylthiopyrylium perchlorate  M-3

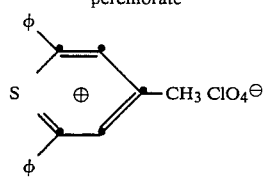

4-Methyl-2-phenylflavylium perchlorate  M-4

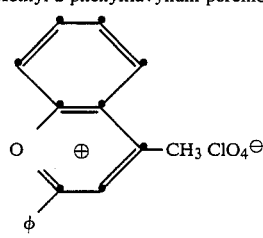

2-Methyl-4-phenylflavylium perchlorate  M-5

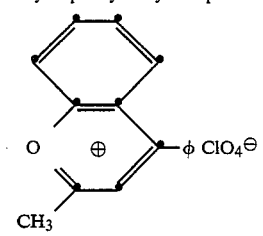

4-Methyl-2-phenylthioflavylium perchlorate  M-6

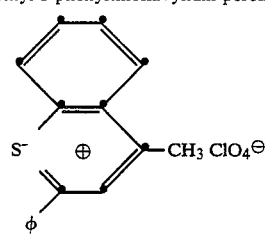

2,6-di-(2-thiopheneyl)-4-methylpyrylium fluoborate  M-7

-continued

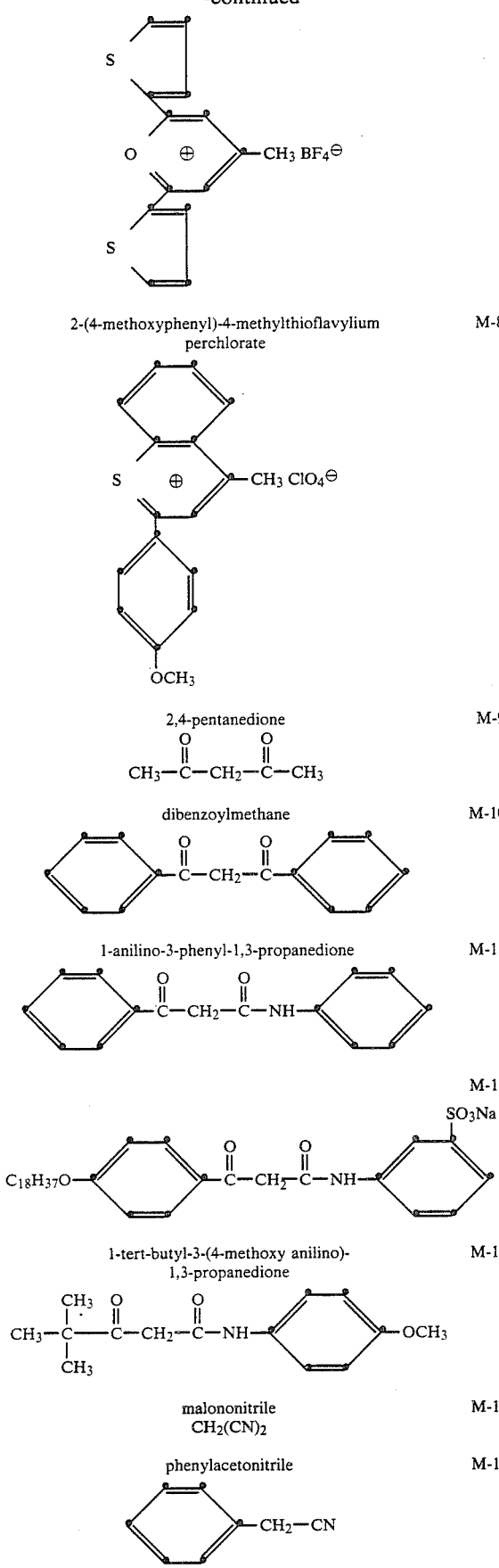

2-(4-methoxyphenyl)-4-methylthioflavylium perchlorate   M-8

2,4-pentanedione   M-9
$$CH_3-\overset{O}{\underset{\|}{C}}-CH_2-\overset{O}{\underset{\|}{C}}-CH_3$$

dibenzoylmethane   M-10

1-anilino-3-phenyl-1,3-propanedione   M-11

M-12

1-tert-butyl-3-(4-methoxy anilino)-1,3-propanedione   M-13 malononitrile   M-14
$CH_2(CN)_2$ phenylacetonitrile   M-15

-continued phenylacetamide   M-16
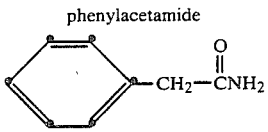

N—phenyl acetylacetamide   M-17
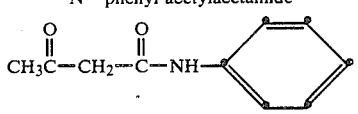

bis-nitrophenylmethane   M-18
$CH_2(C_6H_4NO_2)_2$ methyl cyanoacetate   M-19
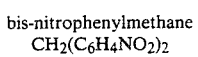

2,2-dimethyl-m-dioxane-4,6-dione   M-20
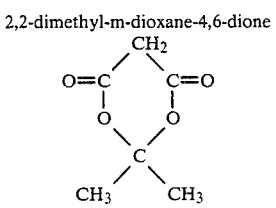

cyanoacetamide   M-21
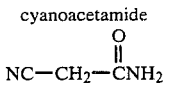

The designation $\phi$ herein means a phenyl group.

Other particularly useful active methylene couplers are alkyl indolizinonium salts represented by the formula:

$$\text{(XII)}$$

wherein
$R^{50}$ and $R^{51}$ are individually aryl containing 6 to 14 carbon atoms, such as phenyl, naphthyl, anthryl, methoxyphenyl and methoxynaphthyl; aralkenyl containing 6 to 14 carbon atoms, such as 2,2-diphenylvinyl, 2-phenylvinyl, 2-naphthylvinyl and 2-methyl(2-phenylvinyl); alkyl containing 1 to 20 carbon atoms, such as methyl, ethyl, propyl, decyl and eicosyl; or $R^{50}$ and $R^{51}$ together represent the carbon atoms necessary to complete a cyclic structure, such as 2,3-pentamethylene; and $R^{52}$ is a substituent which does not interfere with the coupling action of the indolizinium salt and does not adversely affect the desired properties of a resulting oxoindolizinium or oxoindolizine dye, such as hydrogen; carboxyl; alkyl containing 1 to 18 carbon atoms, for example, methyl, ethyl, propyl and dodecyl; cyano; and, aryl containing 6 to 20 carbon atoms, such as phenyl and xylyl;

$X^\ominus$ is an anion as defined above, such as $CF_3SO_3^\ominus$, $BR^\ominus$ and $BF_4^\ominus$.

Another method of preparation of oxoindolizine and oxoindolizinium dyes within Structures I and II comprises condensation of indolizinols, indolizinones or indolizinonium ions with active —CH— compounds which complete an organic chromophore. Such indolizinols (IA), indolizinones (IB) and indolizinonium (IC) ions are represented by the formulas:

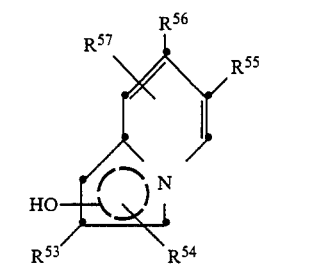
(IA)

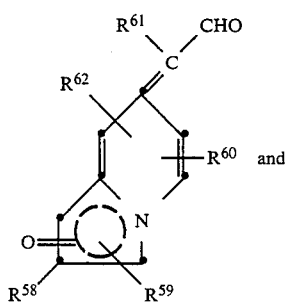
(IIA)

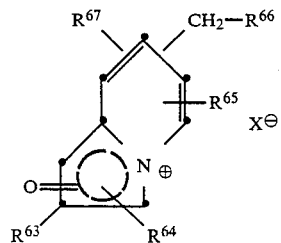
(IIIA)

wherein $X^\ominus$ is an anion as defined above;

$R^{53}$, $R^{54}$, $R^{58}$, $R^{59}$, $R^{63}$ and $R^{64}$ are individually aryl containing 6 to 14 carbon atoms, such as phenyl, naphthyl, anthryl, methoxyphenyl and methoxynaphthyl; aralkenyl containing 6 to 14 carbon atoms, such as 2,2-diphenylvinyl, 2-phenylvinyl, 2-naphthylvinyl and 2-methyl-(2-phenylvinyl); alkyl containing 1 to 20 carbon atoms, such as methyl, ethyl, propyl, decyl and eicosyl; or $R^{53}$ and $R^{54}$, $R^{58}$ and $R^{59}$, and $R^{63}$ and $R^{64}$ together represent the carbon atoms necessary to complete a cyclic structure, such as 2,3-pentamethylene;

$R^{55}$, $R^{60}$ and $R^{65}$ are individually hydrogen, alkyl containing 1 to 18 carbon atoms, such as methyl, ethyl, and dodecyl; cyano; acyl containing 2 to 18 carbon atoms, such as acetyl, propionyl, 2-ethylhexanoyl and stearoyl; carboalkoxy containing 1 to 18 carbon atoms, such as carbomethoxy, carboethoxy and carbobutoxy; aminocarbonyl, such as unsubstituted aminocarbonyl, methylaminocarbonyl, dimethylaminocarbonyl and ethylaminocarbonyl; acyloxy containing 2 to 18 carbon atoms, such as acetoxy, propionoxy, butyroxy and lauroyloxy; bromine and chlorine;

$R^{56}$ is hydrogen; alkyl containing 1 to 18 carbon atoms, such as methyl, ethyl, propyl and dodecyl; acyl containing 2 to 18 carbon atoms, such as acetyl, propionyl, butyryl and lauryl; benzyl or pyridyl;

$R^{57}$, $R^{62}$ and $R^{67}$ are individually hydrogen; chlorine; bromine; or, alkyl containing 1 to 18 carbon atoms, such as methyl, ethyl, propyl and dodecyl;

$R^{61}$ is alkyl containing 1 to 18 carbon atoms, such as methyl, ethyl, propyl, butyl and decyl; and $R^{66}$ is alkyl containing 1 to 18 carbon atoms; hydrogen; carbonyl; alkoxycarbonyl, such as methoxycarbonyl, ethoxycarbonyl and propoxycarbonyl; cyano; and carboxamido.

Such indolizinols (IA), indolizinones (IB) and indolizinonium (IC) ions are prepared by reacting a cyclopropenone with a pyridine compound as described.

The term "active —CH— compounds" herein means aldehyde and ketone compounds which are capable of condensing with the active methylene of the indolizinonium ion (IIIA) and which have electropositive or electronegative substituents which complete a chromophore with the indolizinonium ion (IIIA). The term "active —CH— compounds" also means active methylene compounds that are capable of condensing with indolizinols (IA) or indolizinones (IIA) to complete a chromophore. Examples of useful "active —CH— compounds" are as follows:

1,2-diphenyl-7-formyl-3-indolizinol

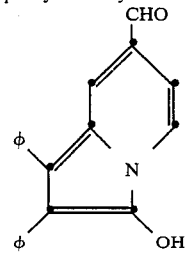

7-formylmethylidene-2,3-diphenyl-1(7H)—indolizinone

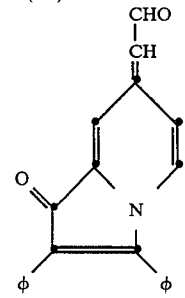

1,2-diphenyl-7-methyl-3-indolizinonium trifluoromethane sulfonate

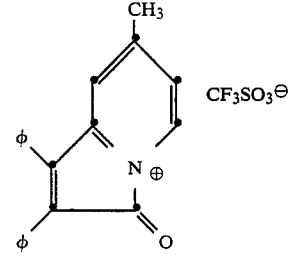

-continued 7-cyanomethyl-2,3-diphenyl-1-indoli-
zinonium trifluoromethane sulfonate

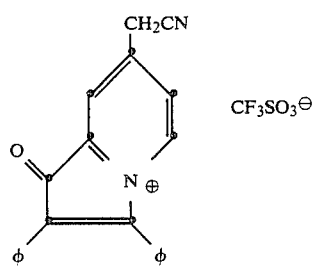

2,3-diphenyl-6-methyl-1-indolizinonium
trifluoromethane sulfonate

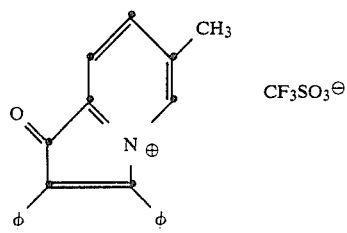

p-dimethylaminocinnamaldehyde

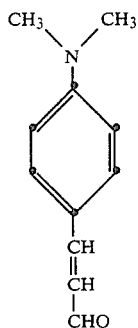

p-hydroxybenzaldehyde

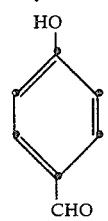

p-hydroxycinnamaldehyde

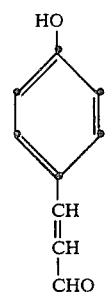

1-dimethylamino-4-formyl naphthalene

-continued

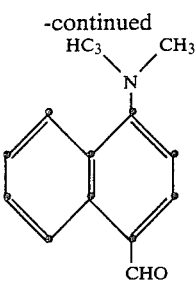

p-nitrobenzaldehyde

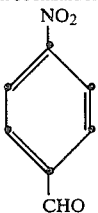

4-dimethylaminobenzaldehyde

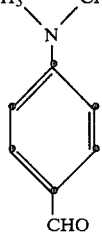

1,2-dimethyl-6-formyl-1,2,3,4-tetrahydro-
quinoline

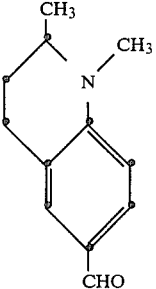

2,6-diphenyl-4-formylmethylidene-
(4H)pyran

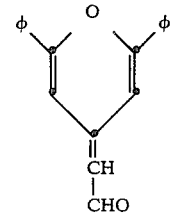

9-formyljulolidine

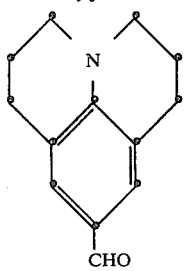

1-chloroethyl-6-formyl-2,2,4,7-tetra-
methyl-1,2,3,4-tetrahydroquinoline

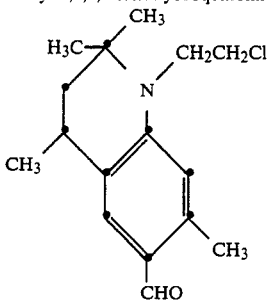

Many oxoindolizine dyes according to the invention are formed by the reaction of a phenolic coupler with an appropriate oxoindolizine. Examples of useful oxoindolizine dyes that are formed by reaction of phenolic couplers with an oxoindolizine are represented by the formulas:

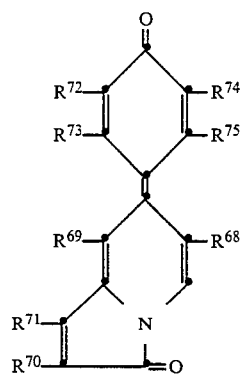

(XIII)

and

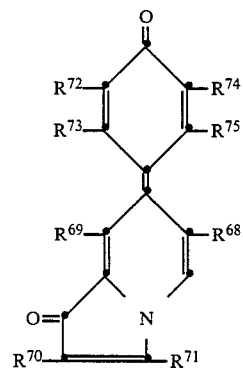

(XIV)

wherein:

$R^{68}$ is hydrogen or a substituent that does not adversely affect desired dye properties, such as alkyl containing 1 to 18 carbon atoms, such as methyl, ethyl, and dodecyl; cyano; acyl containing 2 to 18 carbon atoms, such as acetyl, propionyl, 2-ethylhexanoyl and stearoyl; carboalkoxy containing 1 to 18 carbon atoms, such as carbomethoxy, carboethoxy and carbobutoxy; aminocarbonyl, such as unsubstituted aminocarbonyl, methylaminocarbonyl, dimethylaminocarbonyl and ethylaminocarbonyl; acyloxy containing 2 to 18 carbon atoms, such as acetoxy, propionoxy, butyroxy and lauroyloxy; bromine or chlorine;

$R^{69}$ is hydrogen or a substituent that does not adversely affect desired dye properties, such as chlorine, bromine or alkyl containing 1 to 18 carbon atoms, such as methyl, ethyl, propyl and dodecyl;

$R^{70}$ and $R^{71}$ are individually alkyl, such as alkyl containing 1 to 18, preferably 1 to 10 carbon atoms, such as methyl, ethyl, propyl and decyl or aryl containing 6 to 20 carbon atoms, such as phenyl, tolyl, xylyl, methoxyphenyl, 4-t-butylphenyl, anisyl, naphthyl and methoxynaphthyl;

$R^{72}$ and $R^{73}$ are individually hydrogen, alkyl containing 1 to 22 carbon atoms, such as methyl, ethyl, propyl and decyl; aryl containing 6 to 20 carbon atoms, such as phenyl and tolyl; amino; carboxamido; sulfonamido; sulfamyl; carbamyl; halogen, including chlorine, fluorine, bromine and iodine; and alkoxy containing 1 to 18 carbon atoms, such as methoxy, ethoxy and propoxy; or $R^{72}$ and $R^{73}$ together represent the atoms necessary to complete a benzo group which is unsubstituted or substituted by at least one of the groups given for $R^{17}$; and $R^{74}$ and $R^{75}$ are individually hydrogen; hydroxy; alkyl containing 1 to 22 carbon atoms, such as methyl, ethyl, propyl and decyl; aryl containing 6 to 20 carbon atoms, such as phenyl and tolyl; amino; carboxamido; sulfonamido; sulfamyl; carbamyl; halogen, including chlorine fluorine bromine and iodine; and alkoxy containing 1 to 18 carbon atoms, such as methoxy, ethoxy and propoxy.

An example of a useful class of oxoindolizine dyes prepared from phenolic couplers are those in which the phenolic couplers are resorcinolic couplers. Resorcinolic couplers form compounds wherein $R^{75}$ is hydroxy.

Examples of oxoindolizine dyes prepared from phenolic couplers are as follows:

1,2-diphenyl-7-(4-oxo-2-hydroxy-1-
phenylidene)-3(7H)—indolizinone

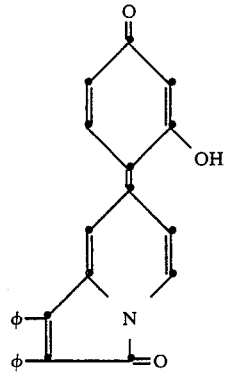

1,2-diphenyl-7-(4-oxo-1-naphthylidene)-3(7H)—indolizinone

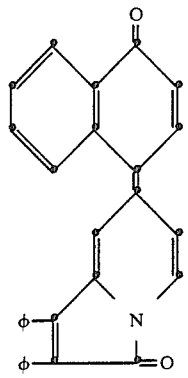

1,2-diphenyl-6-methyl-7-(4-oxo-1-phenylidene)-
3(7H)—indolizinone

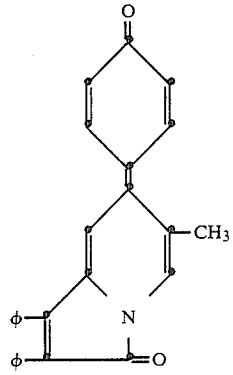

2,3-diphenyl-6-formyl-7-(4-oxo-1-phenylidene)-
1-(7H)—indolizinone

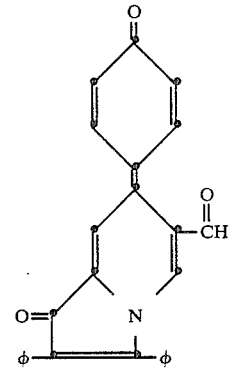

6-diethylaminocarbonyl-2,3-diphenyl-(4-
oxo-1-phenylidene)-1(7H)—indolizinone

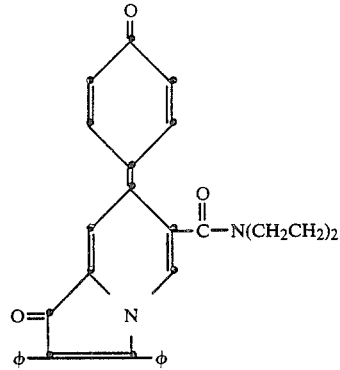

1,2-diphenyl-6-ethyl-7-(4-oxo-1-phenylidene)-
3(7H)—indolizinone

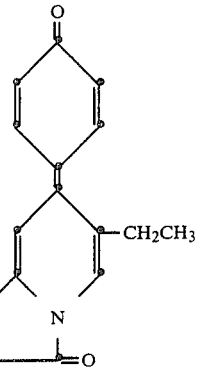

6-cyanomethyl-1,2-diphenyl-7-(4-oxo-1-
phenylidene)-3(7H)—indolizinone

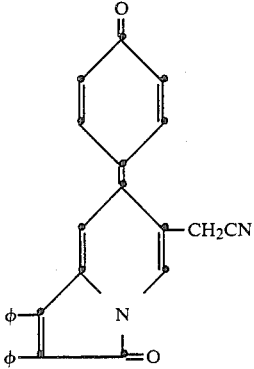

1,2-diphenyl-6-(3-hydroxypropyl)-7-(4-oxo-
1-phenylidene)-3(7H)—indolizinone

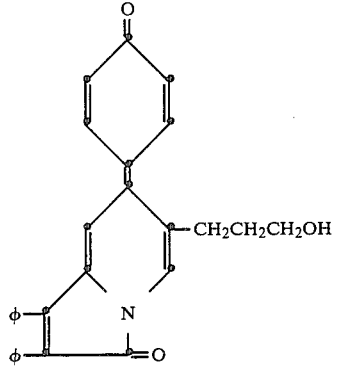

1,2-diphenyl-6-ethoxycarbonylmethyl-7-(4-
oxo-1-phenylidene)-3(7H)—indolizinone

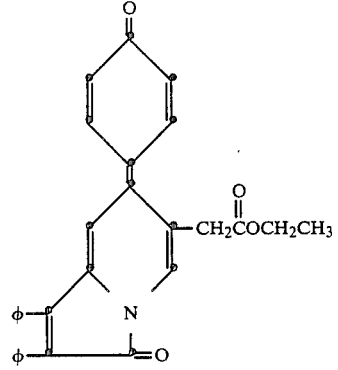

6,8-dimethyl-1,2-diphenyl-7-(4-oxo-1-
phenylidene)-3(7H)—indolizinone

-continued

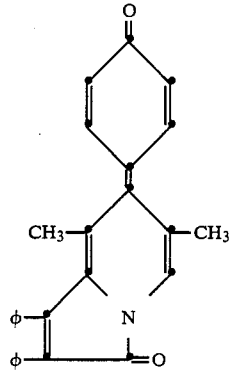

2,3-diphenyl-6-methylaminocarbonyl-7-(4-oxo-1-phenylidene)-1(7H)—indolizinone

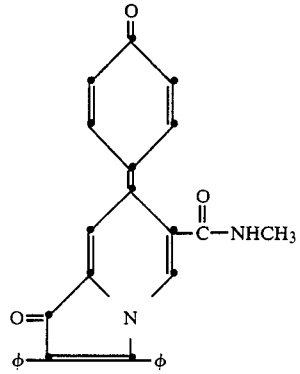

2,3-diphenyl-6-methoxycarbonyl-7-(4-oxo-1-phenylidene)-1(7H)—indolizinone

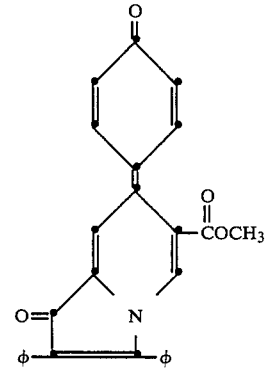

2,3-diphenyl-6-[2-methyl-2-(3-pyridyl)-propionyl-7-(4-oxo-1-phenylidene)]-1(7H)—indolizinone

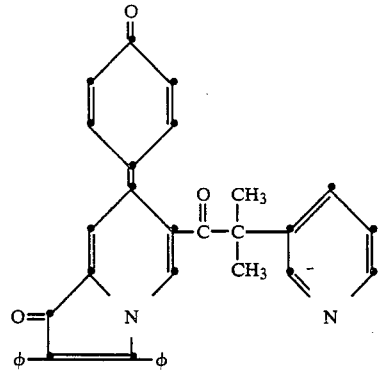

1,2-bis{6,6'-[2,3-diphenyl-7-(4-oxo-1-phenylidene)-1(7H)—indolizinone]/-3-

-continued methyl-1-oxopropane

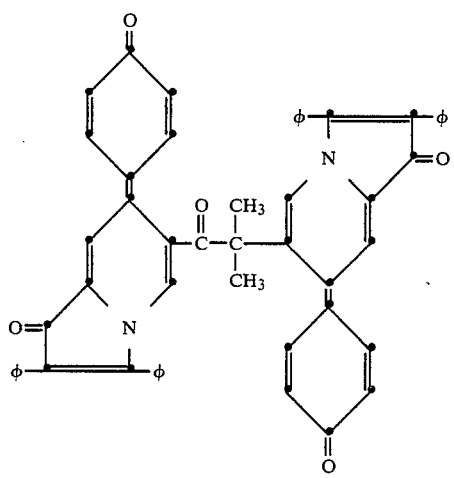

6-acetyl-2,3-diphenyl-7-(4-oxo-phenylidene)-1(7H)—indolizinone

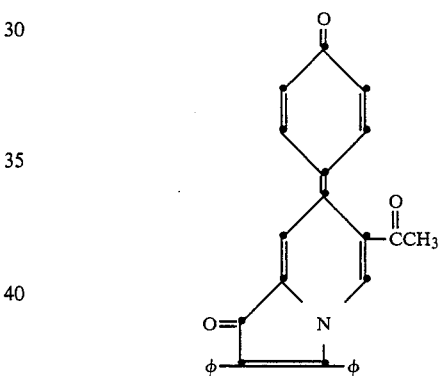

6-benzyl-1,2-diphenyl-7-(4-oxo-1-phenylidene)-3(7H)—indolizinone

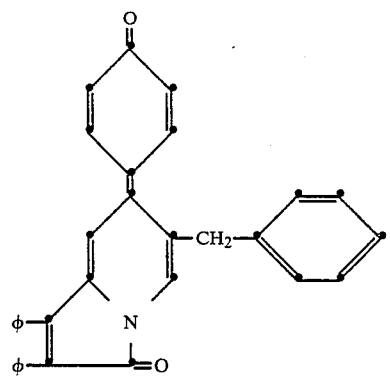

6-chloro-1,2-diphenyl-7-(4-oxo-1-phenylidene)-3(7H)—indolizinone

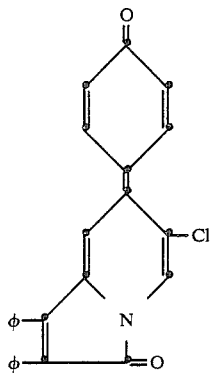

6-cyano-2,3-diphenyl-7-(4-oxo-1-phenyl-idene)-1(7H)—indolizinone

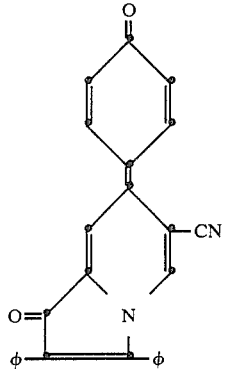

6-(4-azastyryl)-1,2-diphenyl-7-(4-oxo-1-phenylidene)-3(7H)—indolizinone

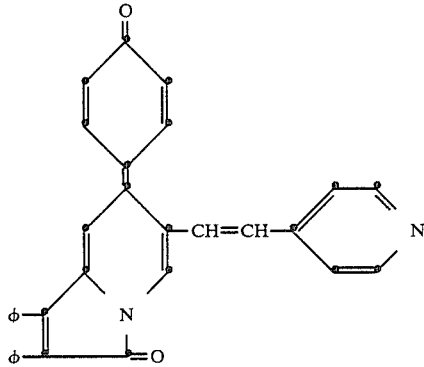

2,3-diphenyl-7-(2-hydroxy-4-oxo-3-pival-amido-1-phenylidene)-1(7H)—indolizinone

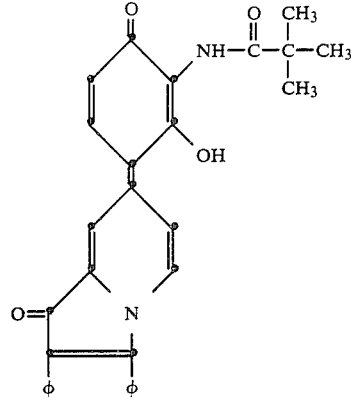

6-(4-azastyryl)-7-[3-(4-tert-butylbenz-amido)-2-hydroxy-4-oxo-1-phenylidene]-1,2-diphenyl-3(7H)—indolizinone

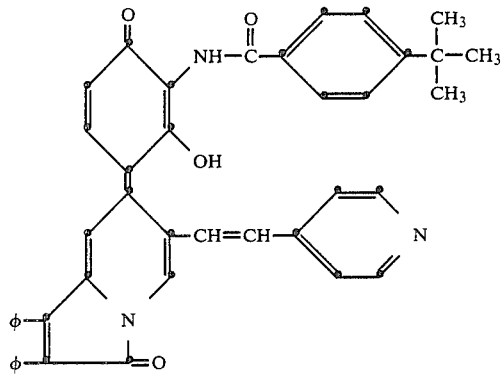

7-[3-(4-tert-butylbenzamido)-2-hydroxy-4-oxo-1-phenylidene]-1,2-diphenyl-6-(3-hydroxypropyl)-3(7H)—indolizinone

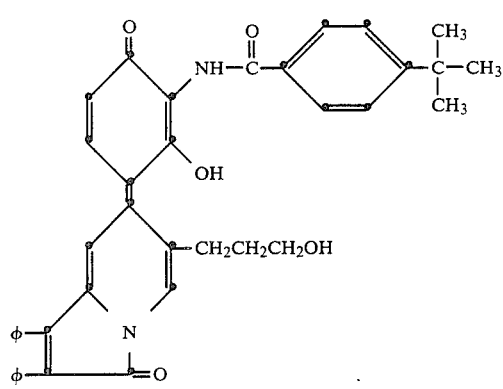

7-[3-(4-tert-butylbenzamido)-2-hydroxy-4-oxo-1-phenylidene]-6-carbomethoxy-2,3-diphenyl-1(7H)—indolizinone

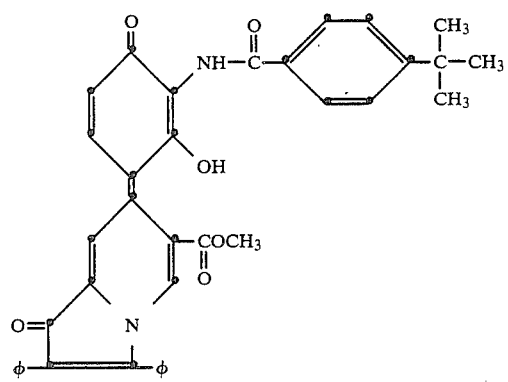

7-[3-(4-tert-butylbenzamido)-2-hydroxy-4-oxo-1-phenylidene]-2,3-diphenyl-6-methyl-carbamyl-1(7H)—indolizinone

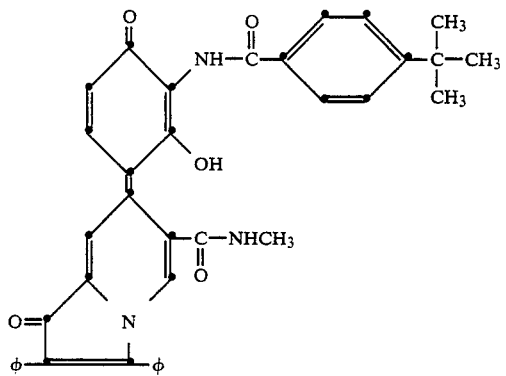

7-[3-(4-tert-butylbenzamido)-2-hydroxy-4-oxo-1-phenylidene]-1,2-diphenyl-6-methyl-3(7H)—indolizinone

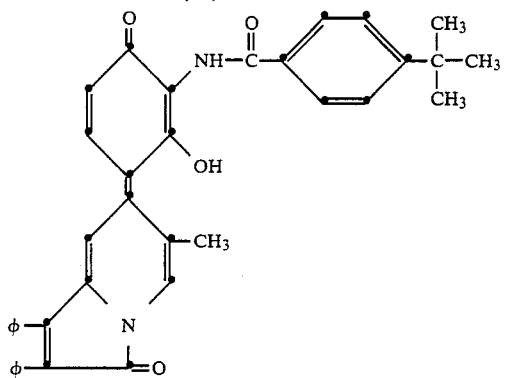

7-[3-(4-tert-butylbenzamido)-2-hydroxy-4-oxo-1-phenylidene]-6,8-dimethyl-1,2-diphenyl-3(7H)—indolizinone

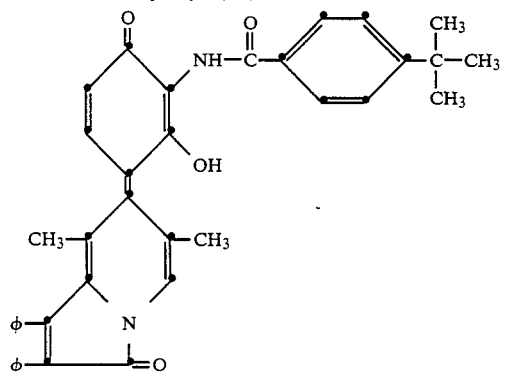

7-[3-(4-tert-butylbenzamido)-2-hydroxy-4-oxo-1-phenylidene]-6-diethylcarbamyl-2,3-diphenyl-1(7H)—indolizinone 6-benzyl-7-[3-(4-tert-butylbenzamido)-2-hydroxy-4-oxo-1-phenylidene]-1,2-diphenyl-3(7H)—indolizinone

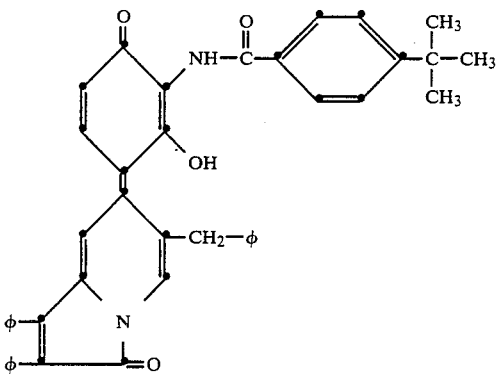

1,2-bis-{6,6'-{7-[3-(4-tert-butyl-benzamido)-2-hydroxy-4-oxo-1-phenyl-idene]}-2,3-diphenyl-1(7H)—indolizinonyl}-2-methyl-1-oxo-propane

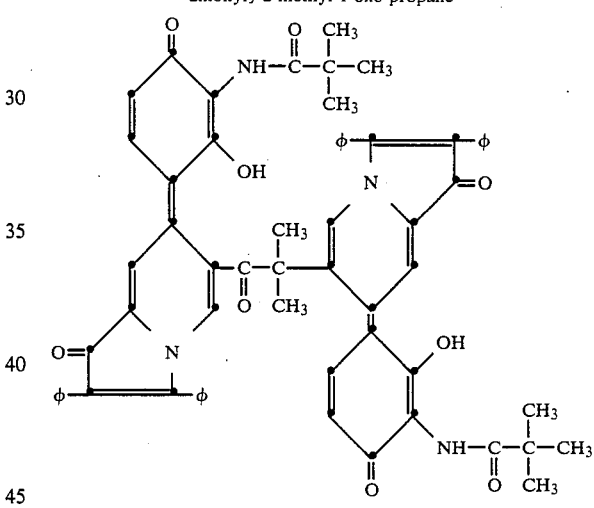

2,3-diphenyl-7-[3-(4-tert-butylbenzamido)-2-hydroxy-4-oxo-1-phenylidene]-1(7H)—indolizinone

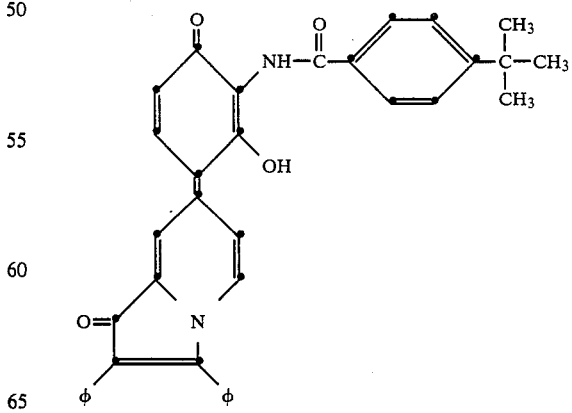

7-[3,5-di-tert-butyl-4-oxo-1-phenylidene]-1,2-di-(4-methoxyphenyl)-3(7H)—indolizinone -continued
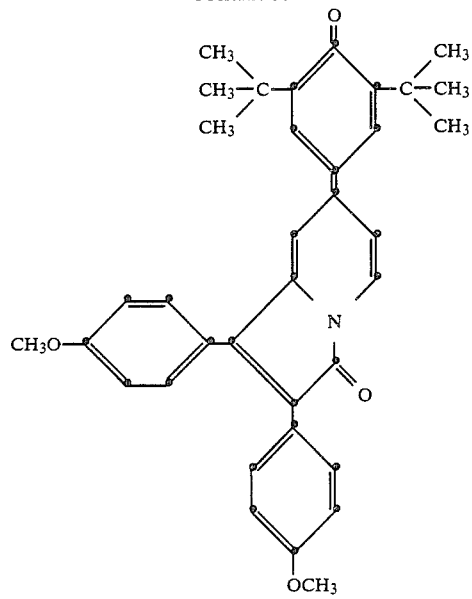
7-[3,5-di-tert-butyl-4-oxo-1-phenylidene]-
2,3-di-n-propyl-1(7H)—indolizinone
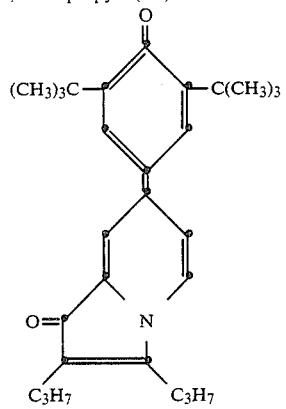
Further examples of oxoindolizine dyes prepared from phenolic couplers are listed below. Where available, γmax values, in nanometers (nm), are reported in parentheses:
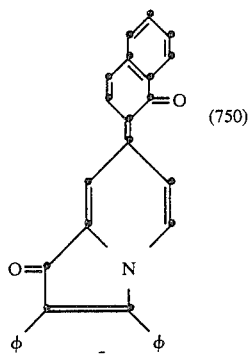
(750)
-continued
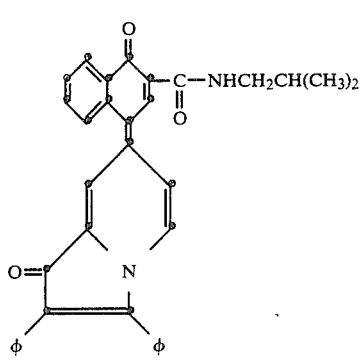
(750)
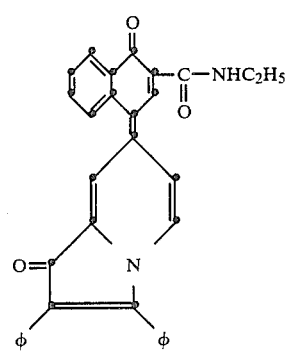
(750)
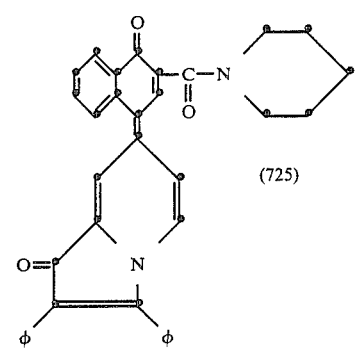
(725)
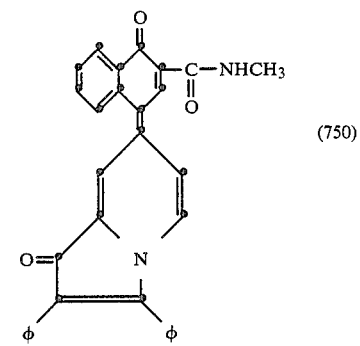
(750)

-continued
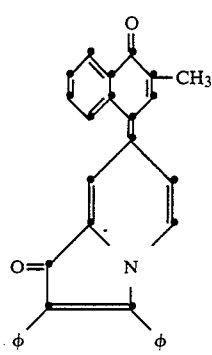 (703)
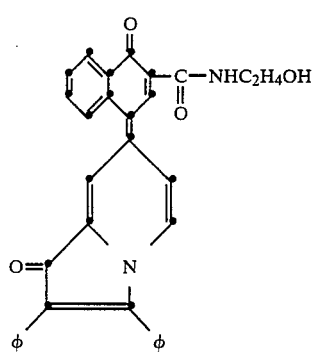 (745)
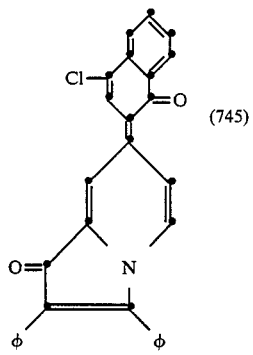 (745)
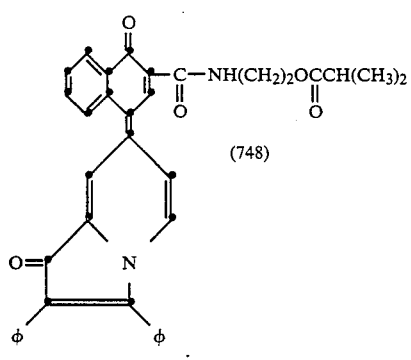 (748)
-continued
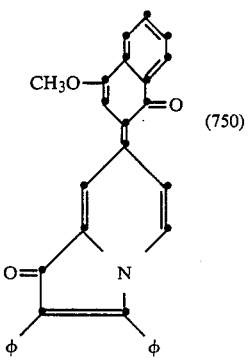 (750)
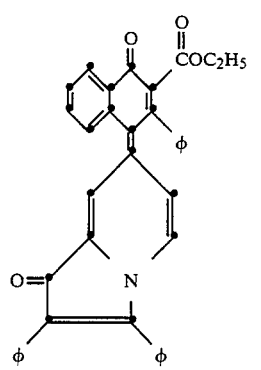 (755)
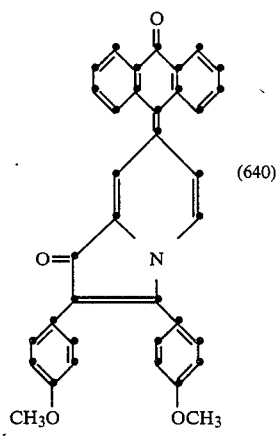 (640)
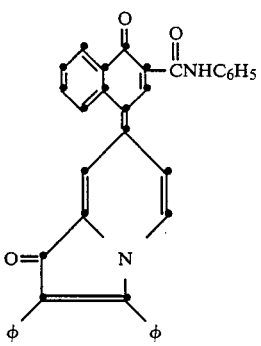 (768)

-continued
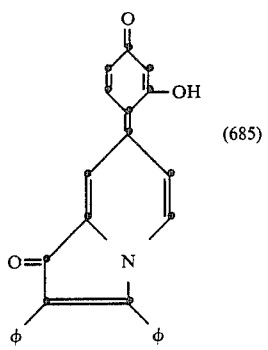
(685)
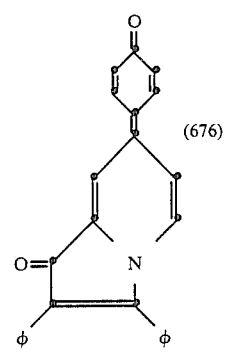
(676)
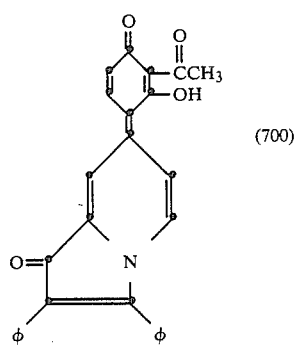
(700)
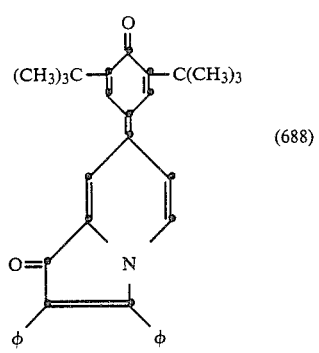
(688)
-continued
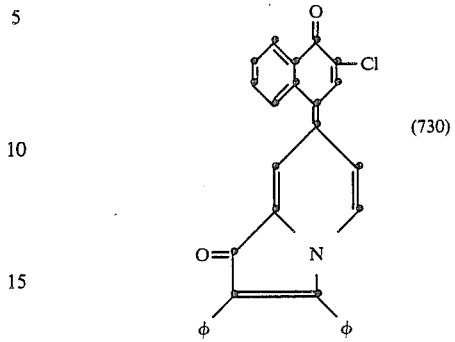
(730)
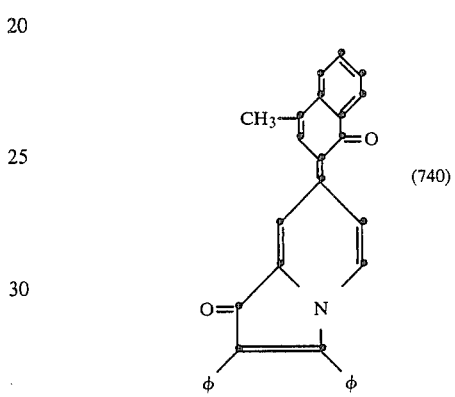
(740)
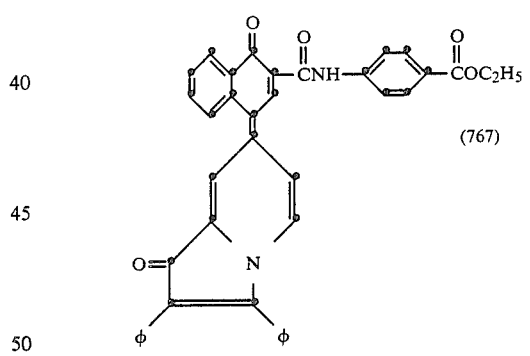
(767)
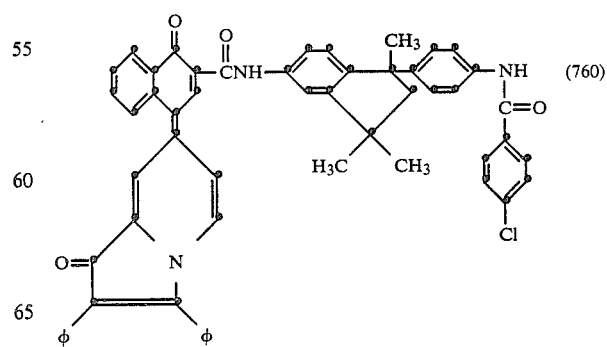
(760)

-continued
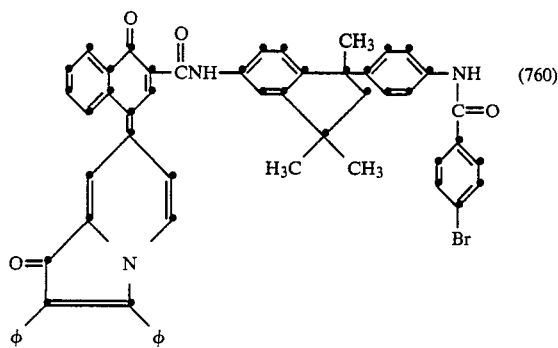 (760)
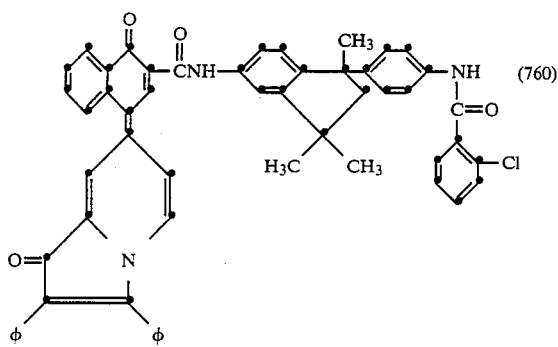 (760)
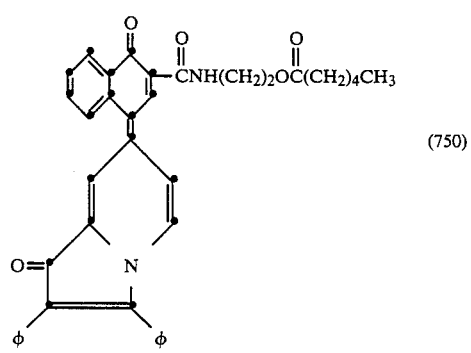 (750)
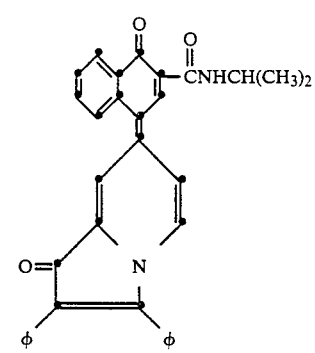 (750)
-continued
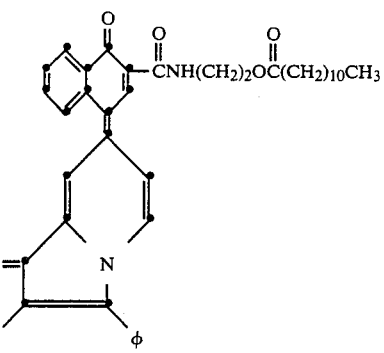 (750)
Oxoindolizinium dyes according to the invention are also formed from reaction of an aniline coupler with an oxoindolizine compound. Examples of such indolizinium dyes formed from aniline couplers are represented by the formulas:
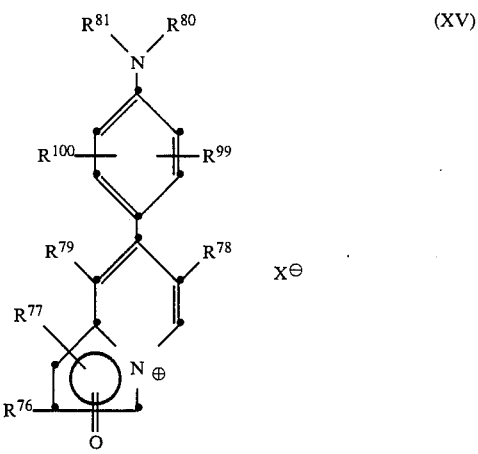 (XV)
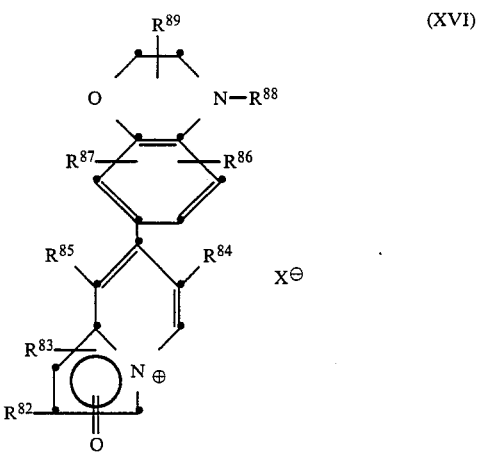 (XVI)
and -continued

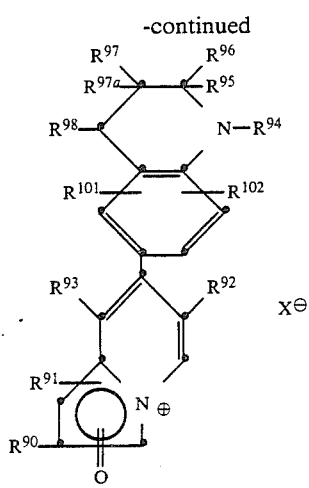

(XVII)

wherein $R^{76}$, $R^{77}$, $R^{82}$, $R^{83}$, $R^{90}$ and $R^{91}$ are individually aryl containing 6 to 14 carbon atoms, such as phenyl, naphthyl, anthryl, methoxyphenyl and methoxynaphthyl; aralkenyl containing 6 to 14 carbon atoms, such as 2,2-diphenylvinyl, 2-phenylvinyl, 2-naphthylvinyl and 2-methyl-(2-phenylvinyl); alkyl containing 1 to 18 carbon atoms, such as methyl, ethyl, propyl, decyl and eicosyl; or $R^{76}$ and $R^{77}$, $R^{82}$ and $R^{83}$, $R^{90}$ and $R^{91}$ together represent the carbon atoms necessary to complete a cyclic structure, such as 2,3-pentamethylene;

$R^{78}$, $R^{84}$ and $R^{92}$ are individually hydrogen, alkyl containing 1 to 18 carbon atoms, such as methyl, ethyl, and dodecyl; cyano; acyl containing 2 to 18 carbon atoms, such as acetyl, propionyl, 2-ethylhexanoyl and stearoyl; carboalkoxy containing 1 to 18 carbon atoms such as carbomethoxy, carboethoxy and carbobutoxy; aminocarbonyl, methylaminocarbonyl, dimethylaminocarbonyl and ethylaminocarbonyl; acyloxy containing 2 to 18 carbon atoms, such as acetoxy, propionoxy, butyroxy and lauroyloxy; bromine and chlorine;

$R^{79}$, $R^{85}$ and $R^{93}$ are individually hydrogen; chlorine; bromine; or, alkyl containing 1 to 18 carbon atoms, such as methyl, ethyl, propyl and dodecyl;

$R^{80}$, $R^{81}$, $R^{88}$ and $R^{94}$ are individually hydrogen or substituents that do not adversely affect the desired indolizinium dye, such as alkyl containing 1 to 20 carbon atoms, such as methyl, ethyl, propyl, decyl, and eicosyl; cycloalkyl, such as cycloalkyl containing 6 to 20 carbon atoms; straight or branched chain alkenyl containing 2 to 10 carbon atoms; or $R^{80}$ and $R^{81}$ together represent the atoms necessary to complete a 5- or 6-member heterocyclic ring with the nitrogen atom to which they are bonded, such as atoms completing a pentamethylene, ethyleneoxyethylene or ethylenesulfonylethylene group which forms a ring, or a julolidyl group;

$R^{99}$, $R^{100}$, $R^{86}$, $R^{87}$, $R^{101}$ and $R^{102}$ are individually hydrogen; fluorine; chlorine; bromine; alkyl containing 1 to 6 carbon atoms; cycloalkyl containing 5 to 12 carbon atoms; alkoxy containing 1 to 4 carbon atoms; phenoxy; alkylthio, such as alkylthio containing 1 to 4 carbon atoms; arylthio, such as arylthio containing 6 to 20 carbon atoms; and groups represented by the formula $-NH-XR^{36}$ in which X is $-CO-$, $-COO-$ or $-SO_2-$, wherein $R^{36}$ is as defined above; and $R^{89}$, $R^{95}$, $R^{96}$, $R^{97}$, $R^{97a}$ and $R^{98}$ are individually hydrogen and alkyl containing 1 to 6 carbon atoms; and $X^{\ominus}$ is an anion as defined above, such as $CF_3SO_3^{\ominus}$, $BF_4^{\ominus}$ and $BR^{\ominus}$.

Examples of related oxoindolizinium and oxoindolizine dyes are:

7-(2-N,N—diethylamino-1-ethenyl)-2,3-di-(4-methoxyphenyl)-1-oxoindolizinium fluoborate

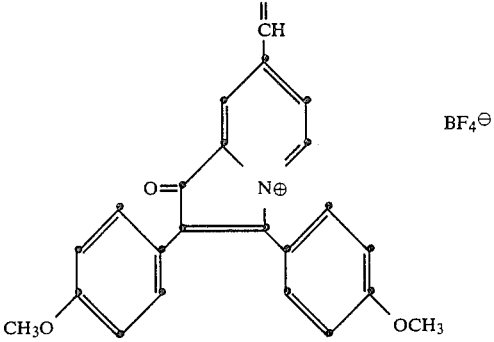

(610)

7-(2-N,N—diethylamino-1-ethenyl)-1,2-phenyl-3-oxoindolizinium iodide

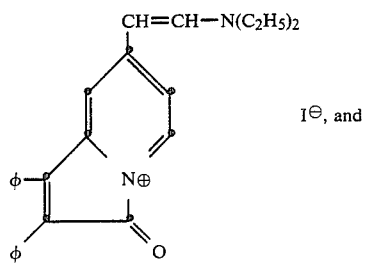

2,3-di-(4-methoxyphenyl)-7-dimethylamino-1-oxoindolizinium-iodide

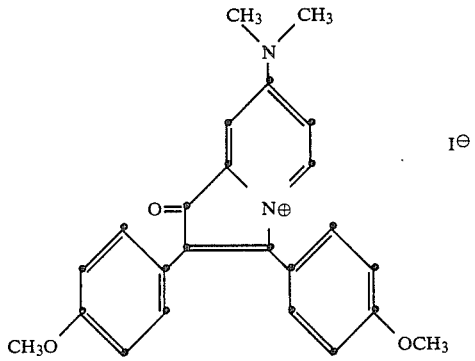

Further examples of oxoindolizinium dyes prepared from aniline-type couplers are listed below. Where available, λmax values, in nanometers (nm), are reported in parentheses. In instances where two λmax values are reported, both value intensities are approximately equal.

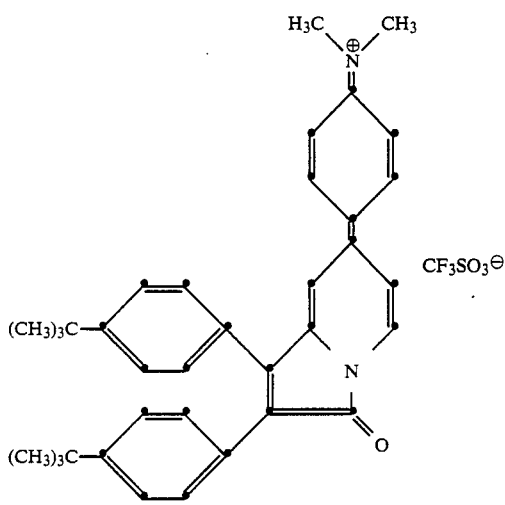
(755)
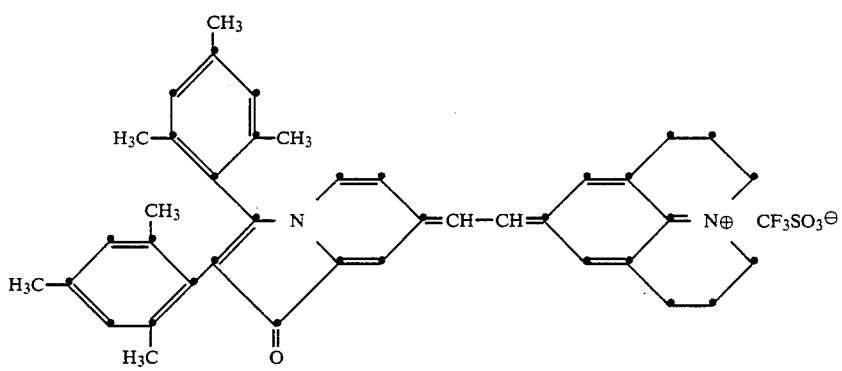
(840)
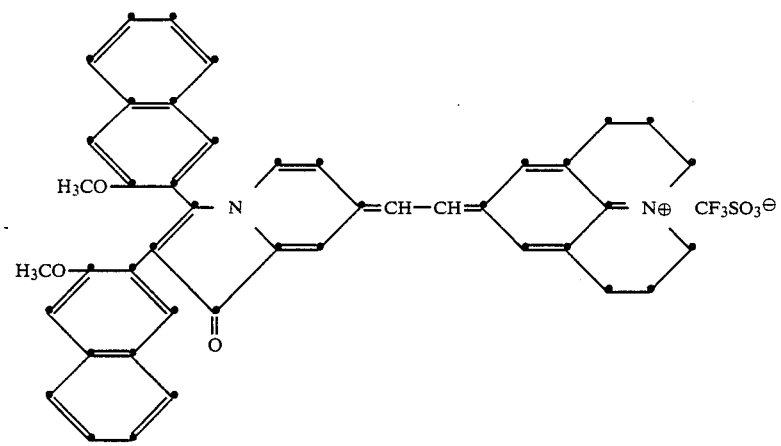
(830)
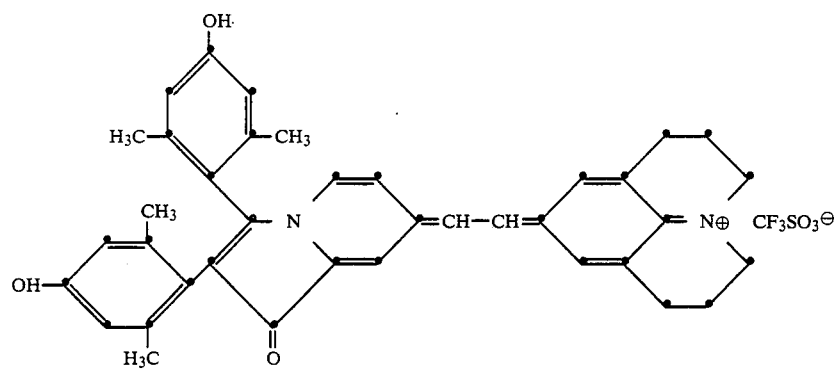
(835)

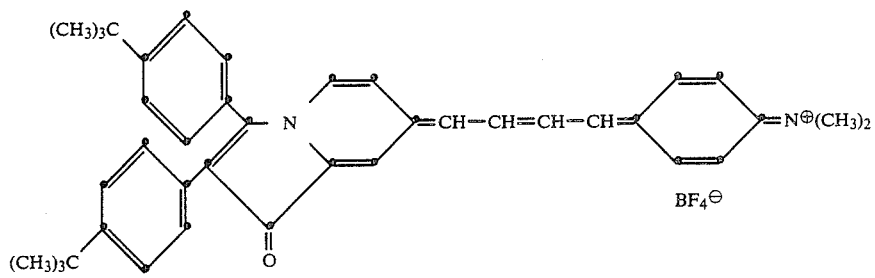
(870)
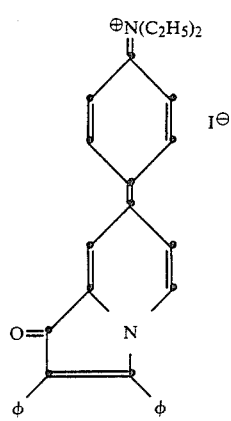
(680)
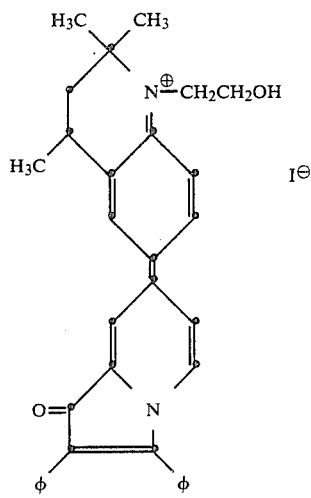
(750)
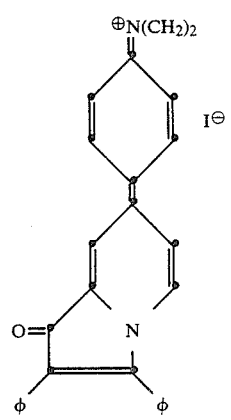
(680)
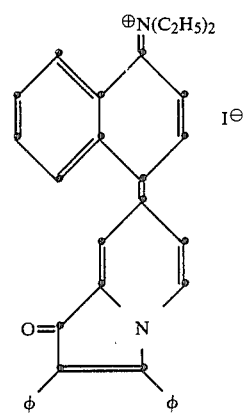
(660)
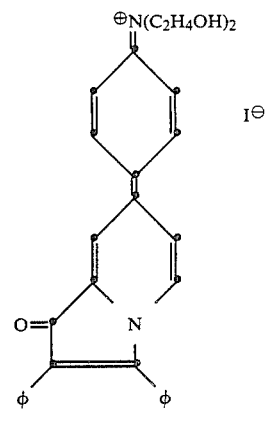
(735)
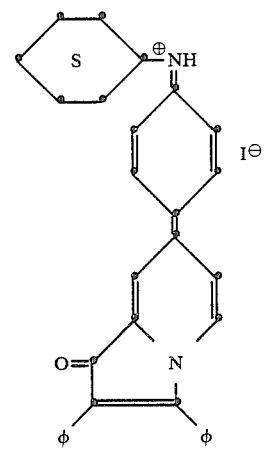
(720)

(710) 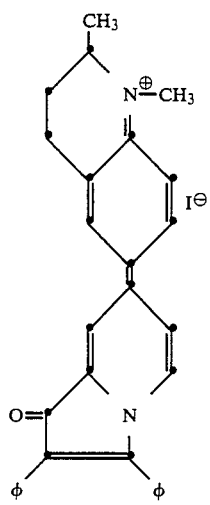

(730, 790) 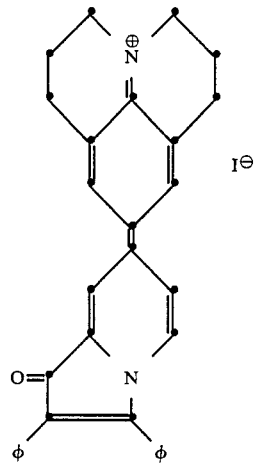

(700) 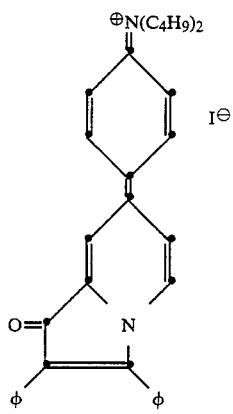

(690) 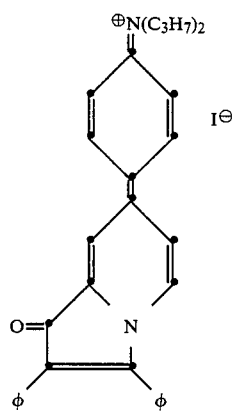

(640) 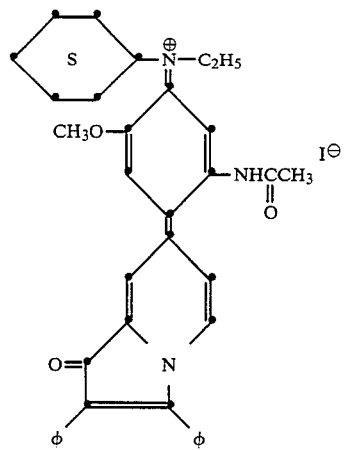

Many useful oxoindolizine dyes according to the invention are formed from the reaction of an active methylene coupler with a suitable oxoindolizine compound. Especially useful oxoindolizines are dyes formed from the reaction of ketomethylene couplers, methylpyrylium couplers and methylindolizinium couplers with appropriate oxoindolizine compounds. Examples of useful indolizinone dyes formed from active methylene couplers are represented by the formula:

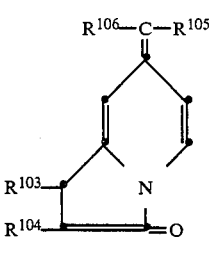

and (XVIII)

-continued

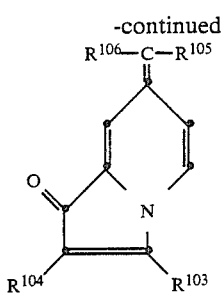
(XVIIIA)

wherein:

R$^{103}$ and R$^{104}$ are individually aryl containing 6 to 20 carbon atoms, such as phenyl, naphthyl, anthryl, methoxyphenyl and methoxynaphthyl; aralkenyl containing 6 to 14 carbon atoms, such as 2,2-diphenylvinyl, 2-phenylvinyl, 2-naphthylvinyl and 2-methyl-(2-phenylvinyl); alkyl containing 1 to 20 carbon atoms, such as methyl, ethyl, propyl, decyl and eicosyl; or R$^{103}$ and R$^{104}$ together represent the carbon atoms necessary to complete a cyclic structure, such as 2,3-pentamethylene;

R$^{105}$ and R$^{106}$ are individually electronegative groups, such as aryl containing 6 to 20 carbon atoms, such as phenyl and naphthyl; cyano; acyl containing 2 to 18 carbon atoms, such as acetyl, propionyl and butyryl; carboalkoxy containing 2 to 18 carbon atoms, such as carbomethoxy, carboamyloxy and carbobutoxy; aminocarbonyl containing 1 to 18 carbon atoms such as unsubstituted aminocarbonyl, methylaminocarbonyl, dimethylaminocarbonyl and ethylaminocarbonyl; and R$^{105}$ is alternatively hydrogen.

Examples of oxoindolizine dyes formed from active methylene couplers are as follows:

7-(diacetylmethylidene)-1,2-diphenyl-3-(7H)—indolizinone

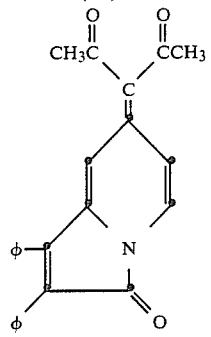
(410, 480)

7-(dibenzoylmethylidene)-2,3-diphenyl-1-(7H)—indolizinone

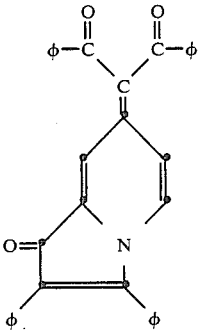
(610)

7-(anilinocarbonyl benzoylmethylidene)-2,3-diphenyl-1(7H)—indolizinone

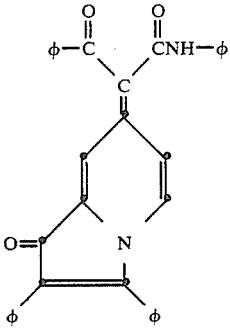

6-cyano-7-(diacetylmethylidene)-2,3-diphenyl-1(7H)—indolizinone

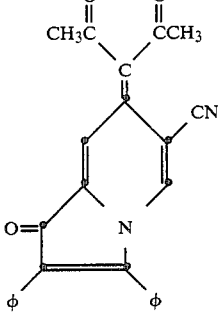
(530)

7-(dicyanomethylidene)-2,3-diphenyl-1(7H)—indolizinone

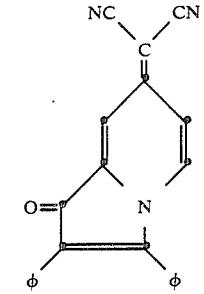
(550, 590)

7-(1-cyano-1-phenylmethylidene)-1,2-diphenyl-3(7H)—indolizinone

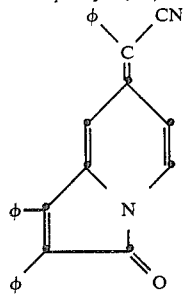

7-(1-aminocarbonyl-1-phenylmethylidene)-2,3-diphenyl-1(7H)—indolizinone 7-(dicarboethoxymethylidene)-2,3-diphenyl-1(7H)—indolizinone

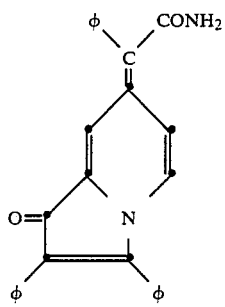
2,3-diphenyl-7-(2,2-dimethyl-4,6-dioxo-1,3-dioxanylidene)-1(7H)—indolizinone
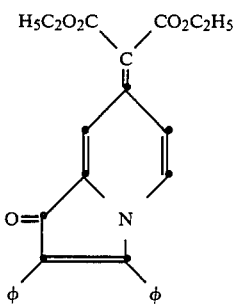
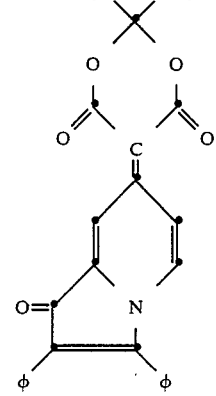 (560, 580)
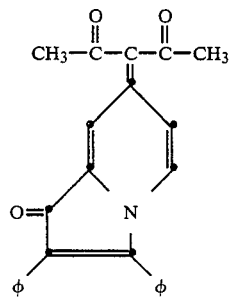 (599)
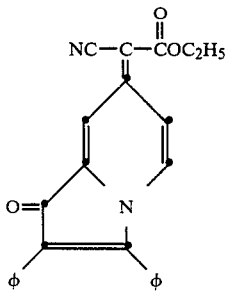 (553, 590)
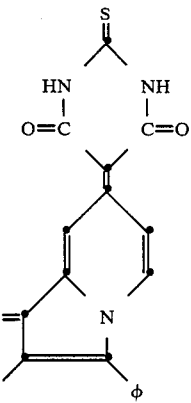 (580)
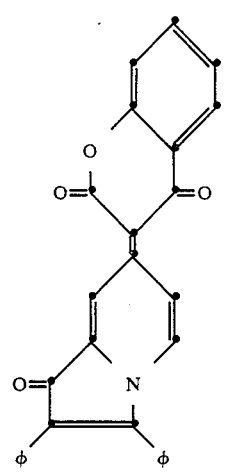 (590)
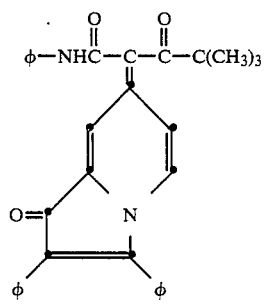 (570)

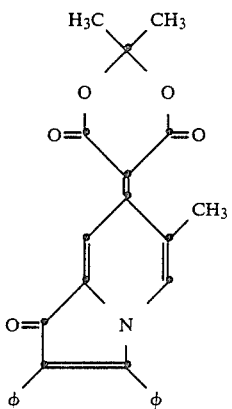 (600)
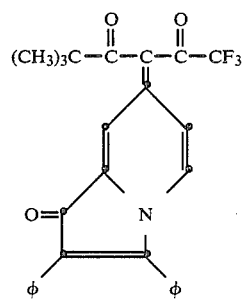 (570, 603)
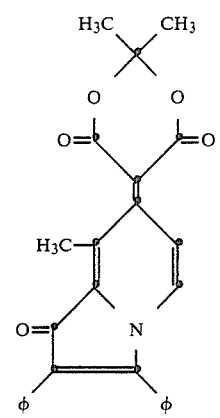 (600)
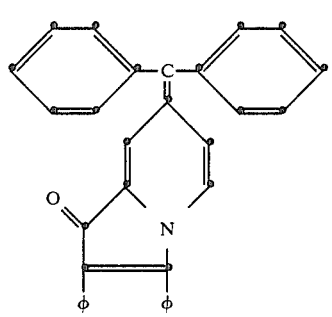 (600)
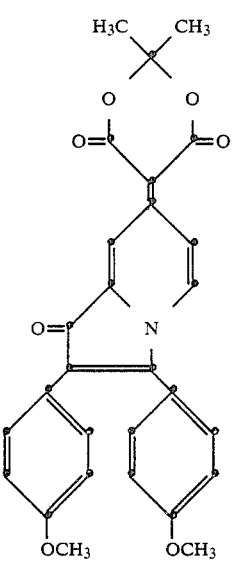 (570)
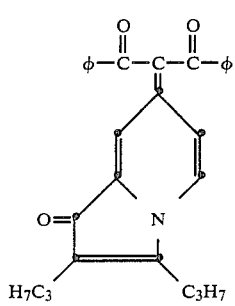 (553, 590)

-continued
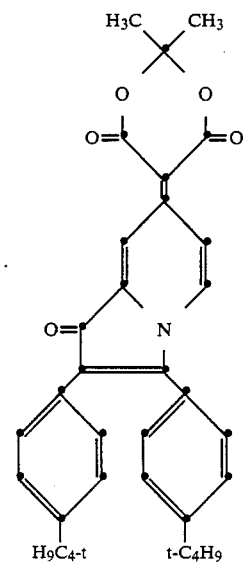
(563)
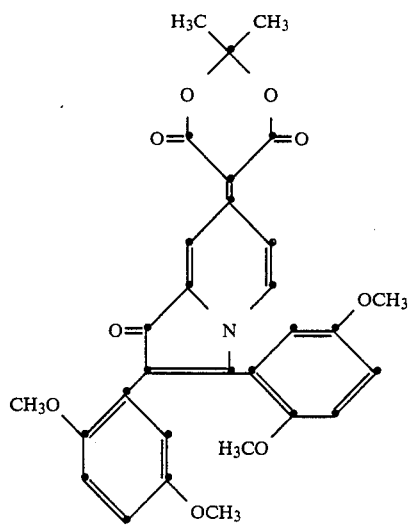
(560)
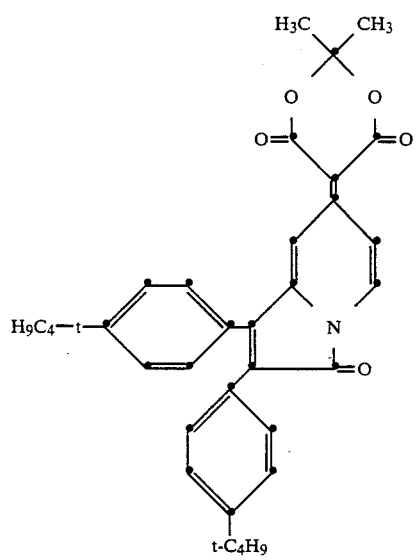
(460)
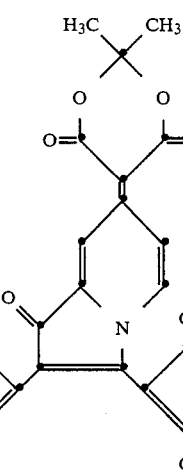
(540)
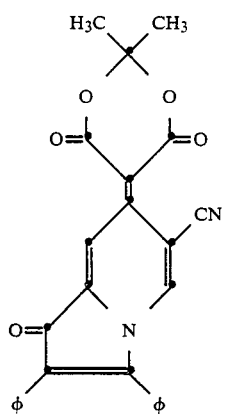
(540)
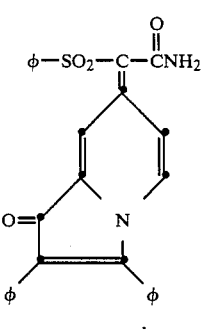
(570)

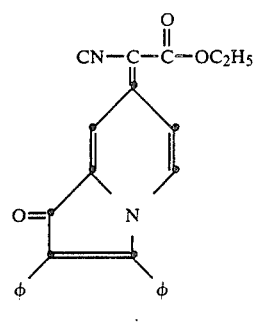 (560)
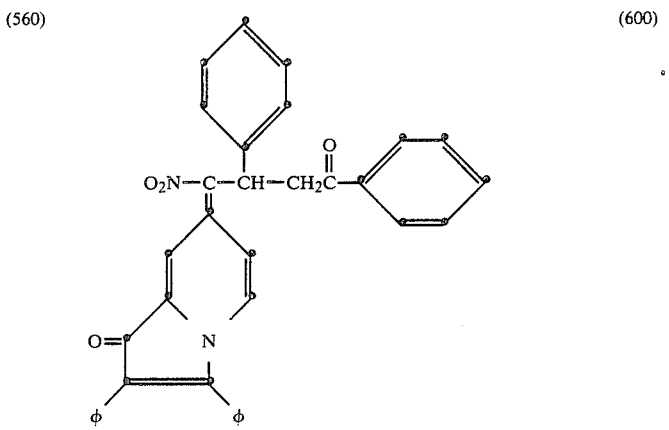 (600)
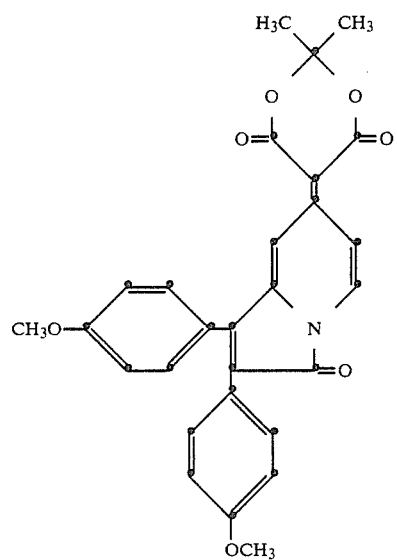 (440)
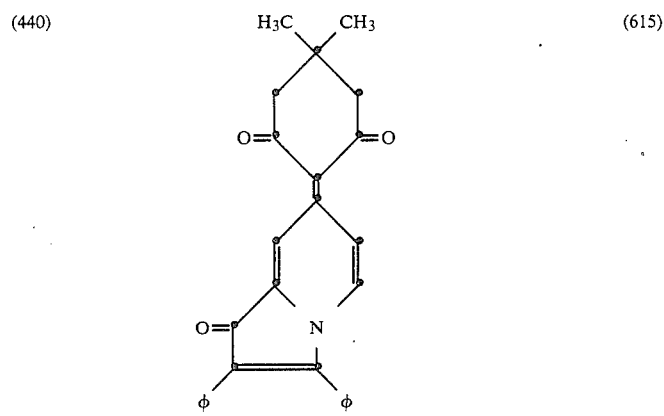 (615)
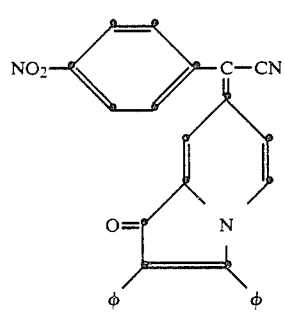 (640)
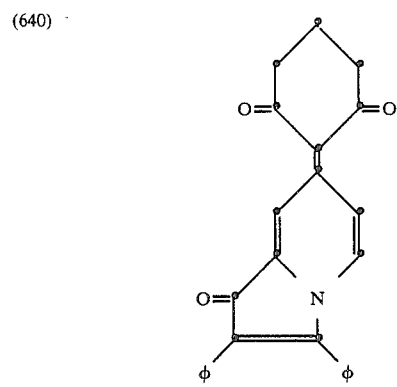 (615)

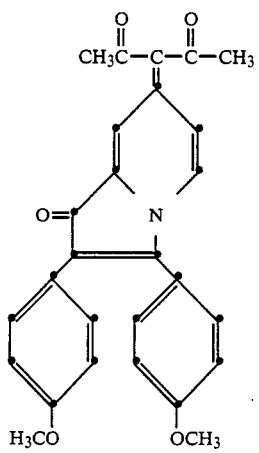 (600)
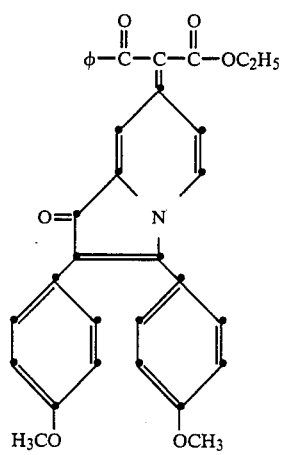 (590)
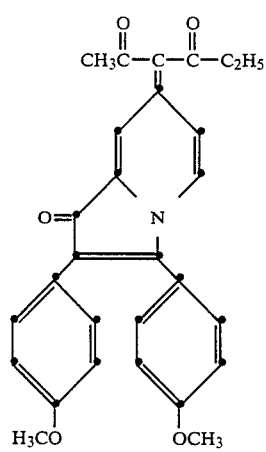 (590)
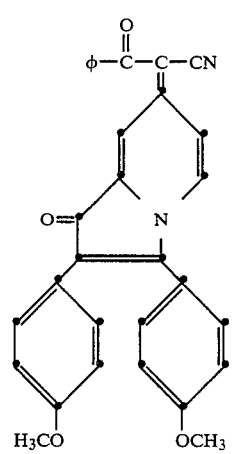 (600)
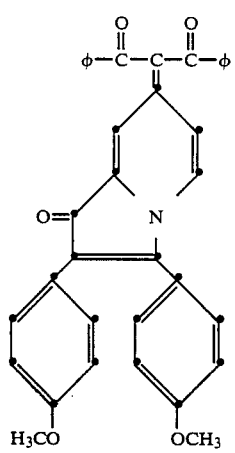 (610)
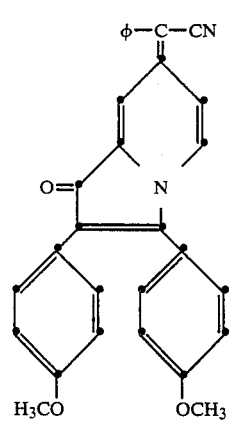 (610)

-continued
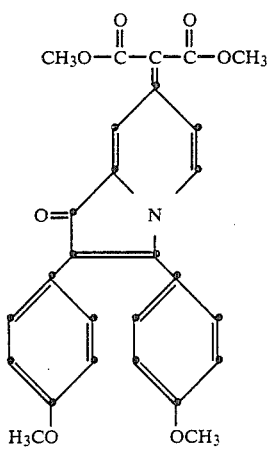 (580)
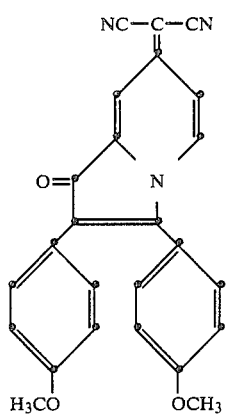 (585)
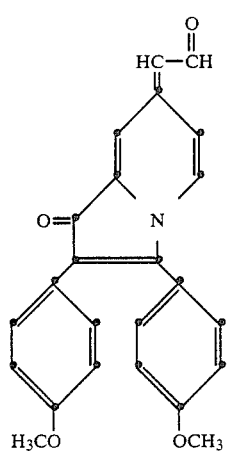 (595)
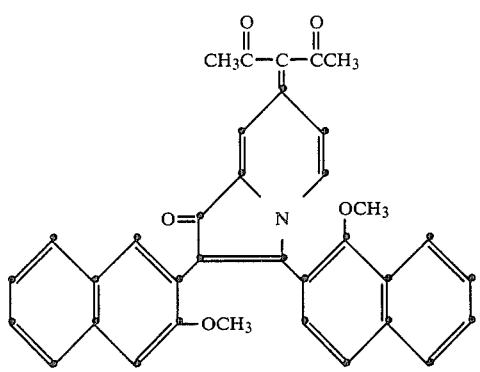 (566, 600)
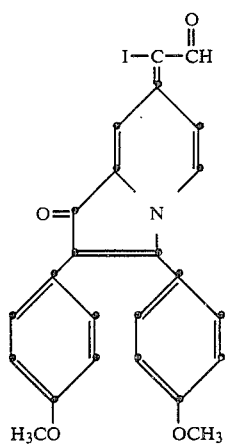 (610)
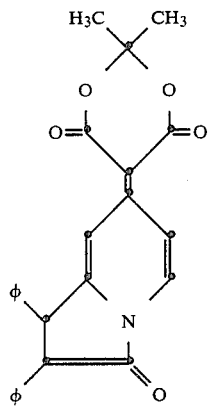 (445)

-continued
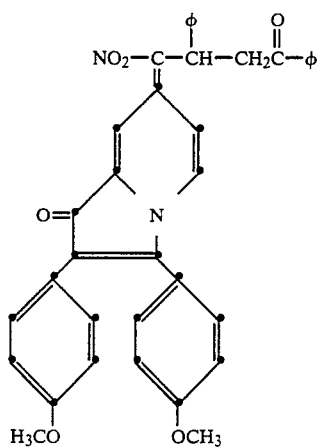 (610)
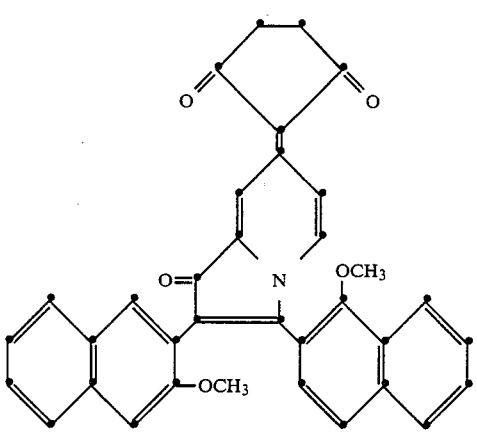 (565, 605)
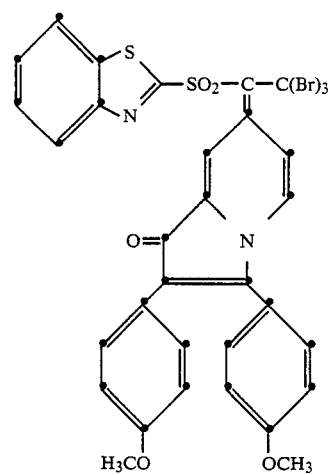
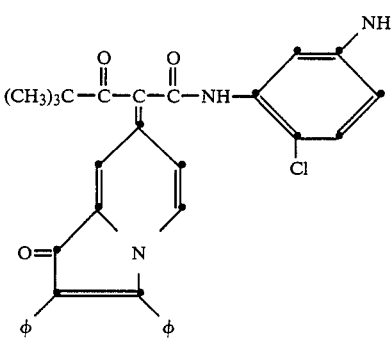 (605)
(580)
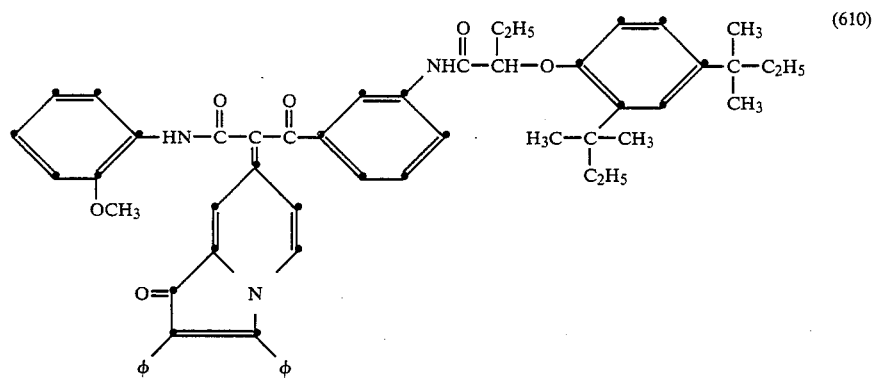 (610)

Examples of oxoindolizinium dyes formed from active methylene couplers are represented by the formula:

(XIX)

wherein
X$^\ominus$ is an anion as defined above;
R$^{108}$ and R$^{109}$ are individually the same as R$^{103}$ and R$^{104}$; and
Z represents the atoms necessary to complete a chromophore, such as the carbon, hydrogen, oxygen and nitrogen atoms necessary to complete a heterocyclic group, such as a pyranylidene, indolizinylidene, thiopyranylidene, selenopyranylidene, coumarinylidene, or pyrazolinonylidene group.

Examples of oxoindolizinium dyes formed from such active methylene couplers are as follows:

2,3-diphenyl-7-[(2,6-diphenyl-4-pyranylidene)methyl]-1-oxoindolizinium perchlorate
(615)

2,3-diphenyl-7-[(2,3-diphenyl-7-1(7H)—indolizinonylidene)methyl]-1-indolizinonium trifluoromethane sulfonate
(695)

2,3-diphenyl-7-[(2,6-diphenyl-4-thiopyranylidene)methyl]-1-indolizinonium trifluoromethane sulfonate
(780)

-continued

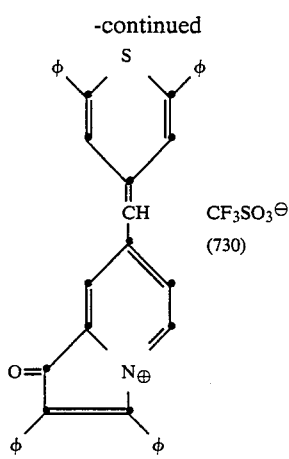
CF₃SO₃⁻
(730)

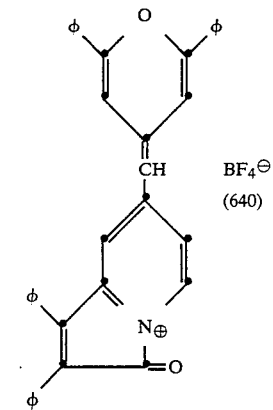
BF₄⁻
(640)

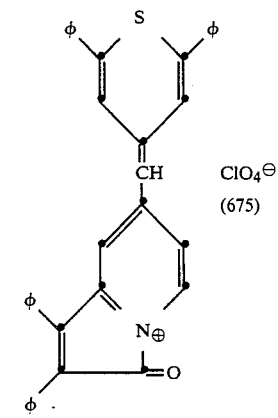
ClO₄⁻
(675)

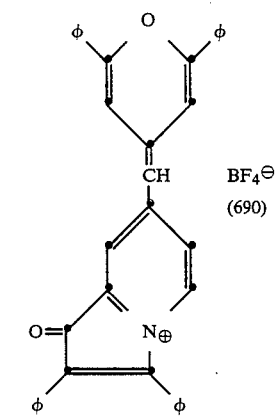
BF₄⁻
(690)

-continued

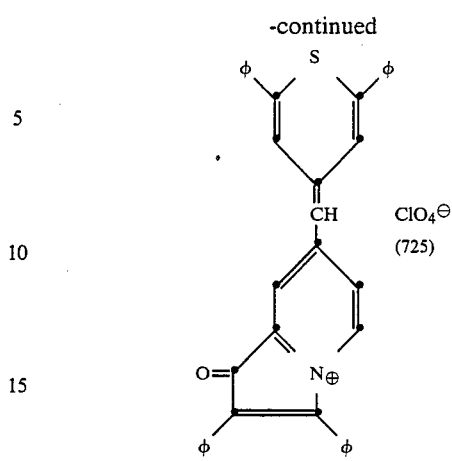
ClO₄⁻
(725)

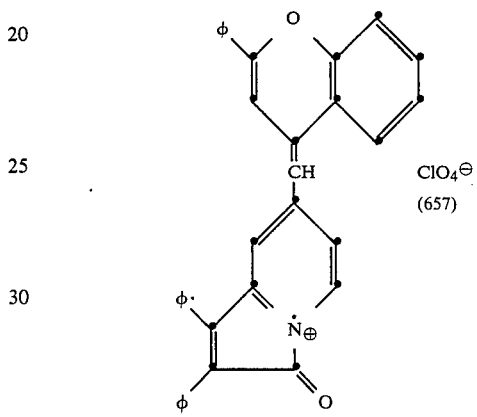
ClO₄⁻
(657)

Another class of oxoindolizine dyes according to the invention is represented by the formula:

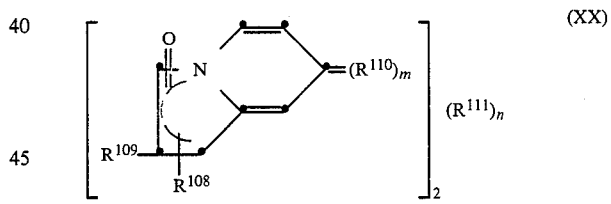
(XX)

wherein:

$R^{109}$ and $R^{109}$ are individually aryl containing 6 to 14 carbon atoms, such as phenyl, naphthyl and anthryl; or, alkyl containing 1 to 20 carbon atoms, such as methyl, ethyl, butyl and eicosyl;

$R^{110}$ is CH, phenylene or naphthylene;

$R^{111}$ is phenylene or naphthylene; and n and m are individually 0 or 1.

In oxoindolizine dyes according to the formula containing $R^{110}$ and $R^{108}$, the oxoindolizine moiety represents a group completing an organic chromophore to produce the desired dye. Examples of such compounds are:

2,3-diphenyl-7-[(2,6-diphenyl-4-pyranylidene)methyl]-1-oxoindolizinium perchlorate -continued

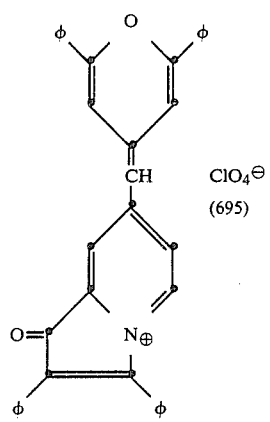
(695)

2,3-diphenyl-7-[(2,3-diphenyl-7-1(7H)—indolizinonylidene)methyl]-1-indolizinonium trifluoromethane sulfonate

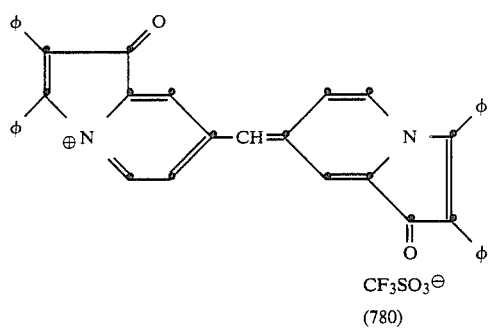
(780)

1,2-bis[7-(1,2-diphenyl-3(7H)—indolizinonylidene)]ethane

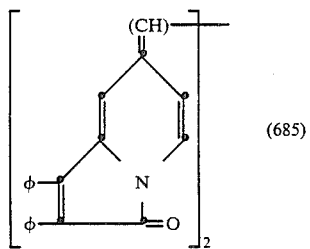
(685)

1,4-bis[7-(1,2-diphenyl-3(7H)—indolizinonylidene)]-2,5-cyclohexadiene

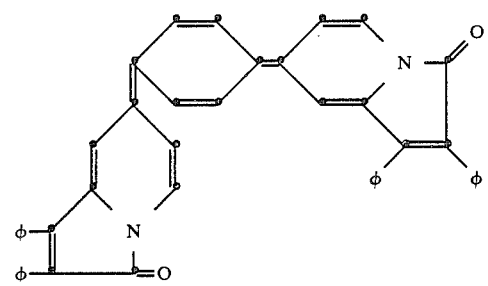

1,4-bis[7-(1,2-diphenyl-3(7H)—indolizinonylidene)]-2,3-Benzo-2,5-cyclohexadiene

-continued

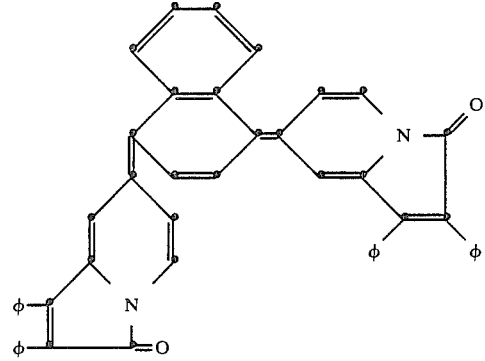

7,7'-bis[1,2-di-n-propyl-3(7H)—indolizonylidene]

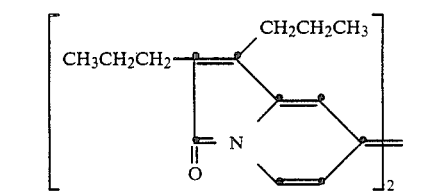

7,7'-bis-[1,2-pentamethylene-3(7H)—indolizonylidene]

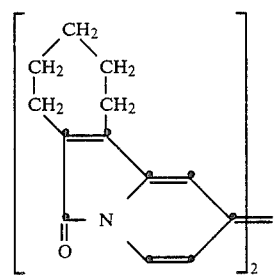

1,2-bis-[2,3-di-(4-methoxyphenyl)-1(7H)—indolizinonylidene]ethane

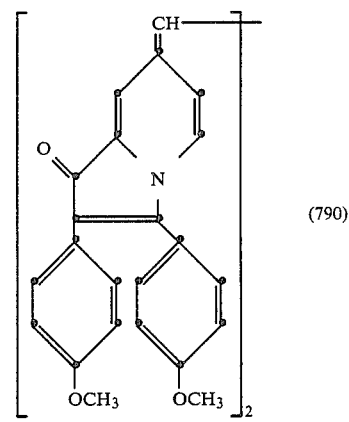
(790)

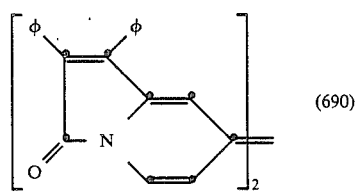
(690)

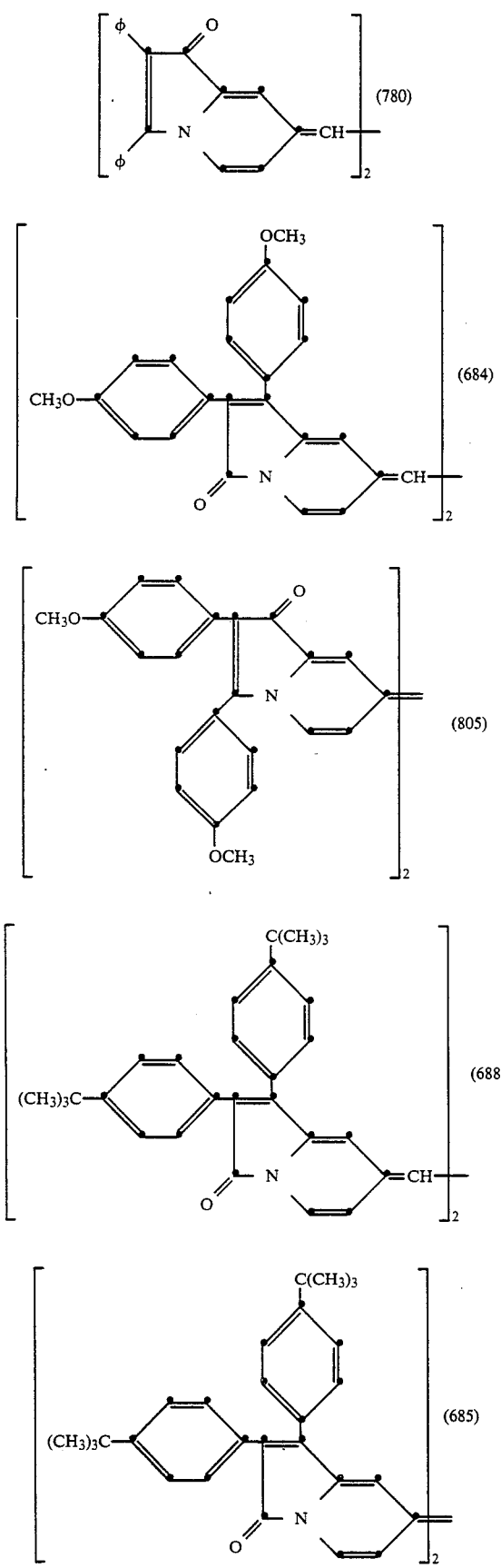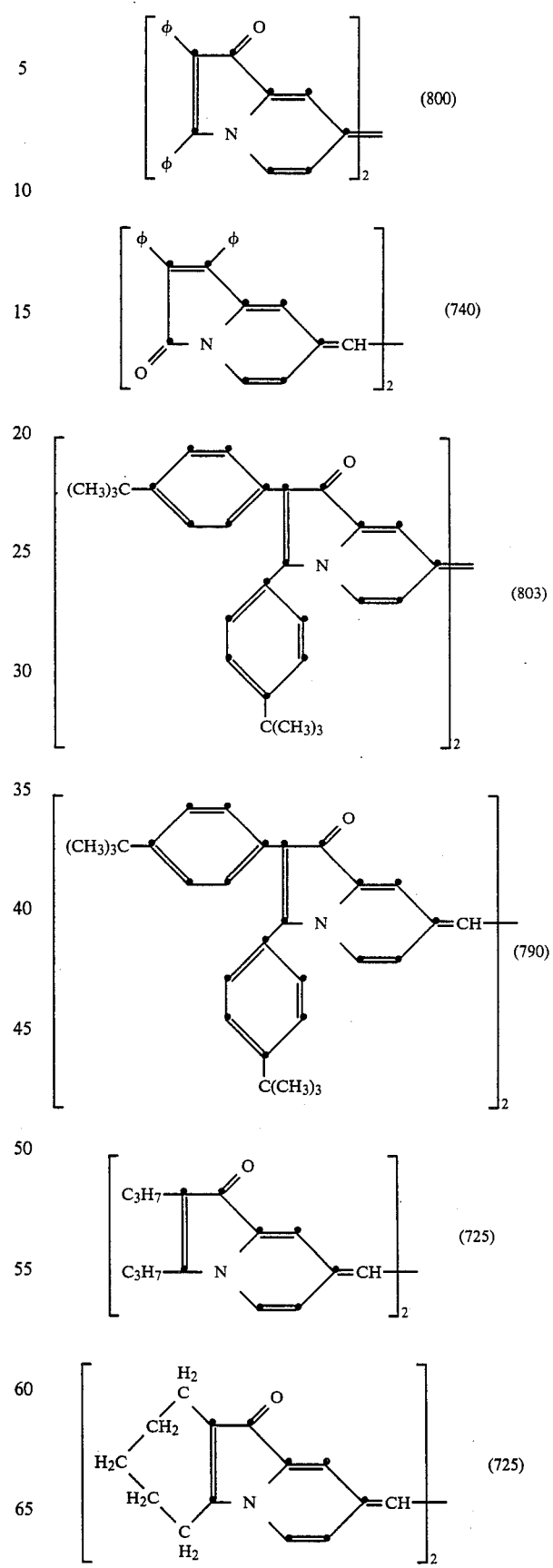

-continued
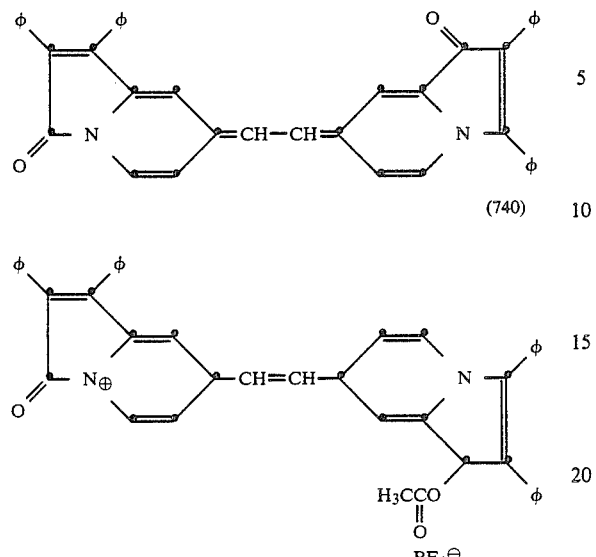
(740)
(840)
Examples of other dyes within the above structures (I) and (II) are as follows:
N—benzyl-4-{7-[2,3-di(4-methoxyphenyl)-3-indolizinolyl]}pyridinium bromide
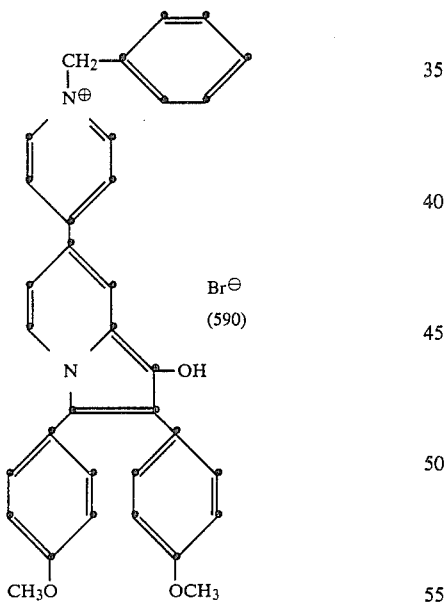
(590)
7-[4-(N—benzylpyridylidene)]-2,3-diphenyl-1-hydroxy indolizinium chloride
-continued
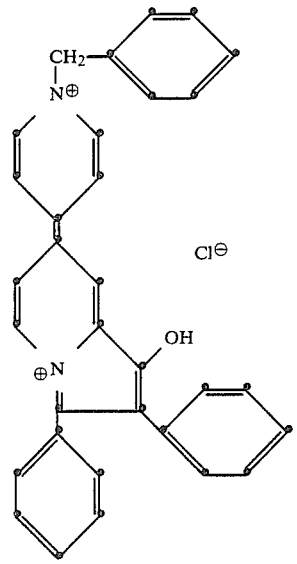
7-[4-(N—benzylpyridylidene)]-2,3-diphenyl-1-indolizinone
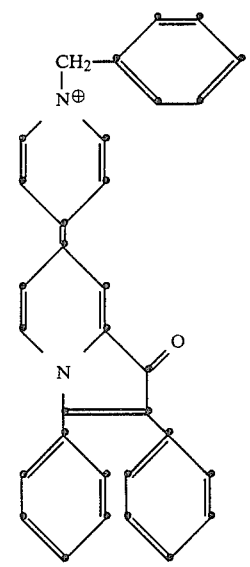
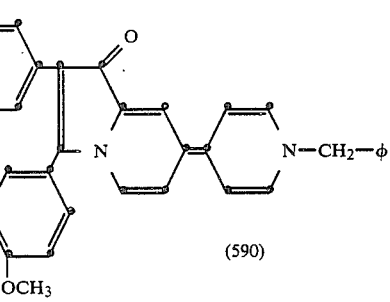
(590)

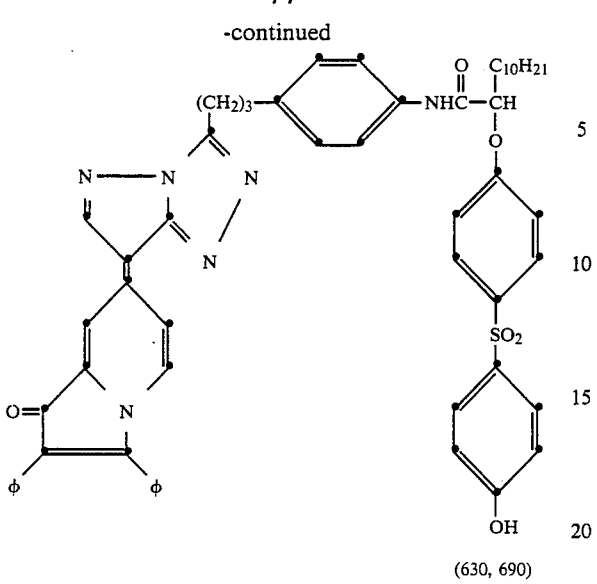

(630, 690)

Another illustrative class of dye according to the invention is represented by the formula:

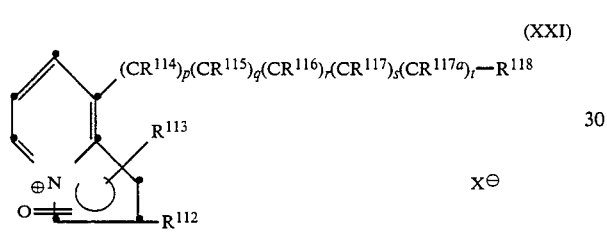

(XXI)

wherein

X$^{\ominus}$ is an anion as defined above, preferably an acid anion such as methanesulfonate, trifluoromethanesulfonate, para-toluenesulfonate, BF$_4^{\ominus}$, bromide, chloride, iodide and sulfinate;

$R^{112}$ and $R^{113}$ are individually aryl containing 6 to 14 carbon atoms, such as phenyl, naphthyl, anthryl, methoxyphenyl and methoxynaphthyl; aralkenyl containing 6 to 14 carbon atoms, such as 2,2-diphenylvinyl, 2-phenylvinyl, 2-naphthylvinyl, and 2-methyl-(2-phenylvinyl); and alkyl containing 1 to 20 carbon atoms, such as methyl, ethyl, propyl, decyl and eicosyl; or $R^{112}$ and $R^{113}$ together represent the carbon atoms necessary to complete a cyclic structure, such as 2,3-pentamethylene;

$R^{114}$, $R^{115}$, $R^{116}$ $R^{117}$ and $R^{117a}$ are individually hydrogen; alkyl containing 1 to 18 carbon atoms, such as methyl, ethyl, propyl, decyl and eicosyl; phenyl; cyano; carboxy; carboxamide; and, carboalkoxy, such as carboalkoxy containing 2 to 18 carbon atoms; at least one of $R^{114}$, $R^{115}$, $R^{116}$, $R^{117}$ and $R^{117a}$ is hydrogen;

$R^{118}$ is an electropositive or an electronegative group necessary to complete a chromophore, such as amino, anilino, nitrophenyl, quino, pyranyl, pyridyl, indolizinyl, julolidyl thiopyranyl and

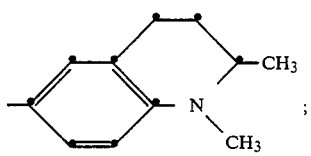

p, q, r s and t are individually 0 or 1; any free bonds being satisfied by hydrogen or unsaturated bonding as required.

Examples of compounds within this class are as follows:

7-[2-(4-N,N—dimethylaminophenyl-1-ethenyl]-2,3-diphenyl-1-indolizinonium fluoroborate

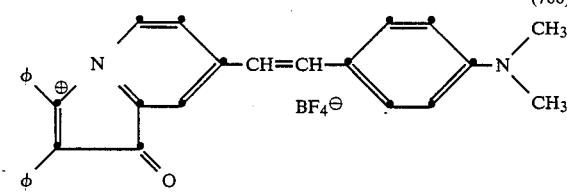

(780)

2,3-diphenyl-7-[2-(9-julolidyl)-1-ethenyl] 1-indolizinonium trifluoromethane sulfonate

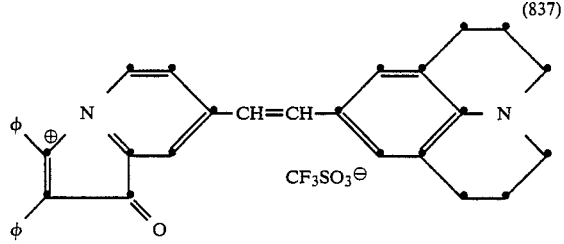

(837)

2,3-diphenyl-7-[3-(2,3-diphenyl-4-(4H)—pyranylidene-1-propenyl]-1-indolizinonium perchlorate

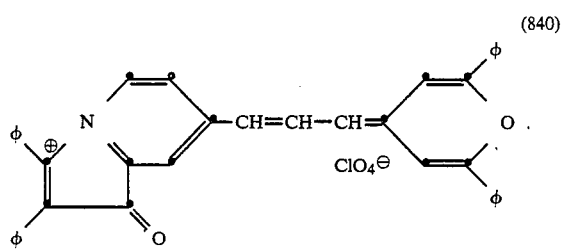

(840)

7-[2-(4-N,N—dimethylaminonaphthyl)-1-ethenyl]-2,3-diphenyl-1-indolizinonium fluoroborate

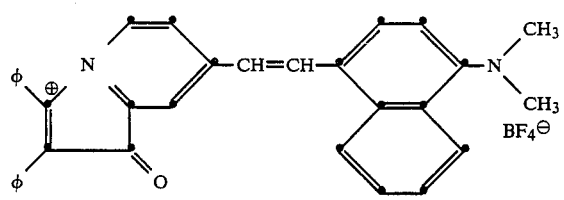

7-[4-(4-dimethylaminophenyl)-1-butadienyl]-1,2-diphenyl-3-indolizinonium trifluoromethane sulfonate

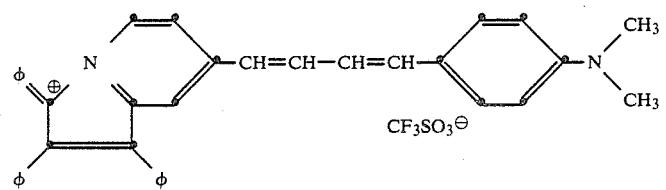

1-(3,5-di-tert-butyl-4-oxo-1-phenylidene)-
2-[7-(2,3-diphenyl-1-(7H)—indolizinonylidene)]ethane

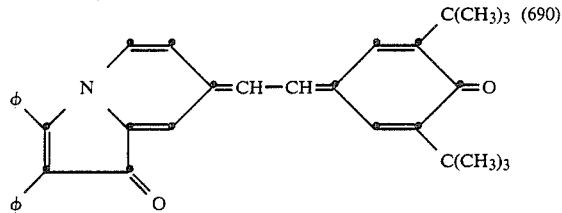

2,3-diphenyl-7-[2-(2,6-diphenyl-4-(4H)—
pryanylidene)-1-ethylidene]-1-hydroxy-
(7H)—indolizinium perchlorate

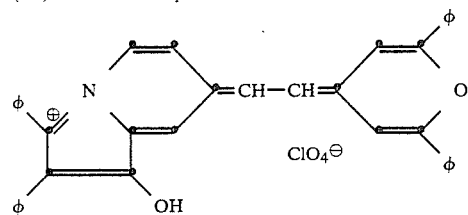

7-(2,2-diacetyl-1-ethenyl)-2,3-
diphenyl-1-indolizinol sodium salt

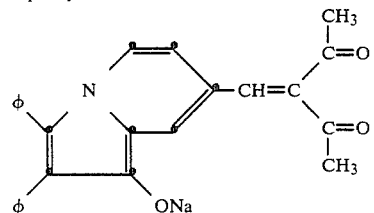

1-[7-(2,3-diphenyl-1-(7H)—indolizinonyli-
dene)]-2-[4-(2,6-diphenyl-4(4H)—pyranylidene)]ethane

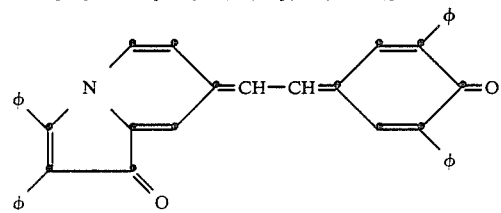

7-[1-cyano-2-(4-dimethylaminophenyl)-1-
ethenyl]-1,2-diphenyl-3-indolizinonium
trifluoromethane sulfonate

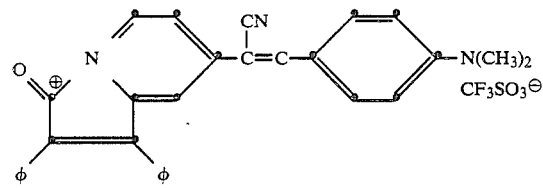

1,2-di-tert-butylphenyl-7-[4-(4-dimethyl-
aminophenyl)-1-(1,3-butadienyl)]-3-indol-
izonium trifluoromethane sulfonate 2,3-diphenyl-7-[2-(4-nitrophenyl)-1-
ethenyl]-1-indolizinol sodium salt

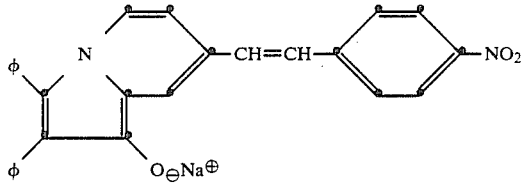

2,3-diphenyl-7-[2-(2,6-diphenyl-4-(4H)—
pyranylidene)-1-ethylidene]-1-acetoxy-(7H)—
indolizinium perchlorate

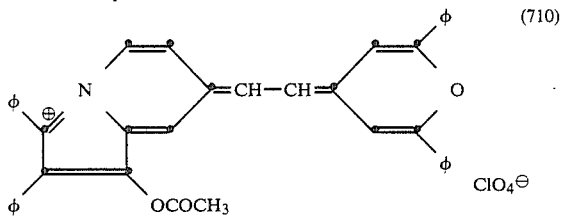

2,3-diphenyl-6-[2-(4-nitrophenyl)-1-
ethenyl]-1-indolizinol

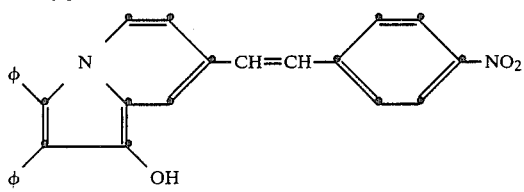

7-(3,3-diacetyl-1-propenylidene)-2,3-
diphenyl-1-(7H)—indolizinone

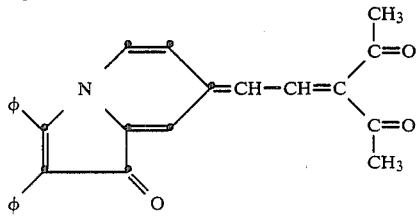

-continued
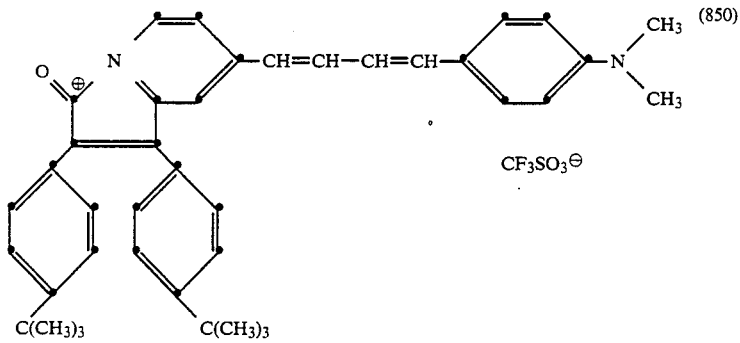
2,3-diphenyl-7-4-(2,6-diphenyl-4(4H)—
pyranylidene)-2-(2-butenyl)-1-
indolizinonium trifluoromethane sulfonate
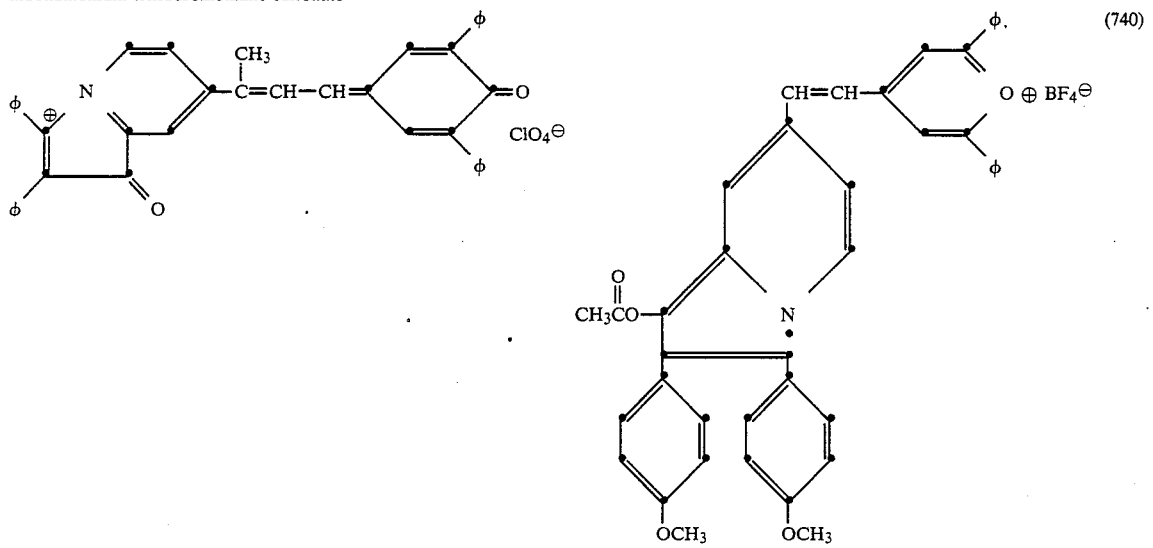
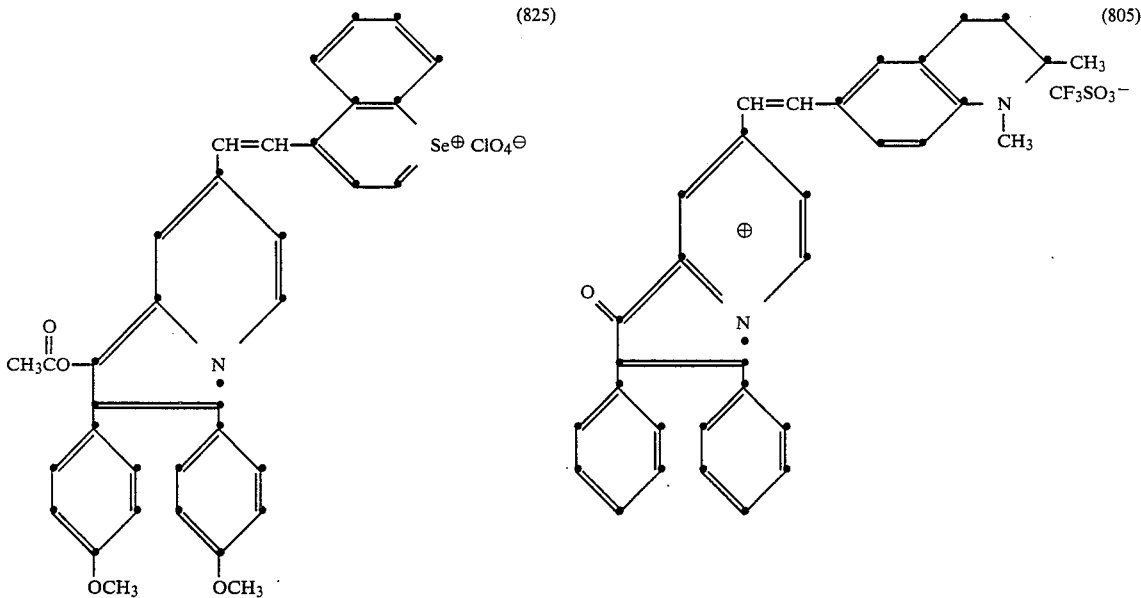
Additional compounds of this class are shown below in Tables I and II:

TABLE I

[Structure: pyridinium compound with HC=CHR' substituent, C=O, R'', R'' groups, and X⁻ counterion]

| Compound | R' | R'' | X⁻ | λmax (nm) |
|---|---|---|---|---|
| 1-1 | -C₆H₄-N(CH₃)₂ | CH₃O-C₆H₄- | BF₄ | 780 |
| 1-2 | -C₆H₄-N(CH₃)₂ | t-C₄H₉-C₆H₄- | BF₄ | 780 |
| 1-3 | julolidinyl | -C₆H₅ | BF₄ | 837 |
| 1-4 | julolidinyl | -CH₃O-C₆H₄- | BF₄ | 838 |
| 1-5 | julolidinyl | -CH₃-C₆H₄- | CF₃SO₃ | 838 |
| 1-6 | julolidinyl | -t-C₄H₉-C₆H₄- | BF₄ | 840 |
| 1-7 | julolidinyl | -t-C₄H₉-C₆H₄- | CF₃SO₃ | 840 |

TABLE I-continued
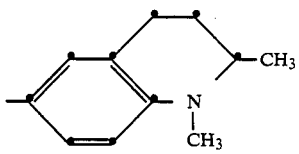
| Compound | R' | R" | X⊖ | λmax (nm) |
|---|---|---|---|---|
| 1-8 | 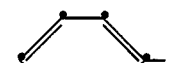 | 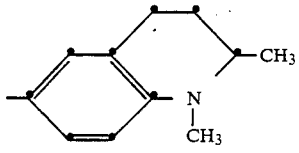 | CF$_3$SO$_3^\ominus$ | 820 |
| 1-9 | 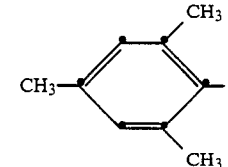 | 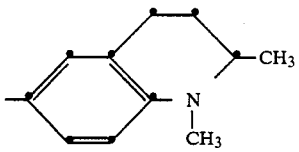 | CF$_3$SO$_3^\ominus$ | 815 |
| 1-10 | 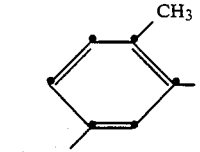 | 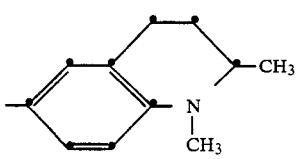 | CF$_3$SO$_3^\ominus$ | 815 |
| 1-11 | 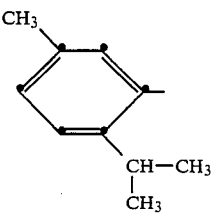 | 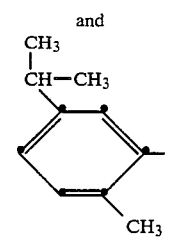 and 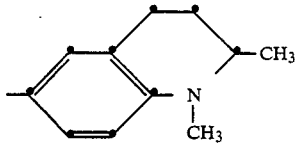 | CF$_3$SO$_3^\ominus$ | 815 |
| 1-12 | 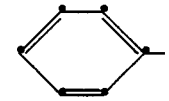 | 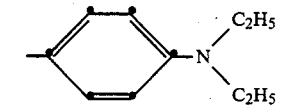 | CF$_3$SO$_3^\ominus$ | 805 |
| 1-13 | 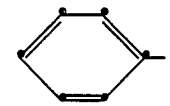 | | BF$_4$ | 800 |

TABLE II

[Structure shown at top of table:]

HC=CHR' group attached to a bicyclic ring system with N⊕ and C=O, with R" substituents, counter-ion X⊖

| Compound | R' | R" | X⊖ | λmax (nm) |
|---|---|---|---|---|
| 2-1 | [quinolinyl] | [phenyl] | BF₄ | 788 |
| 2-2 | [quinolinyl] | -t-C₄H₉—[phenyl] | BF₄ | 790 |
| 2-3 | [quinolinyl] | [phenyl] | CF₃SO₃ | 788 |
| 2-4 | [quinolinyl] | -t-C₄H₉—[phenyl] | CF₃SO₃ | 790 |

A further class of dyes according to the invention is represented by the formulas:

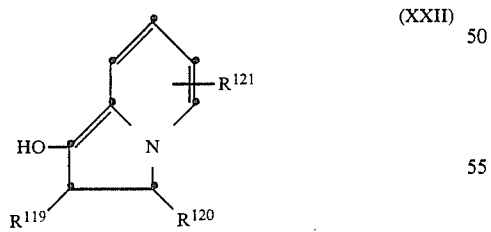

(XXII)

wherein:
R¹¹⁹ and R¹²⁰ are individually aryl containing 6 to 14 carbon atoms, such as phenyl and naphthyl; or, alkyl containing 1 to 20 carbon atoms, such as methyl, ethyl, propyl, decyl and eicosyl;

R¹²¹ is cyano, carboxy, formyl, acyl containing 2 to 18 carbon atoms, such as acetyl, propionyl and lauroyl; carboalkoxy containing 2 to 18 carbon atoms, such as carbomethoxy, carboethoxy and carbobutoxy; or aminocarbonyl containing 1 to 19 carbon atoms, such as unsubstituted aminocarbonyl, methylaminocarbonyl and dimethylaminocarbonyl which enables the compound to be a dye.

The compounds in this class are shown in the enol form, rather than the keto form. Examples of compounds within this class are as follows:

7-cyano-2,3-diphenyl-1-indolizinol (405)

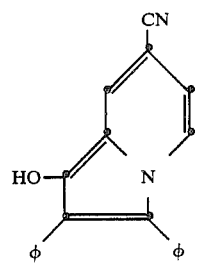

7-formyl-2,3-di-(4-methoxyphenyl)-1-indolizinol (423)

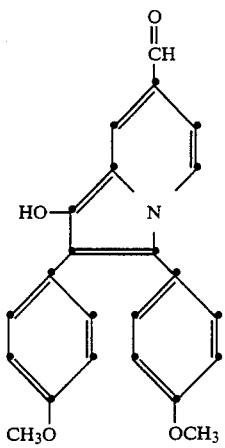

6-aminocarbonyl-2,3-diphenyl-1-indolizinol

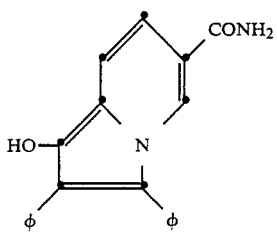

8-carboethoxy-2,3-diphenyl-1-indolizinol (490)

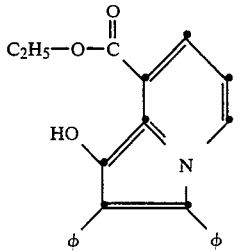

7-carboxy-2,3-diphenyl-1-indolizinol (420)

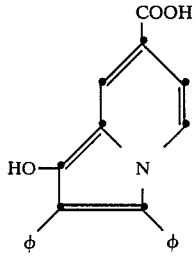

The oxoindolizine dyes according to the invention are prepared by a method comprising reacting (A) a pyridine compound, as described, with (B) a cyclopropenone compound, generally a photosensitive cyclopropenone. The resulting oxoindolizine or oxoindolizine compound is a new dye or a new dye is produced from the resulting oxoindolizine or oxoindolizinium compound by reacting the product with an appropriate color-forming compound, such as a color-forming coupler. Such a method is illustrated by the preparation of dyes represented by formulas I and II above comprising the steps:

(1) reacting (A) a pyridine compound, as described, with (B) a cyclopropenone, also as described, (2) reacting the resulting product from (1) with a color-forming compound, such as a color-forming coupler, in the presence of an oxidant or dehydrating agent that catalyzes formation of a dye according to the invention. Some of the compounds produced in step (1) are dyes which absorb in the visible region of the electromagnetic spectrum.

Optimum methods for preparation of dyes according to the invention will vary, depending upon the desired dye, particular starting material, such as the particular cyclopropenone, particular color-forming coupler, particular pyridine compound, solvents, reaction temperature, concentration of reactants, catalysts present and desired end use of the dye. The cyclopropenone and pyridine compounds are generally mixed in about stoichiometric concentrations; however, it is often useful to mix the reactants with an excess of the pyridine compound to provide better yields or different isomers.

The reactants for forming a dye according to the invention can be mixed in a reaction medium. For example, the cyclopropenone and pyridine compound can be mixed in a reaction medium comprising an organic solvent or medium that forms a coatable composition.

A reaction medium which comprises a solvent for the reactants is most useful. A useful solvent includes, for example, pyridine, chlorinated hydrocarbons, such as methylene chloride and chlorobenzene, toluene, dioxane, and tetrahydrofuran. Pyridine and some pyridine related solvents, such as 4-picoline, are especially useful in producing isomers. The reactants are generally mixed at about room temperature (about 19° C.) and then heated to reaction temperature, such as a temperature within the range of about 50° to about 150° C. The optimum reaction temperature will be influenced by the choice of solvent, the particular reactants, the desired dye, and other described factors.

When a dye according to the invention is formed by the reaction of a cyclopropenone with a pyridine compound and color-forming compound, such as a color-forming coupler, it is generally preferred that the reaction be carried out in chemical association with an appropriate oxidant, such as elemental iodine, copper bromide, copper acetate, benzoyl peroxide or copper acetyacetonate. The concentration of oxidant will vary, depending upon the particular reactants, processing conditions, desired dye, and reaction medium. An oxidant is especially useful in the reaction of a cyclopropenone with a pyridine compound and an active methylene coupler.

An example of a preparation according to the invention is the preparation of oxoindolizine dye represented by the formula:

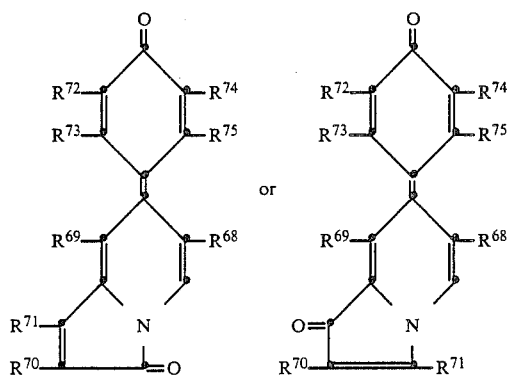

wherein: $R^{68}$, $R^{69}$, $R^{70}$, $R^{71}$, $R^{72}$, $R^{73}$, $R^{74}$ and $R^{75}$ are as defined above;
comprising the steps:
(1) reacting, such as by heating, a mixture of a pyridine compound, such as a pyridine compound as defined by structure (III), with a cyclopropenone represented by the formula:

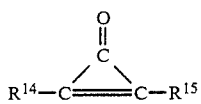
(IV)

wherein $R^{14}$ and $R^{15}$ are as defined above; and
(2) reacting, such as by heating, the product from (1) with a phenolic color-forming coupler represented by the formula:

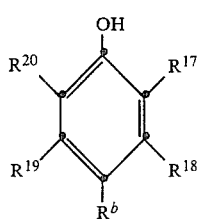
(VI)

wherein $R^{17}$, $R^{18}$, $R^{19}$ and $R^{20}$ and $R^b$ are as defined above, in the presence of an inorganic oxidant that catalyzes the formation of the indolizinone dye.

Useful inorganic oxidants are, for example, oxygen, copper acetate, copper chloride and iodine.

An especially useful process according to the invention is the process of preparing an oxoindolizine dye by the reaction of pyridine with a cyclopropenone and a phenolic coupler in a solvent consisting of pyridine with a large excess of the phenolic coupler. The reaction is preferably carried out at reflux temperature of about 115° C. to 150° C. under a nitrogen atmosphere. The catalyst is preferably iodine, with the reaction mixture containing 4 mole equivalents of iodine based on the concentration of cyclopropenone.

Another process according to the invention comprises reacting an aniline coupler, as described, in place of a phenolic color-forming coupler, with an oxoindolizine.

A further useful process for preparing an indolizinone dye by reaction of a pyridine compound with a cyclopropenone and then an active methylene coupler is carried out in a solvent, such as a solvent comprising methylene chloride, chlorobenzene or pyridine. The reactants are mixed in a concentration which provides a desired reaction mixture. The reaction temperature is generally within the range of about 0° C. to reflux temperature, which is about 40° C. to about 150° C. The proportion of pyridine compound based on the cyclopropenone compound is generally within the range of about an equimolar concentration of pyridine compound to a large excess. The proportion of active methylene coupler is generally within the range of equimolar concentration of the active methylene coupler to a large excess. The reaction generally is carried out at a temperature of about 50° C. to about 150° C. The reaction is preferably carried out in reactive association with a catalyst, such as metallic iodine, copper ions or copper ions and oxygen, with metallic iodine being preferred. The concentration of catalyst is generally a stoichiometric concentration based on the concentration of coupler. An excess of iodine catalyst is useful to provide increased yield.

In preparing an oxoindolizine dye by the reaction of pyridine compound with a cyclopropenone compound, the condensation is generally carried out in a solvent. The concentration of reactants is generally about stoichiometric. However, an excess of pyridine or picoline is often useful. The reaction temperature is generally within the range of 0° C. to about 95° C. The reaction is preferably carried out in chemical association with an oxidant, such as copper ions or air.

An especially useful method according to the invention comprises preparation of a dye represented by the structure (XXI) comprising reacting a compound represented by the structure

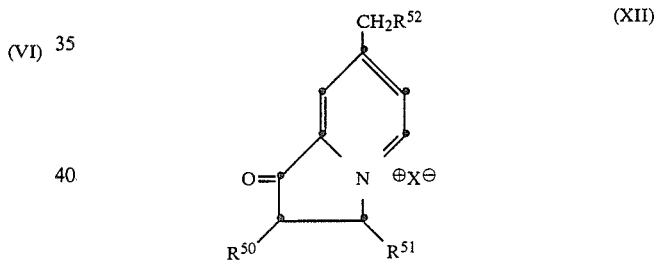
(XII)

wherein $X^\ominus$, $R^{50}$, $R^{51}$ and $R^{52}$ are as defined above, with an aldehyde or ketone represented by the formula

(XXIV)

wherein $R^{122}$ and $R^{123}$ are individually hydrogen or substituents that do not adversely affect the oxoindolizinium dye, such as alkyl containing 1 to 20 carbon atoms, for example, methyl, ethyl, propyl, butyl, decyl and eicosyl; aryl containing 6 to 14 carbon atoms, such as phenyl, tolyl, and naphthyl; or a heterocyclic group, such as pyridyl and julolidyl; and at least one of $R^{122}$ and $R^{123}$ is a monovalent group which completes a chromophore as defined.

Such compounds include, for example, pyrylium, flavylium, dimethylamino benzaldehyde and cinnimaldehyde compounds. These reactants (XII) and (XXIV) are reacted in about equimolar proportions in a suitable solvent, such as acetic anhydride, with or without a catalyst, such as piperidine or sodium acetate, at a temperature within the range of about 20° C. to about 140° C. The resulting dye crystallizes from the medium or is precipitated by addition of a non-solvent, such as water, ethyl ether or cyclohexane. An example of such a method according to the invention is a method of preparing a dye represented by the formula:

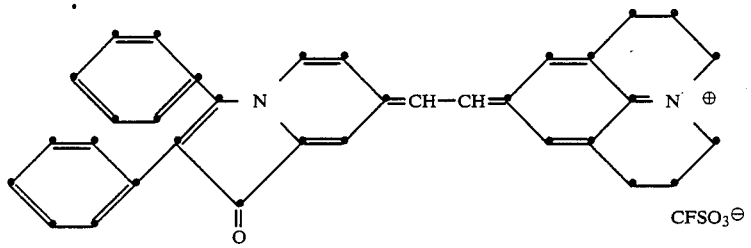

comprising the step:
(1) reacting a compound represented by the formula:

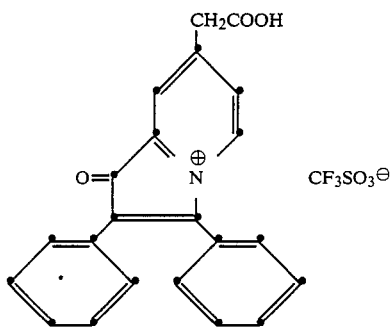

with a compound represented by the formula:

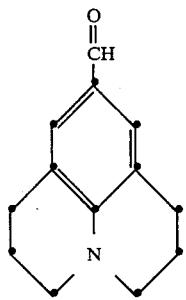

Another method of preparing dyes according to the invention comprises reacting an indolizinol represented by the formula:

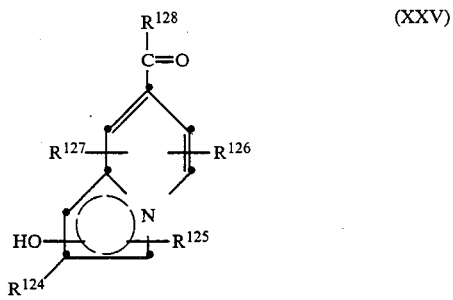

wherein
$R^{124}$ and $R^{125}$ are individually aryl containing 6 to 14 carbon atoms, such as phenyl, xylyl, methoxyphenyl, and naphthyl; or, alkyl containing 1 to 20 carbon atoms, such as methyl, ethyl, propyl, decyl and eicosyl;

$R^{126}$ is hydrogen, cyano, carboxy, formyl, acyl containing 2 to 18 carbon atoms, such as acetyl, propionyl, and lauroyl; carboalkoxy containing 2 to 10 carbon atoms, such as carbomethoxy, carboethoxy and carbobutoxy; or aminocarbonyl containing 1 to 19 carbon atoms, such as unsubstituted aminocarbonyl, methylaminocarbonyl and dimethylaminocarbonyl; and alkyl containing 1 to 20 carbon atoms, such as methyl, ethoxy, propyl, butyl, decyl and eicosyl;

$R^{127}$ is hydrogen or alkyl containing 1 to 4 carbon atoms, such as methyl, ethyl, propyl and butyl;

$R^{128}$ is alkyl containing 1 to 20 carbon atoms, such as methyl, ethyl, propyl, butyl, decyl and eicosyl; or aryl containing 6 to 14 carbon atoms, such as phenyl, tolyl, xylyl and naphthyl;

with an active methylene coupler, such as represented by formula (IX). The indolizinol represented by formula (XXV) and the active methylene coupler are reacted in about equimolar proportions in a suitable solvent, such as acetic anhydride, preferably with a catalyst, such as piperidine or sodium acetate, at a temperature within the range of about 20° C. to about 140° C. The resulting dye crystallizes from the reaction medium and is preferably precipitated by the addition of a non-solvent, such as water, ethyl ether or cyclohexane.

Many cyclopropenone and pyridine compounds are useful in an imaging material. Based on such a combination, an especially useful embodiment of the invention is an imaging material comprising a photosensitive cyclopropenone, in a binder, in reactive association with a pyridine compound that reacts with the cyclopropenone to form an oxoindolizine or oxoindolizinium compound.

A binder is especially useful in an imaging material according to the invention. The binder is preferably a film-forming compound which enables the imaging material to be coated on a suitable support. Most useful binders are those which are resistant to undesired changes in physical and chemical properties at processing temperatures, such as temperatures above about 80° C. The binder is preferably dimensionally stable at varying humidities and processing temperatures. Useful binders include synthetic polymeric materials which do not adversely affect the reaction between pyridine and cyclopropenone, such as cellulose acetate butyrate, poly(vinyl butyral), polyvinyl alcohol, polyvinyl chloride, polysulfonamide-styrene copolymers, copolymers of butadiene and styrene, polyisoprene and polysulfonamide binders. Gelatino binders are not especially useful because they tend to interfere with the reaction between cyclopropenone and pyridine.

Imaging materials according to the invention are also useful in a photographic element in combination with photographic materials not based on the reaction of cyclopropenone with a pyridine compound. For example, imaging elements according to the invention are useful which comprise a layer of a diazo or vesicular image-forming material and a layer of an imaging material according to the invention comprising a photosensitive cyclopropenone and a pyridine compound. Imaging materials according to the invention are also useful in combination with photographic silver halide materials which do not adversely affect the desired reaction of the cyclopropenone compound with the pyridine compound. An example of an imaging element comprises a layer of a photographic silver halide material and a layer of an imaging material comprising a photosensitive cyclopropenone and a pyridine compound. Photographic silver halide materials which are useful in such elements are described in, for example, Research Disclosure, November 1979, Item No. 18716; Research Disclosure, August 1979, Item No. 18431; Research Disclosure, December 1978, Item No. 17643; and Research Disclosure, June 1978, Item No. 17029. Useful photographic silver halides in such materials include, for example, silver chloride, silver bromide, silver bromoiodide, silver chlorobromoiodide and mixtures thereof.

Many oxoindolizine and oxoindolizinium dyes within Structures I and II are useful in imaging, such as in photothermographic imaging or in laser recording and reading applications. Especially useful dyes according to the invention are compounds that are image dyes or, alternatively, are capable of forming image dyes. Selection of an optimum indolizinone or indolizinium dye will depend upon such factors as the desired use, processing conditions, desired image, particular components with the dye, exposure means to form an image, and stability of the dye.

The following examples are included for a further understanding of the invention.

EXAMPLE 1

Photothermographic Element for Producing Red Dye Images

A dope solution was prepared containing 525 mg of poly(ethylene-co-1,4-cyclohexylenedimethylene-1-methyl-2,4-benzenedisulfonamide) (binder), 400 mg of 1-methyl-4-(4-pyridyl)pyridinium-para-toluene-sulfonate (pyridine compound) and 9.980 g of 2-methoxyethanol (solvent). The polysulfonamide binder and quaternary salt (pyridine compound) were dissolved in the 2-methoxyethanol by gentle agitation at room temperature (19° C.). A clear lacquer solution resulted. The dope was coated on a poly(ethylene terephthalate) film support at a wet coating thickness of 0.125 mm. The coating was dried by heating the material to about 24° C. (about 75° F.) for 30 minutes in a stream of air.

A second dope was prepared by dissolving 525 g of poly(styrene-co-butadiene) (KRO-3, which is a trade name of and available from Phillips Petroleum Company, U.S.A.), in 9.98 g of toluene with 40 mg of 1-phenyl-2-(para-methoxyphenyl)cyclopropenone (photosensitive cyclopropenone compound). Solution was produced by stirring at 22° C. for several hours. A clear lacquer solution resulted. The resulting dope containing the photosensitive cyclopropenone was coated directly over the first layer containing the pyridine compound. A wet coating thickness of 0.125 mm was applied. The resulting composite two-layer element was dried by warming the material to 45° C. for 30 minutes. The resulting photothermographic element according to the invention was exposed to a 250 watt mercury lamp for 20 seconds at a distance of 3 inches through a step wedge to produce a developable image in the photothermographic element. The desired dye image was produced by heating the photothermographic element after exposure to 150° C. for 3 seconds on a heated aluminum block. A brilliant red dye image was formed in the film. The resulting red dye image had a maximum absorption at 535 nm. The green light image density was measured by means of a commercial densitometer. The maximum image density was 1.83, and the minimum density was 0.08.

EXAMPLE 2

Photothermographic Element Producing a Blue Dye Image

A coating solution was prepared by dissolving 0.500 g of the polysulfonamide binder as described in Example 1 and 500 mg of 4-azastyryl-1-methyl-pyridinium para-toluenesulfonate (pyridine compound) in 10 g of 2-methoxyethanol (solvent). Solution was produced by stirring at room temperature (19° C.) A clear lacquer solution resulted. The resulting dope solution was coated on a poly(ethylene terephthalate) film support by means of a doctor blade to produce a wet coating thickness of 0.125 mm. The resulting coating was dried by heating the coating to about 24° C. (about 75° F.) for 30 minutes in a stream of rapidly moving air.

A second solution was prepared by dissolving 25 mg of phenylanisyl cyclopropenone and 0.50 g of poly(styrene-co-butadiene) resin in 10.0 g of toluene. A clear solution resulted upon stirring the mixture for 3 hours at room temperature (19° C.). The dope containing the photosensitive cyclopropenone was coated directly over the first layer containing the pyridine compound. A wet coating thickness of 0.125 mm was applied by means of a doctor blade. The composite two-layer photothermographic element according to the invention was dried by warming the resulting coating to about 24° C. (about 75° F.) for 30 minutes in a stream of rapidly moving air. A brilliant clear transparent film was obtained.

The resulting photothermographic element was imagewise exposed and then heated as described in Example 1. A blue dye image was formed in the film. The blue dye had a maximum absorption at 575 nm. The maximum density measured by integrated visible light on a commercial spectrophotometer was 1.50, with a minimum density of 0.08.

EXAMPLE 3

Photothermographic Element Producing a Green Image Absorbing in the Infrared Region A coating solution was prepared by dissolving 0.50 g of poly(styrene-co-butadiene) resin and 125 mg of 4,4'-dipyridylethylene (pyridine compound) in 10.0 g of toluene (solvent). A clear solution resulted upon stirring the resulting mixture at room temperature (19° C.). The coating solution was coated on a poly(ethylene terephthalate) film support containing a subbing layer. The composition containing the pyridine compound was coated at a wet coating thickness of 0.125 mm. The resulting coating was dried by heating to about 24° C. (about 75° F.) for 30 minutes. A second layer was coated over the layer containing the pyridine compound. The second layer was prepared from a coating solution produced by dissolving 0.50 g of poly(vinyl alcohol) in 9.50 g of water. The composition containing the poly(vinyl alcohol) was coated at a wet coating thickness of 0.125 mm over the first layer. The resulting composite film was dried by heating to 24° C. (about 75° F.) for 30 minutes. A top layer was then applied to the film. The top layer was prepared by coating a solution containing 125 mg of photosensitive phenylanisyl cyclopropenone and 0.50 g of poly(styrene-co-butadiene) dissolved in 10.0 g of toluene. The top layer was coated at a wet coating thickness of 0.125 mm. The resulting composite film was permitted to dry for 30 minutes at 24° C. (about 75° F.) in a rapidly moving air stream. The composite film was then imagewise exposed for 40 seconds and then heated as described in Examples 1 and 2. A dye image was produced in the film that had a maximum absorption in the infrared region of the electromagnetic spectrum at 815 nm. The image density of the resulting image was measured by integrated visible light in a commercial spectrophotometer. The maximum density of the image was 1.50, with a minimum density of 0.08.

EXAMPLE 4

One Layer Photothermographic Element

A coating solution was prepared by dissolving 0.50 g of poly(styrene-co-butadiene) resin, 40 mg of o,p-dianisylcyclopropenone (photosensitive cyclopropenone), and 40 mg of 1,2-bis(4-pyridyl)ethylene (pyridine compound) in 10.0 g of toluene. The dope was coated on a poly(ethylene terephthalate) film support at a wet coating thickness of 0.125 mm. The coating was dried by standing at 24° C. for two hours. The resulting photothermographic element was exposed to a 250 watt mercury lamp for 20 seconds at a distance of three inches through a mask to produce a developable image in the photographic element. The desired dye image was produced by heating the photothermographic element after exposure to 150° C. for 10 seconds on a heated aluminum block. An infrared dye was formed in the film with a maximum absorption at 830 nm. The image density in the unexposed section of the film was 2.5 at 830 nm as measured on a commercial spectrophotometer with a minimum density of 0.08. At 700 nm the maximum density was 0.95 and the minimum density was 0.09.

EXAMPLE 5

Preparation of 7,7'-(1,2-ethane-(E)-diylidene)bis-1,2-di-(4-tert-butylphenyl)-3(7H)-indolizinone A solution (10 percent by weight) of 2,3-di(4-tertiarybutylphenyl)cyclopropenone, in 4-picoline (pyridine compound), was prepared containing a trace of cupric acetate (catalyst). The solution was sparged with a stream of air to provide agitation and excess oxygen. The solution was heated on a steam bath to 80° C. to 95° C. for 15 minutes. A pasty cyan-colored slurry resulted. The resulting mixture was filtered to remove excess picoline, and the colored solids washed with acetone. The solids were dried under vacuum to remove the acetone-washed solvent. A 25 percent yield of the desired dye was obtained based on the cyclopropenone starting material. The dye had a maximum absorption at 695 nm in chloroform solution. The structure was confirmed by mass spectroscopy, nuclear magnetic resonance, infrared spectral analysis and x-ray diffraction.

EXAMPLE 6

Preparation of 7-(4-Pyridyl)-2,3-di-(4-methoxyphenyl)indolizinol, Benzyl Bromide Salt Equimolar amounts of benzyl bromide and 4,4'-dipyridine were dissolved in N,N-dimethylformamide to form approximately a 10 percent by weight solution. The solution was heated for 10 minutes on a steam bath at 95° C. to form the quaternary salt of bipyridine. The reaction mixture was cooled slightly, and an equimolar amount of 2,3-di(4-methoxyphenyl)cyclopropenone was added to the solution. The reaction mixture was heated for 15 minutes and quenched in excess cold water. A solution of 48 percent hydrobromic acid was added to the water-N,N-dimethylformamide solution to precipitate the desired dye product. The precipitated dye was removed by filtration and dried under vacuum. The dye had a maximum absorption density at B 535 nm in chloroform solution. The desired dye structure was confirmed by mass spectroscopy, nuclear magnetic resonance and infrared spectral analysis.

EXAMPLE 7

Preparation of 7-Dibenzoylmethylidene-2,3-di(4-methoxyphenyl)-1(7H)-indolizinone A 10 percent solution of 2,3-di(4-methoxyphenyl)cyclopropenone in pyridine was refluxed under nitrogen for 15 minutes. The resulting solution was cooled slightly, and an equivalent amount of dibenzoylmethane based on the cyclopropenone was added to the green solution. The reaction mixture was refluxed for 60 minutes. The resulting reaction mixture was again cooled, and four equivalents of iodine dissolved in a small amount of pyridine was added to the reaction mixture. The mixture was further heated at 90° C. on a steam bath for 15 minutes. The bright blue solution was quenched by pouring it into cold excess dilute hydrochloric acid. The desired dye precipitated and was removed from the solution by filtering. A 95 percent yield of the desired dye was obtained based on the starting cyclopropenone. The dye was chromatographed on silica gel to provide a purified product. The maximum absorption of the dye was at 605 nm in chloroform solution. The structure of the dye was confirmed by mass spectroscopy, nuclear magnetic resonance and infrared analysis.

EXAMPLE 8

Preparation of 7-Formyl-2,3-di(4-methoxyphenyl)-1-indolizinol

Equivalent amounts of 4-formylpyridine and 2,3-di(4-methoxyphenyl)cyclopropenone were dissolved in sufficient para-dioxane to form approximately a 10 percent solution. The mixture was refluxed at 102° C. under nitrogen for 2 hours. Sufficient water was then added to the reaction mixture to bring it to the cloud point at 80° C. The reaction mixture was then cooled to room temperature, and the product allowed to crystallize. The crystals were collected by filtration, and washed with a small amount of water. The dried crystals were the desired dye. The dye was produced in a 95 percent yield based on the input of cyclopropenone. The yellow dye had a maximum absorption of 435 nm in chloroform solution. The structure of the dye was confirmed by mass spectroscopy, nuclear magnetic resonance and infrared analysis.

EXAMPLES 9–12

Other yellow dyes were prepared by a modification of the procedure described in Example 8. The modification consisted of substituting the particular pyridine needed to obtain the desired dye for the 4-formyl pyridine described in Example 8. Structures were confirmed by mass spectrometry, nuclear magnetic resonance and elemental analysis. Examples of the yellow dyes prepared are as follows:

EXAMPLE 9

7-carboxyl-2,3-diphenyl-1-indolizinol

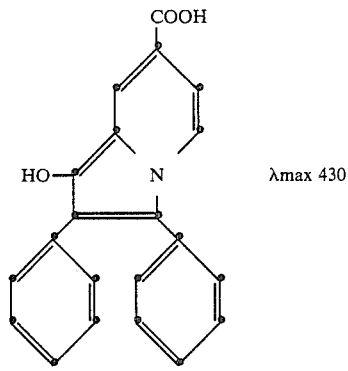

λmax 430

EXAMPLE 10

7-carbomethoxy-2,3-di(4-tert-butylphenyl)-1-indolizinol

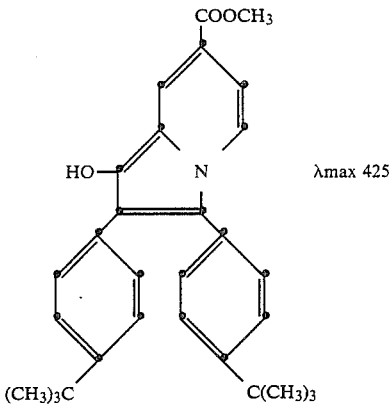

λmax 425

EXAMPLE 11

7-aminocarbonyl-2,3-diphenyl-1-indolizinol

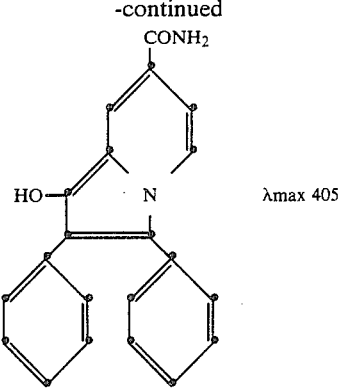

λmax 405

EXAMPLE 12

7-cyano-2,3-diphenyl-1-indolizinol

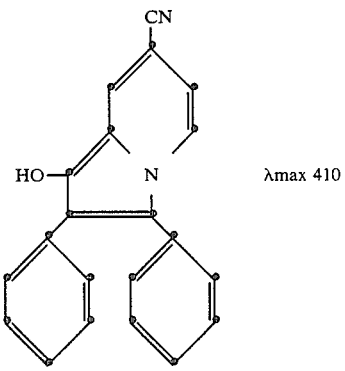

λmax 410

EXAMPLE 13

Preparation of 1,2-di-(4-tert-butylphenyl)-7-[4-(4-dimethylaminophenyl)-1-(1,3-butadienyl)]-3-indolizinonium trifluoromethanesulfonate Equivalent amounts of 4-dimethylaminocinnamaldehyde and 1,2-di(tert-butylphenyl-7-methyl-3-indolizinonyl trifluoromethane sulfonate were dissolved in acetic anhydride to form approximately a 10 percent solution. The reaction mixture was heated at 70°–90° C. for five minutes, diluted with ether and the resulting product collected by filtration. The crude product was recrystallized from acetone to furnish the desired dye.

EXAMPLE 14

Preparation of 7-(4-dimethyl-aminophenyl)-2,3-diphenyl-1-indolizinonium fluoborate A 10% solution of 1,2-diphenyl-1-indolizinonium triiodide in dimethylaniline was warmed at 70°–90° C. for 10 minutes. The resulting solution was diluted with ether and the resulting solid redissolved in acetone. The desired dye was precipitated by the addition of dilute fluoboric acid to the solution.

EXAMPLE 15

Preparation of 7-diethylamino-2,3-diphenyl-1-indolizinonium fluoborate

A 10% solution of 2,3-diphenyl-1-indolizinonium triiodide in pyridine was treated with two equivalents of anhydrous diethyl amine and heated at 70°–90° C. for 15 minutes. The reaction mixture was poured into ether and filtered to furnish the crude dye. The dye was washed thoroughly with water to remove soluble salts to furnish purified product.

EXAMPLES 16–18

Use of Dyes in Optical Disc for Laser Writing and Reading

The use of oxoindolizine and oxoindolizinium dyes described herein in an optical disc for laser writing and reading is the result of the joint work of Donald H. Wadsworth, Harold T. Thomas, George L. Fletcher and Charles H. Weidner. The oxoindolizine and oxoindolizinium dyes for use in an optical disc were selected to provide the desired characteristics for laser writing and reading including among other characteristics, the desired solubility, absorption and stability characteristics.

In each of the examples an optical disc for laser writing and reading was prepared by coating, on a support designed for an optical disc, a layer of an amorphous composition comprising a binder, such as cellulose nitrate, and an oxoindolizine or oxoindolizinium dye having an absorption at a wavelength at which the laser was tuned, such as a wavelength in the range of about 300 to about 1000 nanometers. Optical discs were prepared by techniques described in, for example, "Disc-Storage Technology" by Robert M. White, *Scientific American*, August 1980, beginning at page 138, and *Research Disclosure*, November, 1978, Item No. 17522, the descriptions of which are incorporated herein by reference.

The dyes for Examples 16, 17 and 18 were individually incorporated in a coating composition containing cellulose nitrate (binder) and cyclohexanone (solvent). The resulting compositions were coated on optical disc supports containing a reflective metal layer, such as aluminum. The resulting optical discs were imagewise exposed to a laser emitting at 800 nanometers pulsed at 10 MHz and a 50% duty cycle in a 30 KHz bandwidth to provide an image on each optical disc. Reading from the exposed optical discs was by monitoring the feedback from the same laser. The following dyes were tested in the video discs:

| Example No. | Dye |
|---|---|
| 16 | 2,3-diphenyl-7-[2-(9-julolidinyl)ethenyl]-1-oxo-1H—indolizinium trifluoromethanesulfonate |
| 17 | 2,3-bis(4-t-butylphenyl)-7-[2-(9-julolidinyl)-ethenyl]-1-oxo-1H—indolizinium trifluoromethanesulfonate |
| 18 | 1,2-bis(4-t-butylphenyl)-7-[2-(9-julolidinyl)-ethenyl]-3-oxo-3H—indolizinium trifluoromethanesulfonate |

An image was recorded and read on each of the optical discs. The recording power at the discs was 12 mW in each case.

The invention has been described in detail with particular reference to preferred embodiments thereof, but it will be understood that variations and modifications can be effected within the spirit and scope of the invention.

What is claimed is:

1. A dye selected from the group consisting of oxoindolizine and oxoindolizinium dyes and combinations thereof wherein
   (a) the oxo group of said dyes is in the 1- or 3-position of the oxoindolizine or oxoindolizinium nucleus,
   (b) said dyes contain in the 7-position of the oxoindolizine or oxoindolizinium nucleus a chromophore group which enables said dyes to have a maximum absorption of electromagnetic radiation at wavelengths within the range of 300 to 1000 nanometers, and
   (c) said oxoindolizine or oxoindolizinium nucleus contains, in at least one of the 1-, 2- and 3-positions, alkyl containing 1 to 18 carbon atoms, aryl containing 6 to 20 carbon atoms, or aryl containing 6 to 20 carbon atoms substituted by alkyl containing 1 to 5 carbon atoms, alkoxy containing 1 to 5 carbon atoms, or aryloxy containing 6 to 10 carbon atoms.

2. A dye selected from the group consisting of
   (i) 7-methylidene-1 or 3-oxoindolizine dyes;
   (ii) 7-(4-oxo-2,5-cyclohexadiene-1-ylidene)-1 or 3-oxoindolizine dyes;
   (iii) 7-(1 or 3-oxoindolizin-7-ylidene)-1 or 3-oxoindolizine dyes;
   (iv) 7-(1 or 3-oxoindolizin-7-ylidene)ethylidene-1 or 3-oxoindolizine dyes;
   (v) 7-(1 or 3-oxoindolizin-7-ylidene)methyliene-1 or 3-oxoindolizinium salt dyes;
   (vi) 7-(2 or 4-aminoaryl)-1 or 3-oxoindolizine dyes; and
   (vii) 7-pyridinium-1 or 3-oxoindolizine dyes; and combinations of said dyes;
   wherein said dyes contain, in the 7-position of the indolizine or indolizinium nucleus, a chromophore group which enables said dyes to have a maximum absorption of electromagnetic radiation at a wavelength within the range of 300 to 1000 nanometers; and
   wherein said indolizine or indolizinium nucleus contains, in at least one of the 1-, 2- and 3-positions, alkyl containing 1 to 18 carbon atoms, aryl containing 6 to 20 carbon atoms, or aryl containing 6 to 20 carbon atoms substituted by alkyl containing 1 to 5 carbon atoms, alkoxy containing 1 to 5 carbon atoms, or aryloxy containing 6 to 10 carbon atoms.

3. A dye as in claim 2 which has a maximum absorption at a wavelength in the infrared region of the electromagnetic spectrum.

4. A dye represented by the formula:

(I)

wherein
R$^1$ and R$^2$ are independently selected from alkyl containing 1 to 18 carbon atoms; aryl containing 6 to 20 carbon atoms; aryl containing 6 to 20 carbon atoms substituted by alkyl containing 1 to 5 carbon atoms, alkoxy containing 1 to 5 carbon atoms, or aryloxy containing 6 to 10 carbon atoms;
R$^3$ is a divalent group which, with the indolizinone nucleus, completes an organic chromophore which enables said dye to absorb electromagnetic radiation within the range of 300 to 1000 nanometers;
R$^4$ is hydrogen, alkyl containing 1 to 18 carbon atoms; cyano; acyl containing 2 to 20 carbon atoms; carboalkoxy containing 2 to 18 carbon atoms; aminocarbonyl; acyloxy containing 2 to 18 carbon atoms; bromine or chlorine; and
R$^5$ is hydrogen, chlorine, bromine or alkyl containing 1 to 18 carbon atoms.

5. A dye represented by the formula:

(II)

wherein
X$^\ominus$ is an anion;
R$^6$ and R$^7$ are independently selected from alkyl containing 1 to 18 carbon atoms, aryl containing 6 to 20 carbon atoms, and aryl containing 6 to 20 carbon atoms substituted by alkyl containing 1 to 5 carbon atoms, alkoxy containing 1 to 5 carbon atoms, or aryloxy containing 6 to 10 carbon atoms;
R$^8$ is a monovalent group which, with the indolizinium nucleus, completes an organic chromophore which enables said dye to have a maximum absorption of electromagnetic radiation at a wavelength within the range of 300 to 1000 nanometers;
R$^9$ is hydrogen, alkyl containing 1 to 18 carbon atoms; cyano; acyl containing 2 to 20 carbon atoms; carboalkoxy containing 2 to 18 carbon atoms; aminocarbonyl; acyloxy containing 2 to 18 carbon atoms; bromine or chlorine; and
R$^{10}$ is hydrogen, chlorine, bromine or alkyl containing 1 to 18 carbon atoms.

6. A dye represented by the formula:

wherein:
R$^{68}$ is hydrogen, alkyl containing 1 to 18 carbon atoms, cyano, acyl containing 2 to 18 carbon atoms, carboalkoxy containing 2 to 18 carbon atoms, aminocarbonyl, acyloxy containing 2 to 18 carbon atoms, bromine or chlorine;
R$^{69}$ is hydrogen, chlorine, bromine, or alkyl containing 1 to 18 carbon atoms;
R$^{70}$ and R$^{71}$ are independently selected from alkyl containing 1 to 18 carbon atoms, aryl containing 6 to 20 carbon atoms, and aryl containing 6 to 20 carbon atoms substituted by alkyl containing 1 to 5 carbon atoms, alkoxy containing 1 to 5 carbon atoms, or aryloxy containing 6 to 10 carbon atoms;
R$^{72}$ and R$^{73}$ are individually hydrogen, alkyl containing 1 to 22 carbon atoms, aryl containing 6 to 20 carbon atoms, amino, carboxamido, sulfonamido, sulfamyl, carbamyl, halogen, alkoxy containing 1 to 18 carbon atoms; or R$^{72}$ and R$^{73}$ taken together represent the atoms necessary to complete a benzo group, and
R$^{74}$ and R$^{75}$ are individually hydrogen, hydroxy, alkyl containing 1 to 22 carbon atoms, aryl containing 6 to 20 carbon atoms, amino, carboxamido, sulfonamido, sulfamyl, carbamyl, halogen or alkoxy containing 1 to 18 carbon atoms.

7. A dye represented by the formula:

wherein:
R$^{108}$ and R$^{109}$ are individually aryl containing 6 to 14 carbon atoms or alkyl containing 1 to 20 carbon atoms;
R$^{110}$ is CH, phenylene or naphthylene;
R$^{111}$ is phenylene or naphthylene; and
n and m are individually 0 or 1.

8. A dye represented by the formula:

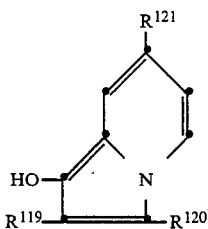

wherein
- $R^{119}$ and $R^{120}$ are independently selected from aryl containing 6 to 12 carbon atoms and alkyl containing 1 to 20 carbon atoms; and
- $R^{121}$ cyano, carboxy, formyl, acyl containing 2 to 18 carbon atoms, carboalkoxy containing 2 to 10 carbon atoms, or aminocarbonyl containing 1 to 19 carbon atoms.

9. A dye represented by the formula:

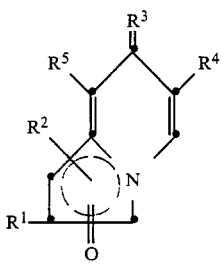

wherein
- $R^1$ and $R^2$ are independently selected from alkyl containing 1 to 18 carbon atoms; aryl containing 6 to 20 carbon atoms; and aryl substituted by alkyl containing 1 to 5 carbon atoms; alkoxy containing 1 to 5 carbon atoms; or aryloxy containing 6 to 10 carbon atoms;
- $R^3$ is a divalent group selected from the group consisting of groups derived from active methylene couplers, groups derived from phenolic couplers and groups derived from aniline couplers which, with the indolizine nucleus, complete a dye which absorbs electromagnetic radiation at a maximum wavelength of absorption within the range of 300 to 1000 nanometers;
- $R^4$ is hydrogen, alkyl containing 1 to 18 carbon atoms; cyano; acyl containing 2 to 20 carbon atoms; carboalkoxy containing 1 to 18 carbon atoms; aminocarbonyl; acyloxy containing 2 to 18 carbon atoms; bromine or chlorine; and
- $R^5$ is hydrogen, chlorine, bromine or alkyl containing 1 to 18 carbon atoms.

10. A dye represented by the formula:

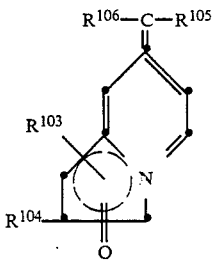

wherein
- $R^{103}$ and $R^{104}$ are independently selected from alkyl containing 1 to 20 carbon atoms; aryl containing 6 to 20 carbon atoms; and aryl substituted by alkyl containing 1 to 5 carbon atoms; alkoxy containing 1 to 5 carbon atoms; or aryloxy containing 6 to 10 carbon atoms;
- $R^{105}$ is hydrogen; aryl containing 6 to 20 carbon atoms; acyl containing 2 to 18 carbon atoms; carboalkoxy containing 2 to 18 carbon atoms; cyano; and aminocarbonyl containing 1 to 18 carbon atoms;
- $R^{106}$ is aryl containing 6 to 20 carbon atoms; acyl containing 2 to 18 carbon atoms; carboalkoxy containing 2 to 18 carbon atoms; aminocarbonyl containing 1 to 18 carbon atoms; or cyano.

11. A dye represented by the formula:

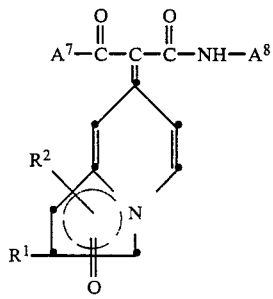

wherein
- $R^1$ and $R^2$ are independently selected from alkyl containing 1 to 18 carbon atoms; aryl containing 6 to 20 carbon atoms; and aryl containing 6 to 20 carbon atoms substituted by alkyl containing 1 to 5 carbon atoms; alkoxy containing 1 to 5 carbon atoms; or aryloxy containing 6 to 10 carbon atoms;
- $A^7$ and $A^8$ are independently selected from alkyl containing 1 to 18 carbon atoms; aryl containing 6 to 14 carbon atoms; amino; and vinyl.

12. A dye represented by the formula:

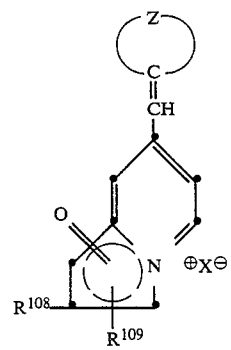

wherein
- $X^\ominus$ is an anion;
- $R^{108}$ and $R^{109}$ are independently selected from aryl containing 6 to 20 carbon atoms; alkyl containing 1 to 20 carbon atoms; or aryl containing 6 to 20 carbon atoms substituted by alkyl containing 1 to 5 carbon atoms; alkoxy containing 1 to 5 carbon atoms; or aryloxy containing 6 to 10 carbon atoms;

Z represents the atoms necessary to complete a 4-pyranylidene, 7-1(7H)-indolizinylidene, 4-thiopyranylidene, 4-selenopyranylidene, 4-coumarinylidene or pyrazolinoylidene group.

13. A dye represented by the formula:

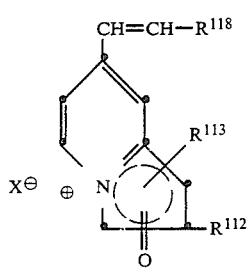

wherein $R^{112}$ and $R^{113}$ are independently selected from aryl containing 6 to 20 carbon atoms; alkyl containing 1 to 20 carbon atoms; and aryl containing 6 to 20 carbon atoms substituted by alkyl containing 1 to 5 carbon atoms, alkoxy containing 1 to 5 carbon atoms, or aryloxy containing 6 to 10 carbon atoms;

$R^{118}$ is a group necessary to complete an organic chromophore which enables said dye to absorb electromagnetic radiation within the range of 300 to 1000 nanometers; and;

$X^{\ominus}$ is an anion.

14. A dye represented by the formula:

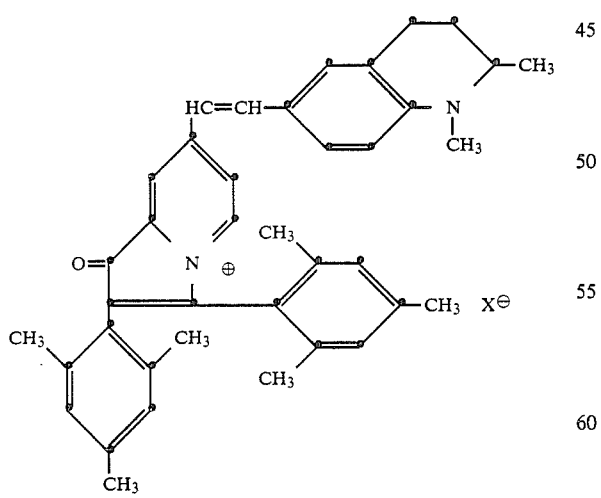

$X^{\ominus}$ is a anion.

15. A dye selected from the group consisting of compounds represented by the formulas:

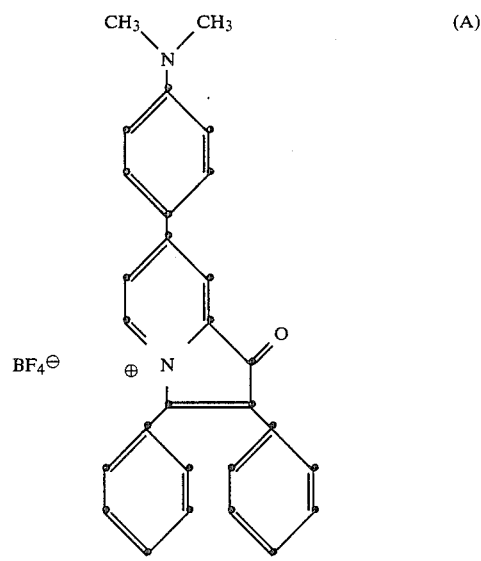

(A)

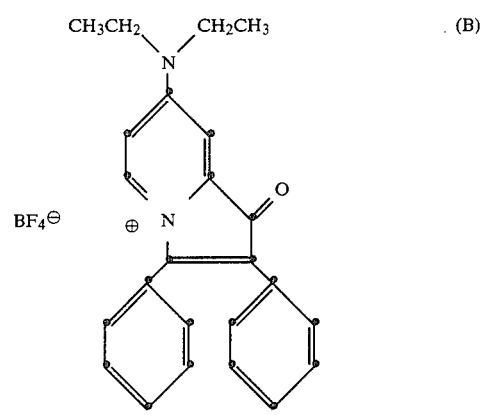

(B)

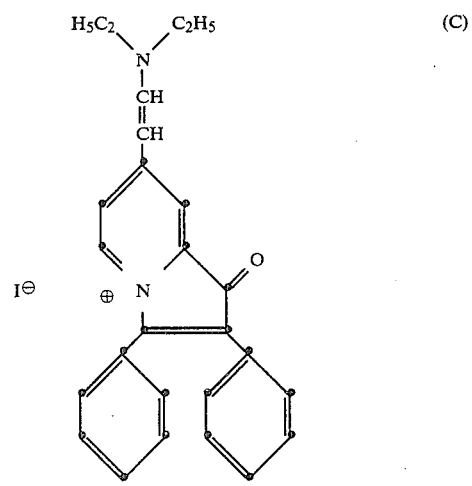

(C)

109
-continued
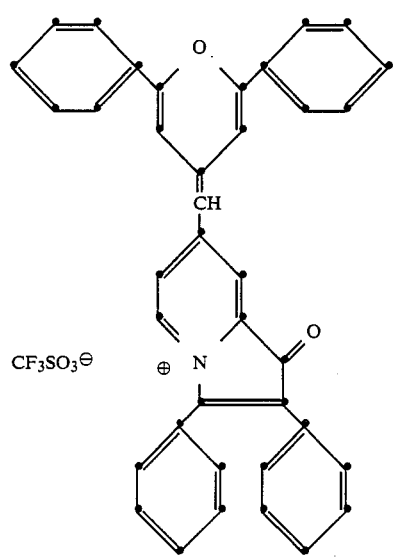
CF₃SO₃⁻
(D)
110
-continued
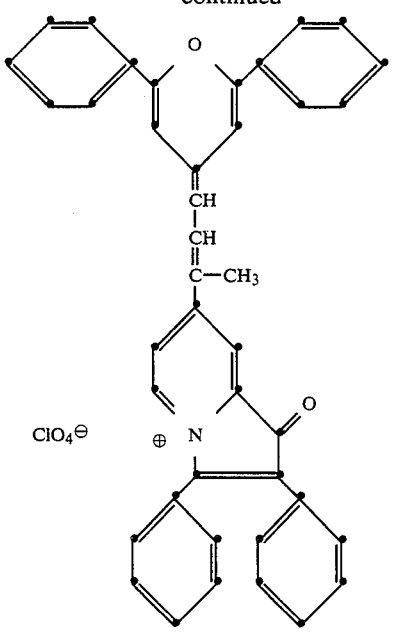
ClO₄⁻
(E)
and combinations thereof.
* * * * *